(12) United States Patent
Rafferty

(10) Patent No.: US 8,080,548 B2
(45) Date of Patent: Dec. 20, 2011

(54) DIALKYLAMINO ALKYL ESTERS OF PIVAGABINE AS MEDICAMENTS FOR THE TREATMENT OF CENTRAL NERVOUS SYSTEM DISORDERS

(75) Inventor: Michael Rafferty, Olathe, KS (US)

(73) Assignee: Cenerx Biopharma, Inc., Cary, NC (US)

( * ) Notice: Subject to any disclaimer, the term of this patent is extended or adjusted under 35 U.S.C. 154(b) by 51 days.

(21) Appl. No.: 12/538,683

(22) Filed: Aug. 10, 2009

(65) Prior Publication Data

US 2010/0099678 A1    Apr. 22, 2010

Related U.S. Application Data

(63) Continuation of application No. 11/946,708, filed on Nov. 28, 2007, now Pat. No. 7,632,836.

(60) Provisional application No. 60/861,897, filed on Nov. 30, 2006.

(51) Int. Cl.
*A61K 31/5375*  (2006.01)
*A61K 31/195*   (2006.01)
*A61P 25/22*    (2006.01)
*A61P 25/24*    (2006.01)
*A61P 25/18*    (2006.01)
*A61P 3/04*     (2006.01)
*A61P 29/00*    (2006.01)
*A61P 25/06*    (2006.01)
*A61P 25/16*    (2006.01)
*A61P 25/28*    (2006.01)

(52) U.S. Cl. ..................... 514/237.8; 514/563

(58) Field of Classification Search .......... 514/237.8, 514/563
See application file for complete search history.

(56) References Cited

U.S. PATENT DOCUMENTS

2003/0176398 A1    9/2003   Gallop et al.
2005/0009814 A1    1/2005   Iwayama et al.

FOREIGN PATENT DOCUMENTS

WO    WO98/38988    9/1998

OTHER PUBLICATIONS

Gary Stix, Science American, p. 51-57 (Jun. 2010).*
Gerra et al., Behavioural Brain Research, V122 (2001), p. 93-101.*
Boussard et al., Bioploymers, 1977, 16(5), pp. 1033-1052, Abstract.

* cited by examiner

*Primary Examiner* — Yong Chu
(74) *Attorney, Agent, or Firm* — Womble Carlyle Sandridge & Rice, LLP

(57) ABSTRACT

The present embodiments are related to the compound of Formula 1 or Formula 2 below and pharmaceutical formulations thereof as well as treatments for a wide variety of Central Nervous System disorders with the pharmaceutical formulations. Some embodiments include the use of a variety of the instant compounds which surprisingly and advantageously exhibit improved pharmacokinetic and therapeutic profiles in comparison to pivagabine.

Formula 1:

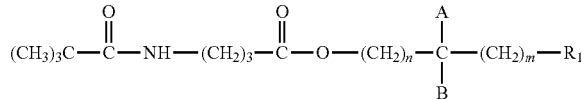

Formula 2:

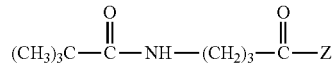

14 Claims, 24 Drawing Sheets

DIALKYLAMINO ALKYL ESTERS OF PIVAGABINE AS MEDICAMENTS FOR THE TREATMENT OF CENTRAL NERVOUS SYSTEM DISORDERS

CROSS-REFERENCE TO RELATED APPLICATIONS

This application claims priority to and is a continuation of U.S. application Ser. No. 11/946,708 filed on Nov. 28, 2007 now U.S. Pat. No. 7,632,836, which claims priority under 35 U.S.C. §119(e) to U.S. Provisional Application No. 60/861,897 filed Nov. 30, 2006, both of which are hereby incorporated by reference in their entirety.

BACKGROUND OF THE INVENTION

1. Field of the Invention

Compounds and methods related to derivatives of pivagabine for the treatment of central nervous system disorders.

2. Description of the Related Art

Pivagabine, or 4-[(2,2-dimethyl-1-oxopropyl)amino]butanoic acid:

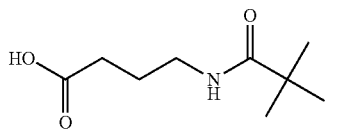

4-[(2,2-dimethyl-1-oxopropyl)amino]butanoic acid is a hydrophobic derivative of GABA which can cross the haemato-encephalic barrier and act as an active pharmaceutical compound against hypertension and cerebral disturbances, such as epilepsy. Pivagabine has been found to be substantially free of toxic effects in vivo in mouse and in rat; in fact, LD50 by intravenous route is 1750 mg/kg in the mouse while no toxic effects were observed up to the dose of 1 g/kg by intraperitoneal route in the rat. It shows a certain anti-depressive and anxiolytic activity in the mouse and can be used to treat mood disturbances, anxiety disorders, somatoform disorders and adjustment disorders.

However, pivagabine was originally developed as an analog of GABA with the proposition that it would be hydrolyzed to GABA after entering the brain. ADME (Absorption, Distribution, Metabolism & Excretion) studies suggest that only very low levels of GABA are detected in the brain. Therefore, the mechanism of action of pivagabine is likely not related to GABA. In attempts to elucidate the mechanism of action it was discovered that pivagabine affects the CRF protein content of specific brain regions (hypothalamus and cerebral cortex) particularly during stress conditions (application of foot shock in rodents). This effect is centrally mediated and does not require an intact hypothalamic-pituitary-adrenal axis. Also, in modulating CRF, pivagabine is not acting as a CRF-1 receptor antagonist since it does not reverse the effects of CRF administered directly into the brain of rodents.

Unfortunately, current forms of pivagabine are poorly absorbed by the brain which is the relevant organ for the pharmacologic actions of pivagabine. Thus there is a need to optimize brain levels of pivagabine when administrated by the oral route. Optimized bioavailability of the drug at its site of action is one of the most important aims of the pharmaceutical industry during the development phase of a new product. Bioavailability represents the quantity of a biological agent, i.e. the active component, absorbed from a pharmaceutical formulation that is absorbed into blood and circulated, the rate of this absorption, and the rate of clearance from the body after the drug has been absorbed. This implies that the molecule crosses one or several biological membranes before reaching the site of action, which is the brain in the case of pivagabine. It has been generally considered that the physicochemical properties of an orally administered drug determine its bioavailability. Among these parameters are the molecular weight (very low permeability is known for therapeutics with molecular weight more than 600 D), the pKa, and the lipophilicity as characterized by the octanol/water partition coefficient (Log D).

In particular, though pivagabine is rapidly absorbed into the blood, the amount of drug that enters the brain is relatively small (the brain concentration of pivagabine is only about 7% that of the blood in rats). Therefore, high doses of the drug (1800 mg/day in humans) have to be administered to achieve the desired behavioral effects. This presents a problem with manufacturing (high volumes have to be produced) and with developing finished formulations (tablets or capsules) that are commercially acceptable. One problem with pivagabine is that its administration has not achieved high enough levels in the central nervous system. The current embodiments address these concerns and provide other advantages as well.

SUMMARY OF THE INVENTION

Some embodiments relate to a compound having the following structure:

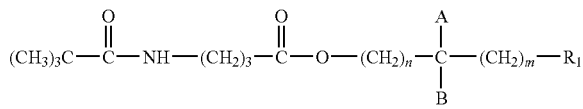

wherein, m is 0, 1, 2, 3 or 4;
wherein, n is 1, 2, 3, or 4;
wherein A and B are independently selected from H, $C_1$-$C_4$ alkyl;
wherein A and B may together represent a cyclic hydrocarbon moiety consisting of 2, 3, 4 or 5 methylene units;
and wherein
$R_1$ is selected from
a) the group consisting of,

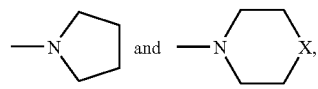

wherein X is selected from the group consisting of methylene ($CH_2$), unsubstituted or substituted nitrogen, oxygen, or sulfur or
b) the group consisting of an unsymmetrical amine group of the formula

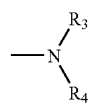

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

and —$SR_8$, wherein $R_5$, $R_6$, $R_7$ and $R_8$ are independently selected from H, a $C_1$-$C_8$ branched alkyl and a $C_1$-$C_8$ linear alkyl; and wherein $R_3$ and $R_4$ are not identical; and solvates, hydrates, salts, isomers, including pure enantiomers and diastereomers thereof and mixtures in any proportion thereof. It will be understood that any of the forgoing compounds can be in a crystalline or amorphous state or a mixture thereof.

Some embodiments relate to compounds wherein $R_1$ is

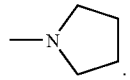

Some embodiments relate to compounds wherein $R_1$ is

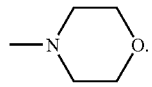

Some embodiments relate to compounds wherein $R_1$ is

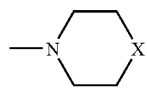

wherein X is selected from the group consisting of methylene ($CH_2$), unsubstituted or substituted nitrogen, oxygen, or sulfur.

Some embodiments relate to compounds herein n is 2 and $R_1$ is

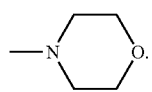

Some embodiments relate to compounds wherein n is 3 and $R_1$ is

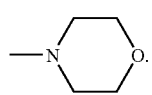

Some embodiments relate to compounds wherein n is 4 and $R_1$ is

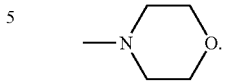

Some embodiments relate to compounds wherein n is 2.
Some embodiments relate to compounds wherein n is 3.
Some embodiments relate to compounds wherein n is 4.
Some embodiments relate to compounds wherein X is oxygen.
Some embodiments relate to compounds wherein X is nitrogen.
Some embodiments relate to compounds wherein $R_1$ is an unsymmetrical amine group.
Some embodiments relate to compounds wherein $R_1$ is

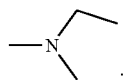

Some embodiments relate to compounds wherein $R_1$ is

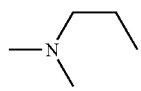

Some embodiments relate to compounds wherein n is 2 and $R_1$ is

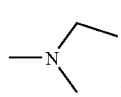

Some embodiments relate to compounds wherein n is 3 and $R_1$ is

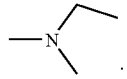

Some embodiments relate to compounds wherein n is 2.
Some embodiments relate to compounds wherein n is 3.
Some embodiments relate to compounds wherein n is 4.
Some embodiments relate to compounds wherein $R_1$ is

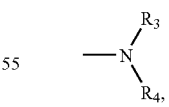

wherein $R_3$ is a propyl group and $R_4$ is a butyl group substituted with

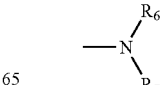

wherein $R_6$ is a methyl group and $R_7$ is an isobutyl group.

Some embodiments relate to compounds wherein $R_1$ is

wherein R3 is a $C_1$-$C_8$ linear alkyl and R4 is a branched $C_1$-$C_8$ alkyl substituted with —$OR_5$ wherein $R_5$ is selected from the group consisting of H, methyl, ethyl, propyl and butyl.

Some embodiments relate to compounds wherein $R_1$ is

wherein R3 is selected from the group consisting of methyl, ethyl, propyl and butyl and R4 is a branched $C_1$-$C_8$ alkyl substituted with —$SR_8$ wherein $R_8$ is selected from the group consisting of H, methyl, ethyl, propyl and butyl.

Other embodiments relate to a method of treating acute stress disorder; affective disorders, including depressive disorders (major depressive disorder, dysthymia, childhood depression, atypical depression, bipolar disorder, mania and hypomania) and anxiety disorders (generalized anxiety disorder, social anxiety disorder, phobias, obsessive compulsive disorder, panic disorder, post-traumatic stress disorder); premenstrual dysphoric disorder (also known as pre-menstrual syndrome); psychotic disorders, such as brief psychotic disorder, schizophrenia, psychotic mood disorder (depression and/or mania); attention deficit disorder (with and without hyperactivity); obesity, eating disorders such as anorexia nervosa and bulimia nervosa; vasomotor flushing; cocaine and alcohol addiction; sexual dysfunction and related illnesses; acute and chronic pain syndromes, as exemplified by fibromyalgia, arthritis, chronic low back pain, trigeminal neuralgia; visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome; neurologic disorders including seizure disorder, Tourette Syndrome, Parkinson's Disease, Huntington's Chorea, Alzheimer's Disease, subcortical and other dementias, Tardive Dyskinesia, Multiple Sclerosis, Rett Syndrome or amyotrophic lateral sclerosis comprising contacting a patient with an effective amount of a compound with the following structure:

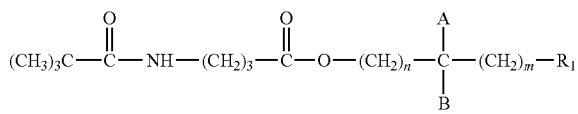

wherein, m is 0, 1, 2, 3 or 4;
wherein, n is 1, 2, 3, or 4;
wherein A and B are independently selected from H, $C_1$-$C_4$ alkyl;
wherein A and B may together represent a cyclic hydrocarbon moiety consisting of 2, 3, 4 or 5 methylene units;

and wherein
$R_1$ is selected from
a) the group consisting of,

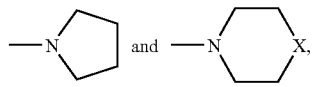

wherein X is selected from the group consisting of methylene ($CH_2$), unsubstituted or substituted nitrogen, oxygen, or sulfur or
  b) the group consisting of an unsymmetrical amine group of the formula

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

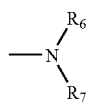

and —$SR_8$,
  wherein $R_5$, $R_6$, $R_7$ and $R_8$ are independently selected from H, a $C_1$-$C_8$ branched alkyl and a $C_1$-$C_8$ linear alkyl; and
  wherein $R_3$ and $R_4$ are not identical; and
  solvates, hydrates, salts, isomers, including pure enantiomers and diastereomers thereof and mixtures in any proportion thereof. It will be understood that any of the forgoing compounds can be in a crystalline or amorphous state or a mixture thereof.

In some embodiments, $R_1$ is

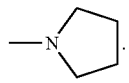

In some embodiments, $R_1$ is

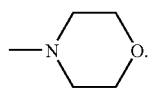

In some embodiments, $R_1$ is

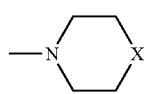

wherein X is selected from the group consisting of methylene ($CH_2$), unsubstituted or substituted nitrogen, oxygen, or sulfur.

In some embodiments, n is 2 and $R_1$ is

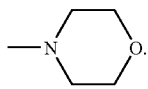

In some embodiments, n is 3 and $R_1$ is

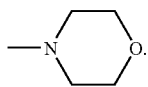

In some embodiments, n is 4 and $R_1$ is

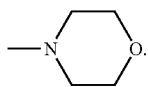

In some embodiments, n is 2.
In some embodiments, n is 3.
In some embodiments, n is 4.
In some embodiments, X is oxygen.
In some embodiments, X is nitrogen.
In some embodiments, $R_1$ is an unsymmetrical amine group.
In some embodiments, $R_1$ is

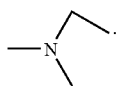

In some embodiments, $R_1$ is

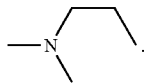

In some embodiments, n is 2 and $R_1$ is

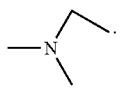

In some embodiments, n is 3 and $R_1$ is

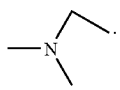

In some embodiments, n is 2.
In some embodiments, n is 3.
In some embodiments, n is 4.

In some embodiments, $R_1$ is

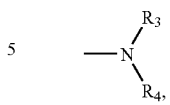

wherein $R_3$ is a propyl group and $R_4$ is a butyl group substituted with

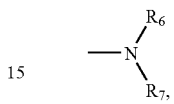

wherein $R_6$ is a methyl group and $R_7$ is an isobutyl group.
In some embodiments, $R_1$ is

wherein R3 is a $C_1$-$C_8$ linear alkyl and R4 is a branched $C_1$-$C_8$ alkyl substituted with —$OR_5$ wherein $R_5$ is selected from the group consisting of H, methyl, ethyl, propyl and butyl.
In some embodiments, $R_1$ is

wherein R3 is selected from the group consisting of methyl, ethyl, propyl and butyl and R4 is a branched $C_1$-$C_8$ alkyl substituted with —$SR_8$ wherein $R_8$ is selected from the group consisting of H, methyl, ethyl, propyl and butyl.
Other embodiments relate to a method of making a compound having the following structure:

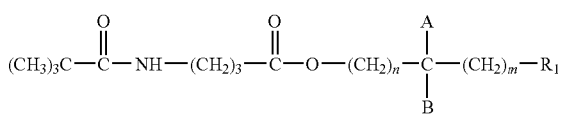

wherein, m is 0, 1, 2, 3 or 4;
wherein, n is 1, 2, 3, or 4;
wherein A and B are independently selected from H, $C_1$-$C_4$ alkyl;
wherein A and B may together represent a cyclic hydrocarbon moiety consisting of 2, 3, 4 or 5 methylene units;
and wherein
$R_1$ is selected from
a) the group consisting of,

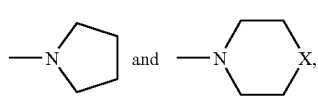

wherein X is selected from the group consisting of methylene ($CH_2$), unsubstituted or substituted nitrogen, oxygen, or sulfur or b) the group consisting of an unsymmetrical amine group of the formula

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

and —$SR_8$, wherein $R_5$, $R_6$, $R_7$ and $R_8$ are independently selected from H, a $C_1$-$C_8$ branched alkyl and a $C_1$-$C_8$ linear alkyl; and wherein $R_3$ and $R_4$ are not identical; and solvates, salts, hydrates, isomers, including pure enantiomers and diastereomers thereof and mixtures in any proportion thereof;

comprising performing a reaction reacting a compound with the following structure:

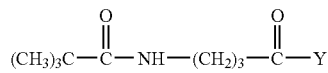

wherein Y is a leaving group, for example, fluorine, chlorine, bromine iodine, pyridine-2-thiol, trihalogenomethyloxy groups trichloromethoxy groups, alkanesulfonyloxy groups, methanesulfonyloxy groups, ethanesulfonyloxy groups, halogeno alkane sulfonyloxy groups, trifluoromethanesulfonyloxy groups pentafluoroethanesulfonyloxy groups, arylsulfonyloxy groups, benzenesulfonyloxy groups, p-toluenesulfonyloxy groups, p-nitrobenzenesulfonyloxy groups, O-tosyl groups, O-triflyl groups, O-mesyl groups, N-imidazolyl groups, N-triazolyl groups, N-benzotriazolyl groups, benzotriazolyloxy groups, imidazolyloxy groups, N-imidazolinone groups, N-imidazolone groups, N-imidazolinethione groups, N-succinimidyl groups, N-phthalimidyl groups, N-succinimidyloxy groups, N-phthalimidyloxy groups, 2-pyridyloxy groups, pentafluorophenyl groups, p-nitrophenol, 2,4-dinitrophenol, trichlorophenol, pentachlorophenol, 2-chloro-4,6-dimethoxytriazene, N-chlorosuccinimide, N-chloromaleic imide, N-chlorophthalimide, 1-hydroxy-1H-benzotriazole, 1-hydroxy-6-chloro-1H-benzotriazole, methoxycarbonyl groups, ethoxycarbonyl groups, isobutoxycarbonyl groups, trichloromethylcarbonyl groups, iso-but-2-ylcarbonyl groups and the like;

with the following structure:

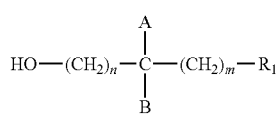

wherein, m is 0, 1, 2, 3 or 4;
wherein, n is 1, 2, 3, or 4;
wherein A and B are independently selected from H, $C_3$-$C_4$ alkyl;
wherein A and B may together represent a cyclic hydrocarbon moiety consisting of 2, 3, 4 or 5 methylene units;
and wherein
$R_1$ is selected from
a) the group consisting of,

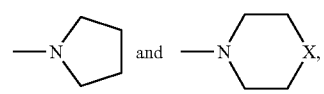

wherein X is selected from the group consisting of methylene ($CH_2$), unsubstituted or substituted nitrogen, oxygen, or sulfur or b) the group consisting of an unsymmetrical amine group of the formula

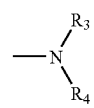

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

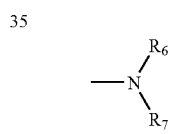

and —$SR_8$, wherein $R_5$, $R_6$, $R_7$ and $R_8$ are independently selected from H, a $C_1$-$C_8$ branched alkyl and a $C_1$-$C_8$ linear alkyl; and wherein $R_3$ and $R_4$ are not identical;

wherein when X=NH, protecting strategies such as those described herein are employed; and solvates, salts, hydrates, isomers, including pure enantiomers and diastereomers thereof and mixtures in any proportion thereof;

and yielding the compound.

In some embodiments, $R_1$ is

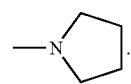

In some embodiments, $R_1$ is

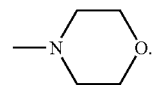

In some embodiments, $R_1$ is

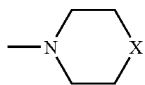

wherein X is selected from the group consisting of methylene ($CH_2$), unsubstituted or substituted nitrogen, oxygen, or sulfur.

In some embodiments, n is 2 and $R_1$ is

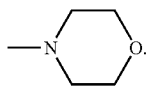

In some embodiments, n is 3 and $R_1$ is

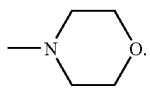

In some embodiments, n is 4 and $R_1$ is

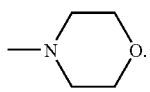

In some embodiments, n is 2.
In some embodiments, n is 3.
In some embodiments, n is 4.
In some embodiments, X is oxygen.
In some embodiments, X is nitrogen.
In some embodiments, $R_1$ is an unsymmetrical amine group.
In some embodiments, $R_1$ is

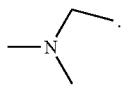

In some embodiments, $R_1$ is

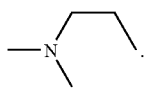

In some embodiments, n is 2 and $R_1$ is

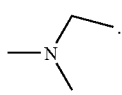

In some embodiments, n is 3 and $R_1$ is

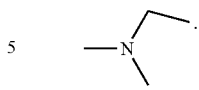

In some embodiments, n is 2.
In some embodiments, n is 3.
In some embodiments, n is 4.
In some embodiments, $R_1$ is

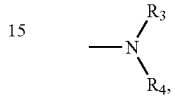

wherein $R_3$ is a propyl group and $R_4$ is a butyl group substituted with

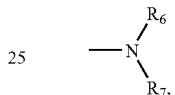

wherein $R_6$ is a methyl group and $R_7$ is an isobutyl group.

In some embodiments, $R_1$ is

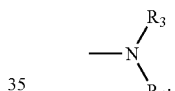

wherein R3 is a $C_1$-$C_8$ linear alkyl and R4 is a branched $C_1$-$C_8$ alkyl substituted with —$OR_5$ wherein $R_5$ is selected from the group consisting of H, methyl, ethyl, propyl and butyl.

In some embodiments, $R_1$ is

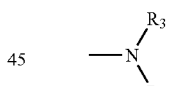

wherein R3 is selected from the group consisting of methyl, ethyl, propyl and butyl and R4 is a branched $C_1$-$C_8$ alkyl substituted with —$SR_8$ wherein $R_8$ is selected from the group consisting of H, methyl, ethyl, propyl and butyl.

Other embodiments relate to a pharmaceutical formulation comprising:

an effective amount of a compound with the following structure:

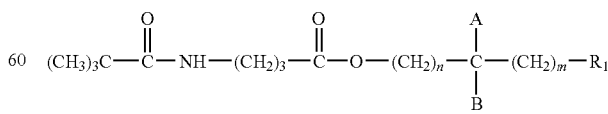

wherein, m is 0, 1, 2, 3 or 4;
wherein, n is 1, 2, 3, or 4;
wherein A and B are independently selected from H, $C_1$-$C_4$ alkyl;

wherein A and B may together represent a cyclic hydrocarbon moiety consisting of 2, 3, 4 or 5 methylene units;
and wherein
$R_1$ is selected from
a) the group consisting of,

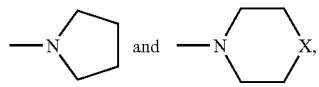

wherein X is selected from the group consisting of methylene ($CH_2$), unsubstituted or substituted nitrogen, oxygen, or sulfur or
b) the group consisting of an unsymmetrical amine group of the formula

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

and —$SR_8$,
wherein $R_5$, $R_6$, $R_7$ and $R_8$ are independently selected from H, a $C_1$-$C_8$ branched alkyl and a $C_1$-$C_8$ linear alkyl; and
wherein $R_3$ and $R_4$ are not identical; and
solvates, salts, hydrates, isomers, including pure enantiomers and diastereomers thereof and mixtures in any proportion thereof;
and a pharmaceutically acceptable carrier.
In some embodiments, $R_1$ is

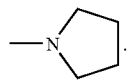

In some embodiments, $R_1$ is

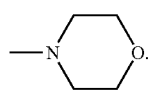

In some embodiments, $R_1$ is

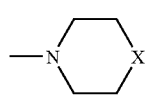

wherein X is selected from the group consisting of methylene ($CH_2$), unsubstituted or substituted nitrogen, oxygen, or sulfur.

In some embodiments, n is 2 and $R_1$ is

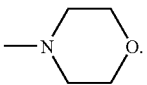

In some embodiments, n is 3 and $R_1$ is

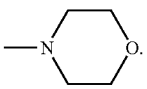

In some embodiments, n is 4 and $R_1$ is

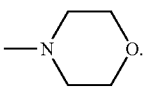

In some embodiments, n is 2.
In some embodiments, n is 3.
In some embodiments, n is 4.
In some embodiments, X is oxygen.
In some embodiments, X is nitrogen.
In some embodiments, $R_1$ is an unsymmetrical amine group.
In some embodiments, $R_1$ is

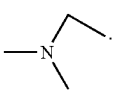

In some embodiments, $R_1$ is

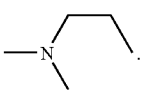

In some embodiments, n is 2 and $R_1$ is

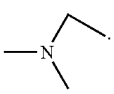

In some embodiments, n is 3 and $R_1$ is

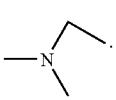

In some embodiments, n is 2.
In some embodiments, n is 3.
In some embodiments, n is 4.

In some embodiments, $R_1$ is

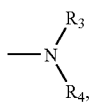

wherein $R_3$ is a propyl group and $R_4$ is a butyl group substituted with

wherein $R_6$ is a methyl group and $R_7$ is an isobutyl group.

In some embodiments, $R_1$ is

wherein R3 is a $C_1$-$C_8$ linear alkyl and R4 is a branched $C_1$-$C_8$ alkyl substituted with —$OR_5$ wherein $R_5$ is selected from the group consisting of H, methyl, ethyl, propyl and butyl.

In some embodiments, $R_1$ is

wherein R3 is selected from the group consisting of methyl, ethyl, propyl and butyl and R4 is a branched $C_1$-$C_8$ alkyl substituted with —$SR_8$ wherein $R_8$ is selected from the group consisting of H, methyl, ethyl, propyl and butyl.

In some embodiments, n is 1, m is 0, A is H, B is H and $R_1$ is

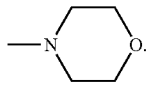

In some other embodiments, n is 2, m is 0, A is H, B is H and $R_1$ is

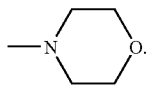

In still other embodiments, n is 3, m is 0, A is H, 13 is H and $R_1$ is

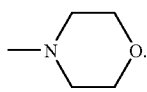

In yet other embodiments, n is 1, m is 0, A is H, B is H and $R_1$ is

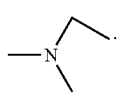

In some embodiments, n is 2, m is 0, A is H, B is H and $R_1$ is

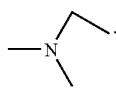

Some embodiments relate to a compound having the following structure:

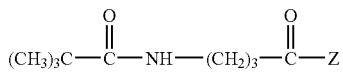

wherein Z is selected from

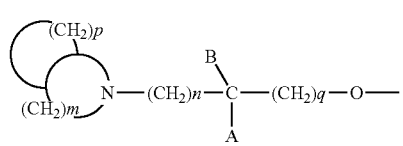 (I)

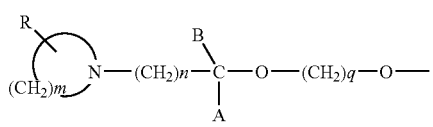 (II)

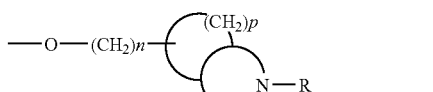 (III)

 (IV)

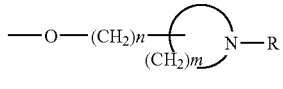 (V)

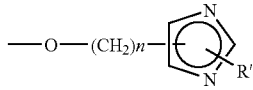 (VI)

wherein n, m, p and q are each independently selected from 0, 1, 2, 3 and 4, wherein j is selected from 1, 2 and 3, wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, $CONR_2$, alkoky, hydroxyalkyl, aryl, heteroaryl, arylalkyl and heteroarylalkyl groups; and solvates, hydrates, salts, isomers, including pure enantiomers and diastereomers thereof and mixtures in any proportion thereof. It will be understood that any of the forgoing compounds can be in a crystalline or amorphous state or a mixture thereof.

In some embodiments, Z is

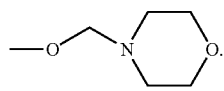

In some embodiments, Z is

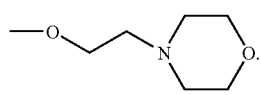

In some embodiments, Z is

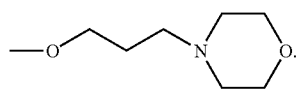

In some embodiments, Z is

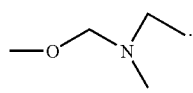

In some embodiments, Z is

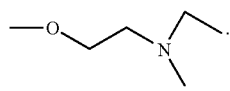

In some embodiments, Z is selected from:

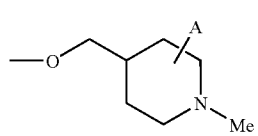

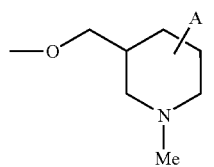

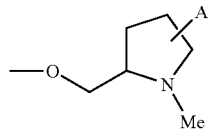

-continued

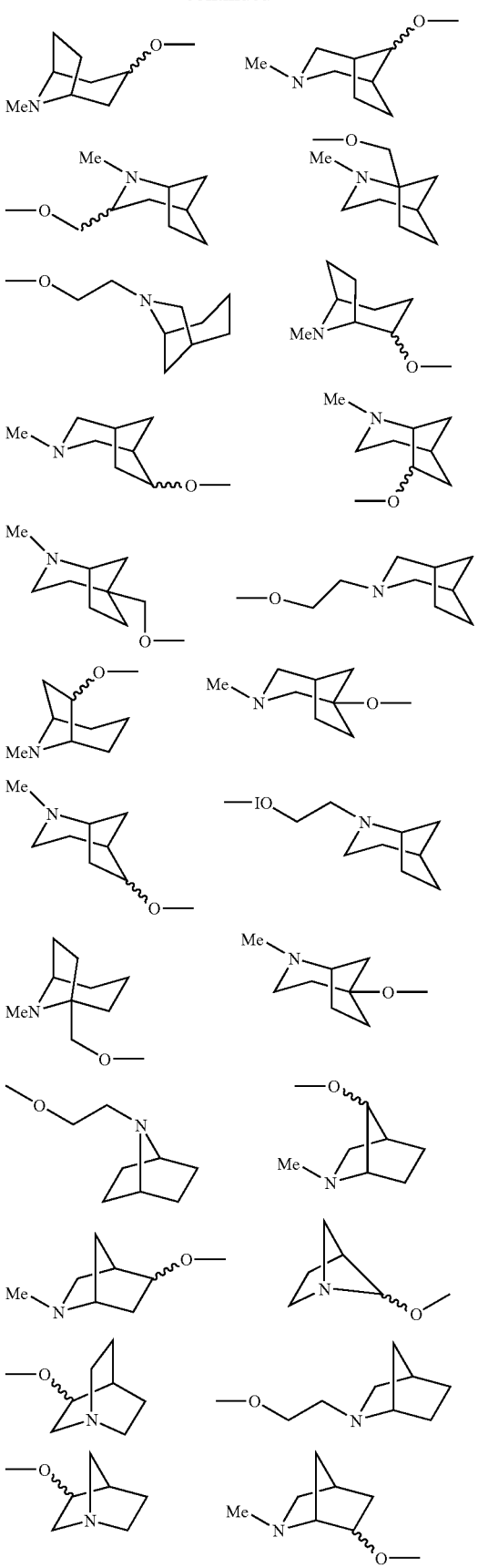

-continued
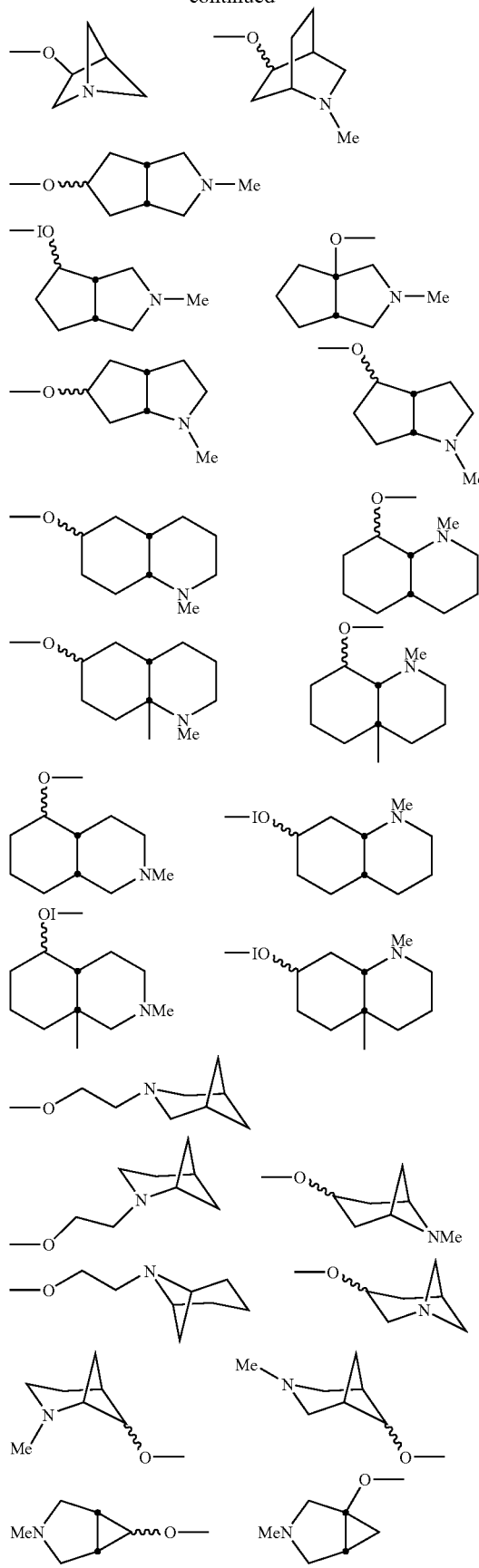
-continued
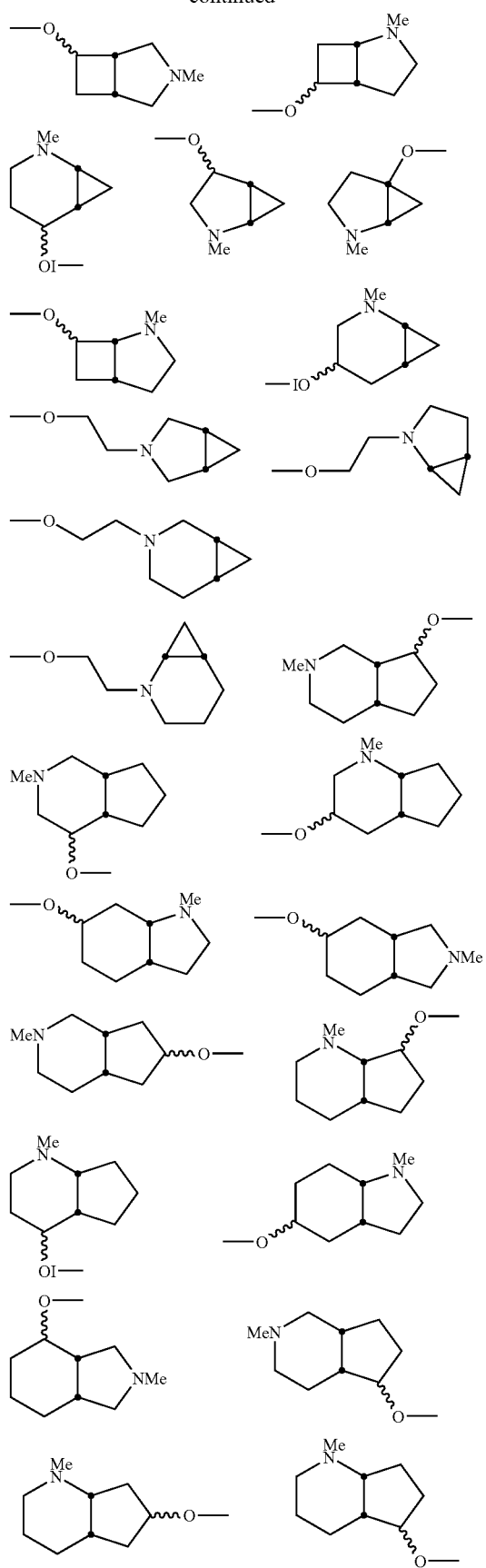

-continued

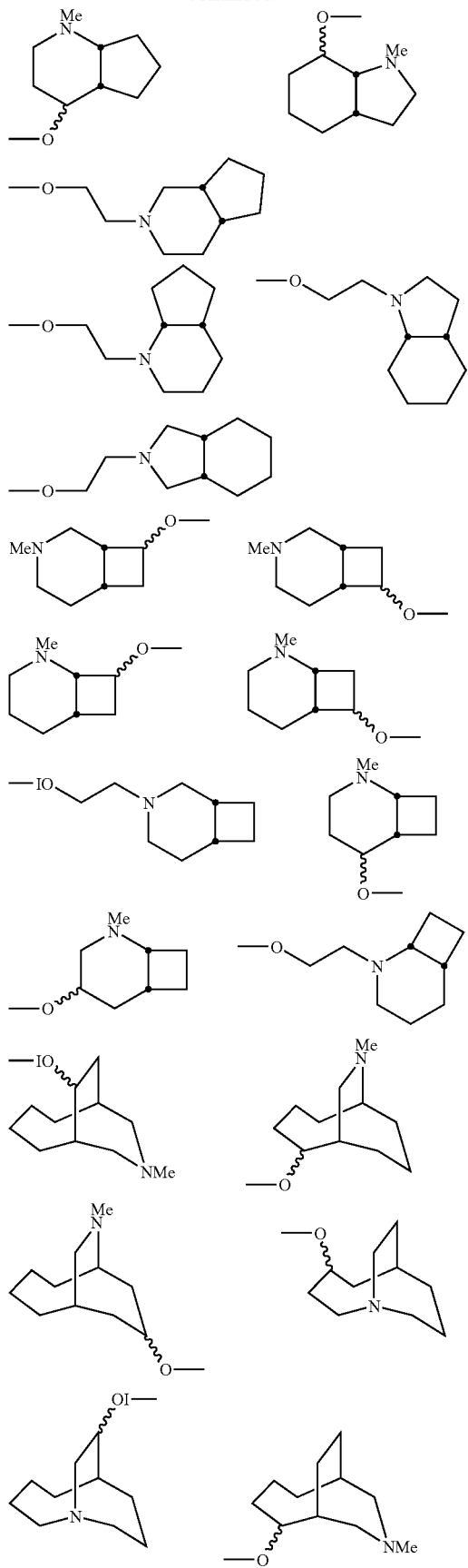

-continued

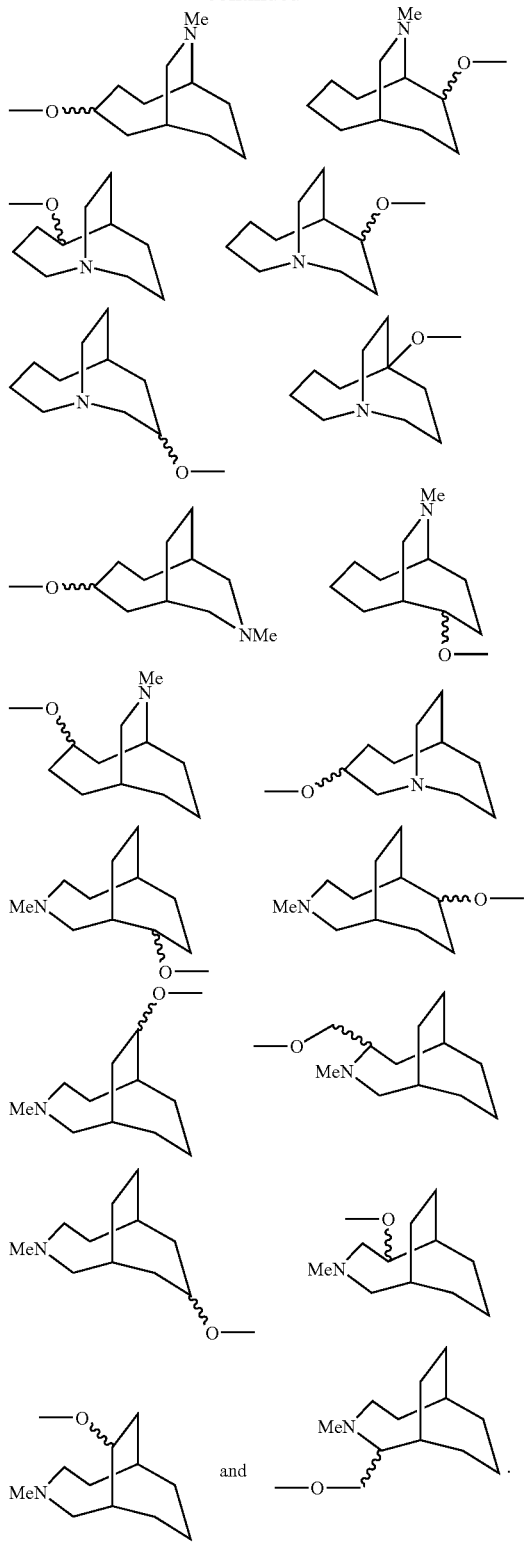

and

Some embodiments relate to a method of treating acute stress disorder; affective disorders, including depressive disorders (major depressive disorder, dysthymia, childhood depression, atypical depression, bipolar disorder, mania and hypomania) and anxiety disorders (generalized anxiety disorder, social anxiety disorder, phobias, obsessive compulsive disorder, panic disorder, post-traumatic stress disorder); premenstrual dysphoric disorder (also known as pre-menstrual syndrome); psychotic disorders, such as brief psychotic disorder, schizophrenia, psychotic mood disorder (depression and/or mania); attention deficit disorder (with and without hyperactivity); obesity, eating disorders such as anorexia nervosa and bulimia nervosa; vasomotor flushing; cocaine and alcohol addiction; sexual dysfunction and related illnesses; acute and chronic pain syndromes, as exemplified by fibromyalgia, arthritis, chronic low back pain, trigeminal neuralgia; visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome; neurologic disorders including seizure disorder, Tourette Syndrome, Parkinson's Disease, Huntington's Chorea, Alzheimer's Disease, subcortical and other dementias, Tardive Dyskinesia, Multiple Sclerosis, Rett Syndrome or amyotrophic lateral sclerosis comprising contacting a patient with an effective amount of a compound with the following structure:

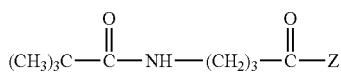

wherein Z is selected from

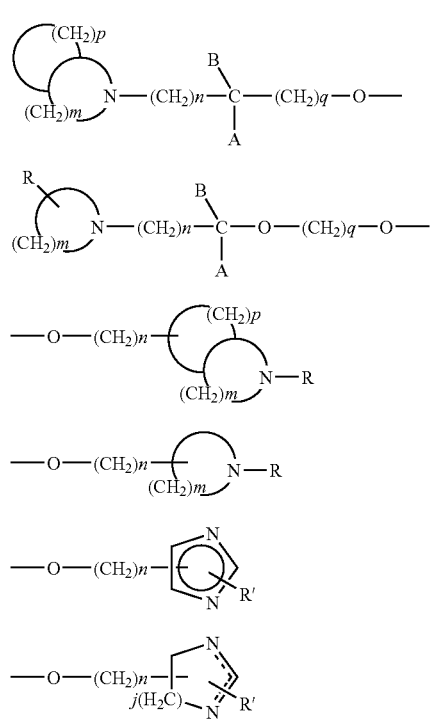

wherein n, m, p and q are each independently selected from 0, 1, 2, 3 an
wherein j is selected from 1, 2 and 3,
wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, $CONR_2$, alkoky, hydroxyalkyl, aryl, heteroaryl, arylalkyl and heteroarylalkyl groups; and solvates, hydrates, salts, isomers, including pure enantiomers and diastereomers thereof and mixtures in any proportion thereof. It will be understood that any of the forgoing compounds can be in a crystalline or amorphous state or a mixture thereof.

In some embodiments, Z is

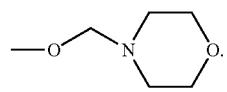

In some embodiments, Z is

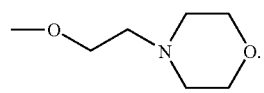

In some embodiments, Z is

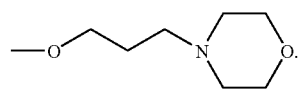

In some embodiments, Z is

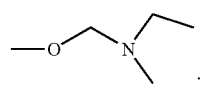

In some embodiments, Z is

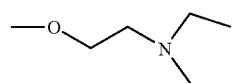

In some embodiments, Z is selected from:

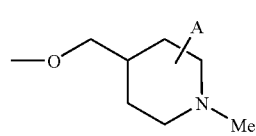 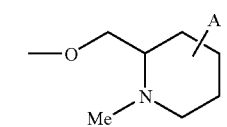

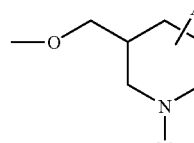 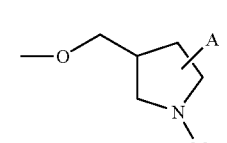

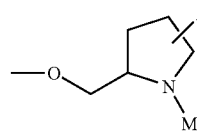 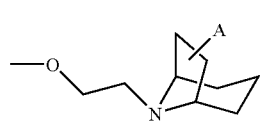

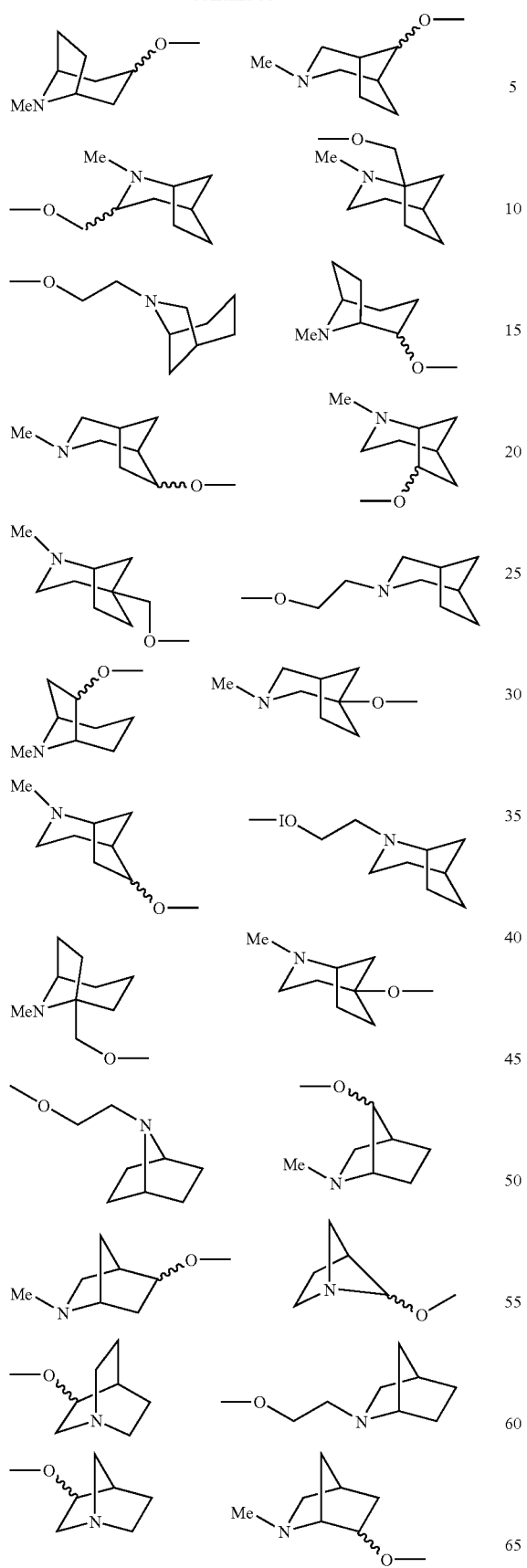
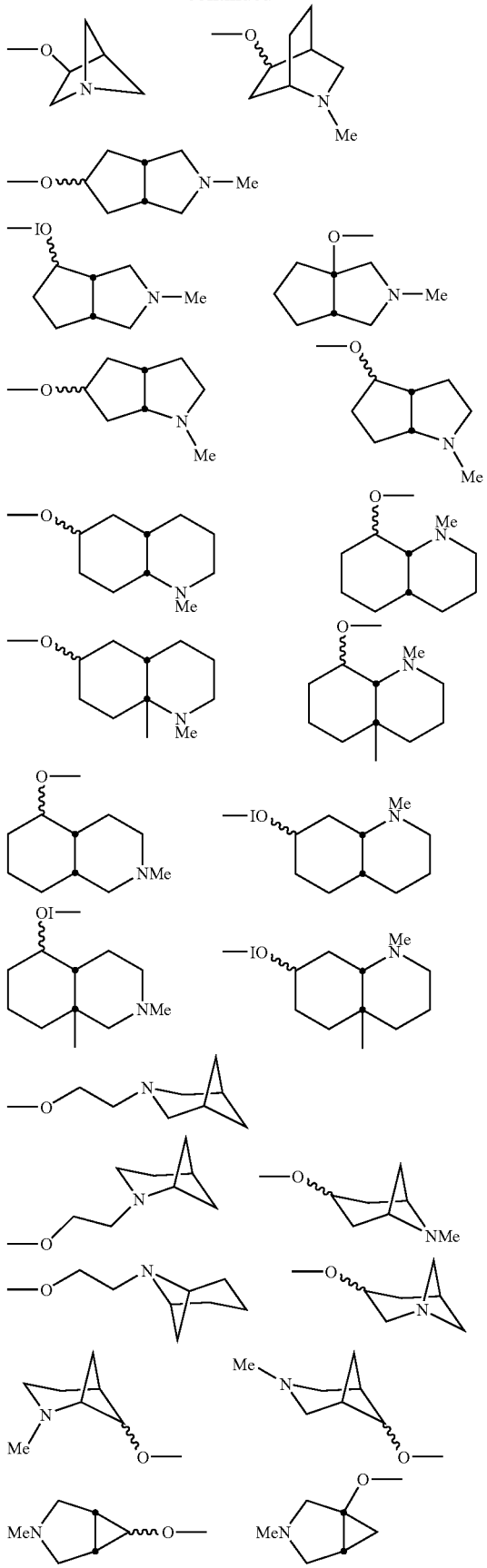

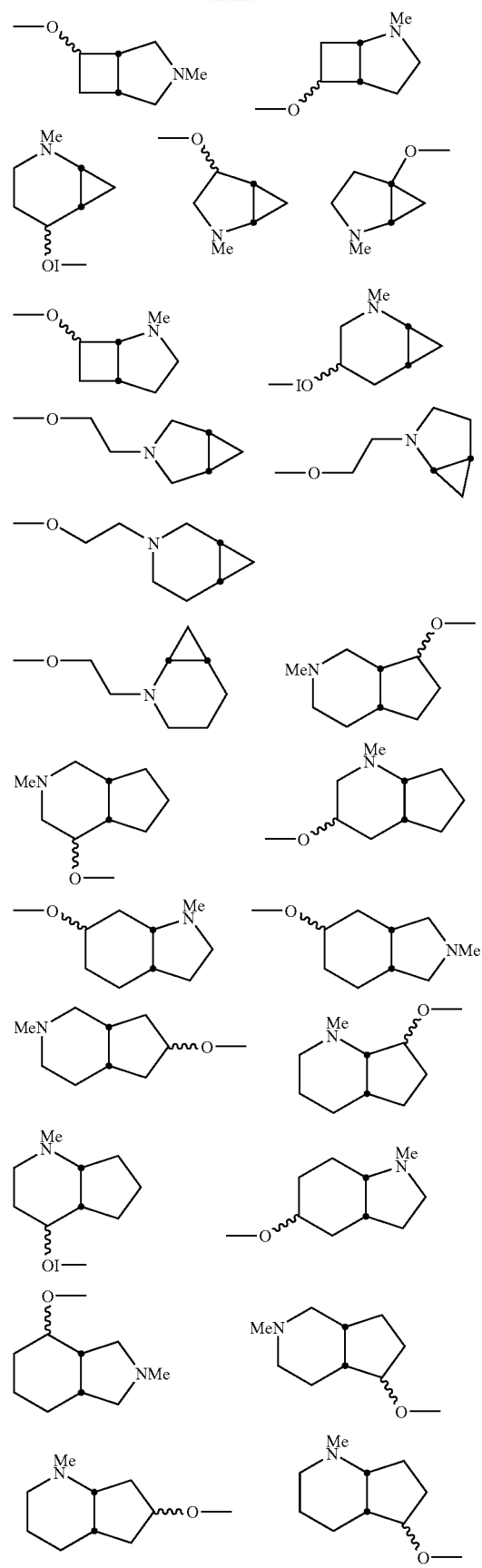
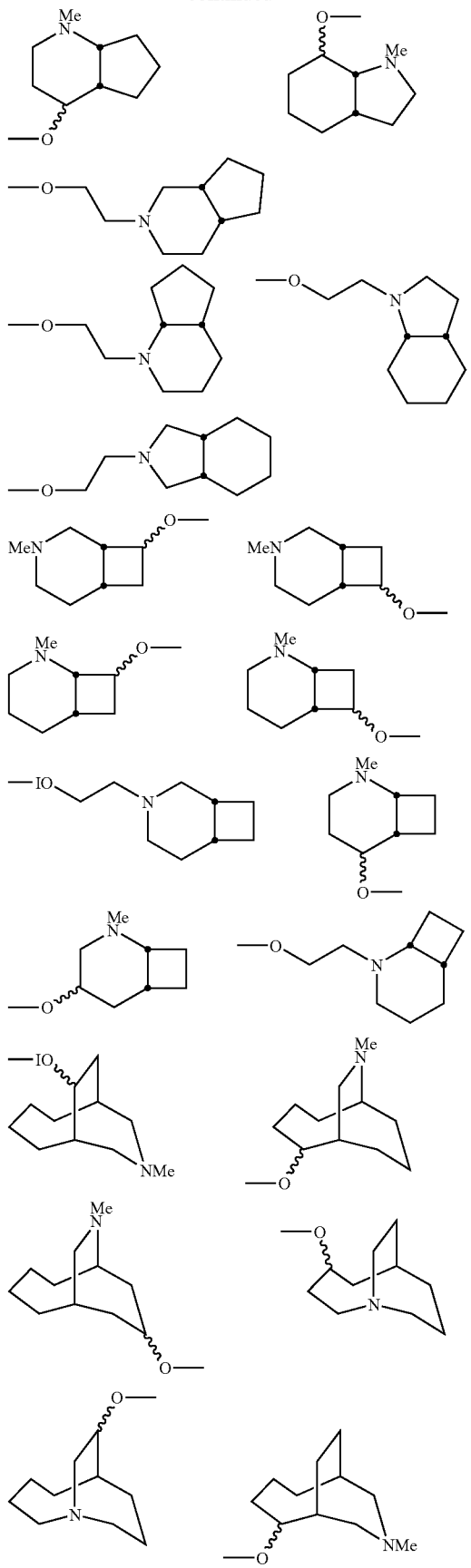

-continued

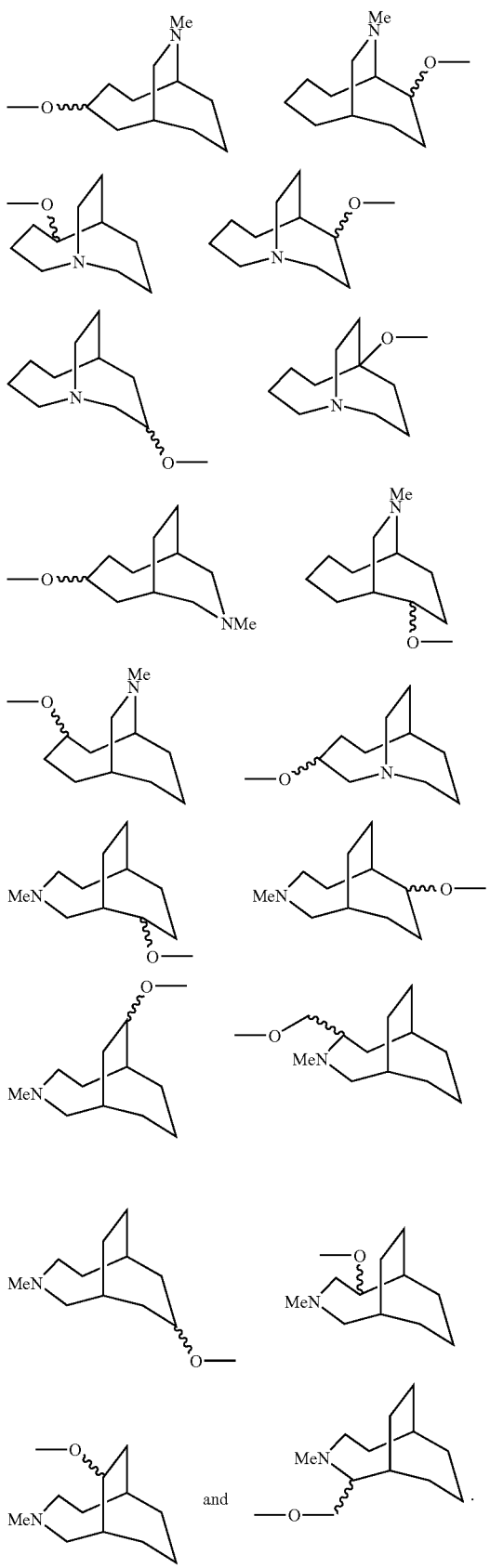

and

Some embodiments relate to a method of making a compound having the following structure:

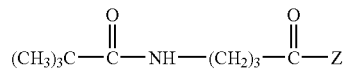

wherein Z is selected from

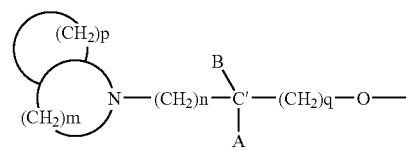

(I)

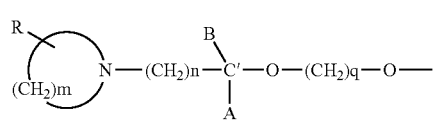

(II)

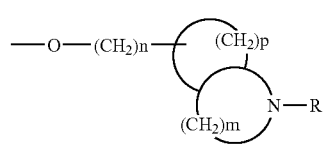

(III)

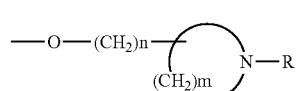

(IV)

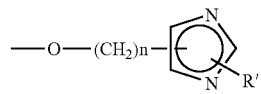

(V)

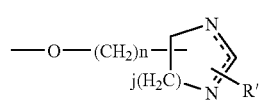

(VI)

wherein n, m, p and q are each independently selected from 0, 1, 2, 3 and wherein j is selected from 1, 2 and 3, wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, CONR$_2$, alkoky, hydroxyalkyl, aryl, heteroaryl, arylalkyl and heteroarylalkyl groups; and solvates, salts, hydrates, isomers, including pure enantiomers and diastereomers thereof and mixtures in any proportion thereof;

comprising performing a reaction reacting a compound with the following structure:

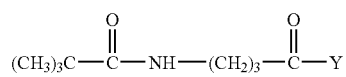

wherein Y is a leaving group selected from the group consisting of fluorine, chlorine, bromine iodine, pyridine-2-thiol, trihalogenomethyloxy groups trichloromethoxy groups, alkanesulfonyloxy groups, methanesulfonyloxy groups, ethanesulfonyloxy groups, halogeno alkane sulfonyloxy groups, trifluoromethanesulfonyloxy groups pentafluoroethanesulfonyloxy groups, arylsulfonyloxy groups, benzenesulfonyloxy groups, p-toluenesulfonyloxy groups, p-nitrobenzenesulfonyloxy groups, O-tosyl groups, O-triflyl groups, O-mesyl groups, N-imidazolyl groups, N-triazolyl groups, N-benzotriazolyl groups, benzotriazolyloxy groups, imidazolyloxy groups, N-imidazolinone groups, N-imidazolone groups, N-imidazolinethione groups, N-succinimidyl groups, N-phthalimidyl groups, N-succinimidyloxy groups, N-phthalimidyloxy groups, 2-pyridyloxy groups, pentafluorophenyl groups, p-nitrophenol, 2,4-dinitrophenol, trichlorophenol, pentachlorophenol, 2-chloro-4,6-dimethoxytriazene, N-chlorosuccinimide, N-chloromaleic imide, N-chlorophthalimide, 1-hydroxy-1H-benzotriazole, 1-hydroxy-6-chloro-1H-benzotriazole, methoxycarbonyl groups, ethoxycarbonyl groups, isobutoxycarbonyl groups, acid anhydride groups, mixed anhydride groups, trichloromethylcarbonyl groups, and iso-but-2-ylcarbonyl groups;

with the following structure:

HO—Z wherein Z is selected from (I) $\quad$ ![structure I]

(II) $\quad$ ![structure II]

(III) $\quad$ ![structure III]

(IV) $\quad$ ![structure IV]

(V) $\quad$ ![structure V]

(VI) $\quad$ ![structure VI]

wherein n, m, p and q are each independently selected from 0, 1, 2, 3 and 4, wherein j is selected from 1, 2 and 3, wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, $CONR_2$, alkoky, hydroxyalkyl, aryl, heteroaryl, arylalkyl and heteroarylalkyl groups; and solvates, salts, hydrates, isomers, including pure enantiomers and diastereomers thereof and mixtures in any proportion thereof.

and yielding the compound.

In some embodiments, Z is

—O—CH₂—N(morpholine).

In some embodiments, Z is

—O—CH₂CH₂—N(morpholine).

In some embodiments, Z is

—O—(CH₂)₃—N(morpholine).

In some embodiments, Z is

—O—CH₂—NEt(Me).

In some embodiments, Z is

—O—CH₂CH₂—NEt(Me).

In some embodiments, Z is selected from:

[structures of N-methyl piperidinyl, pyrrolidinyl, tropane and related bicyclic amine-containing Z groups]

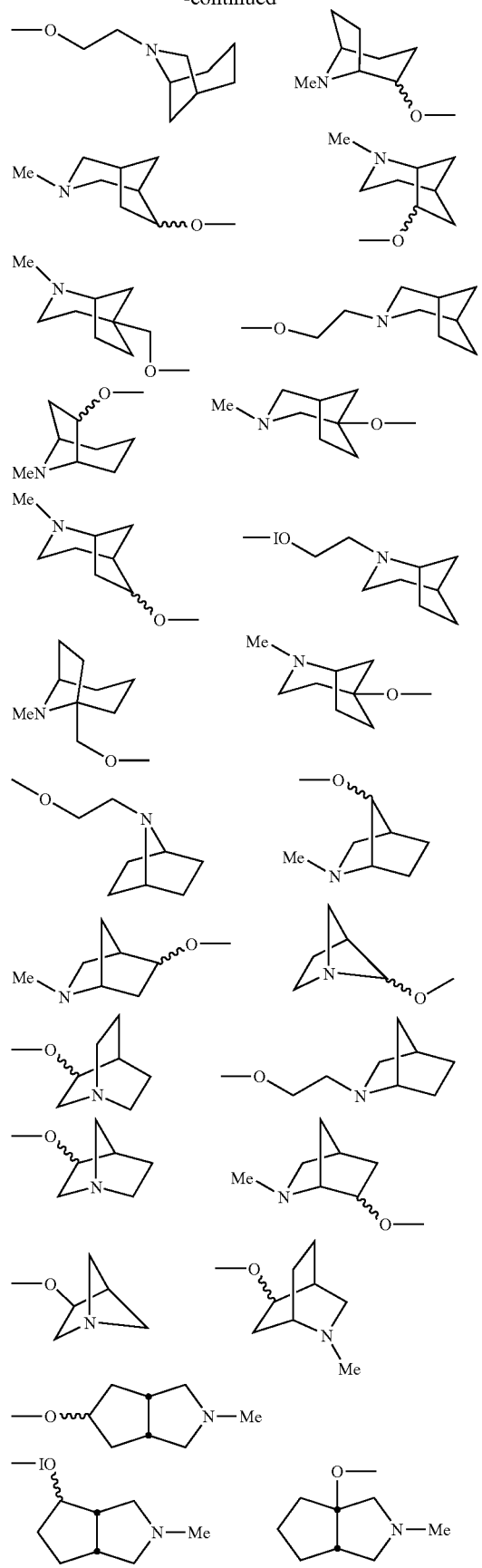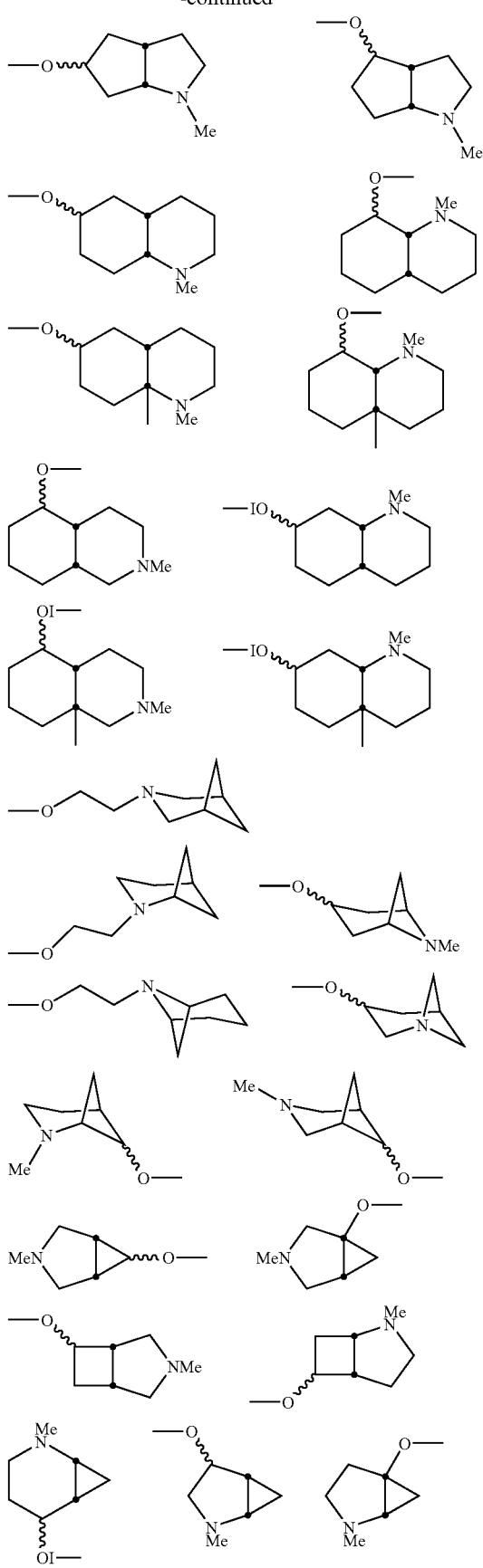

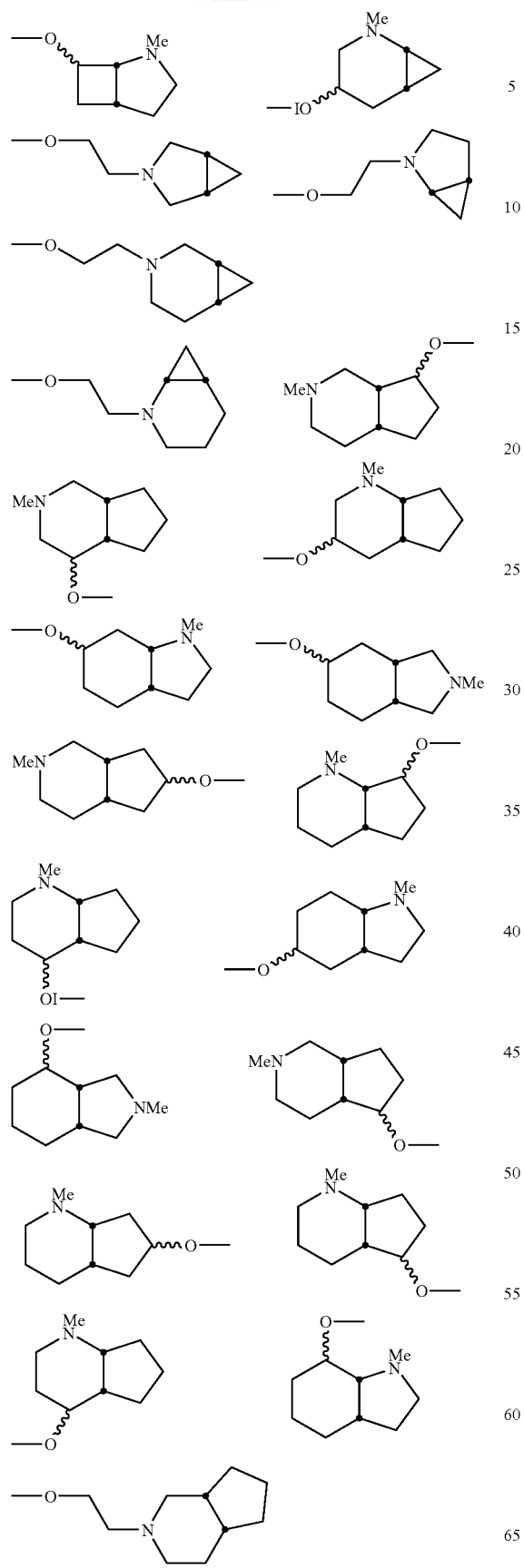
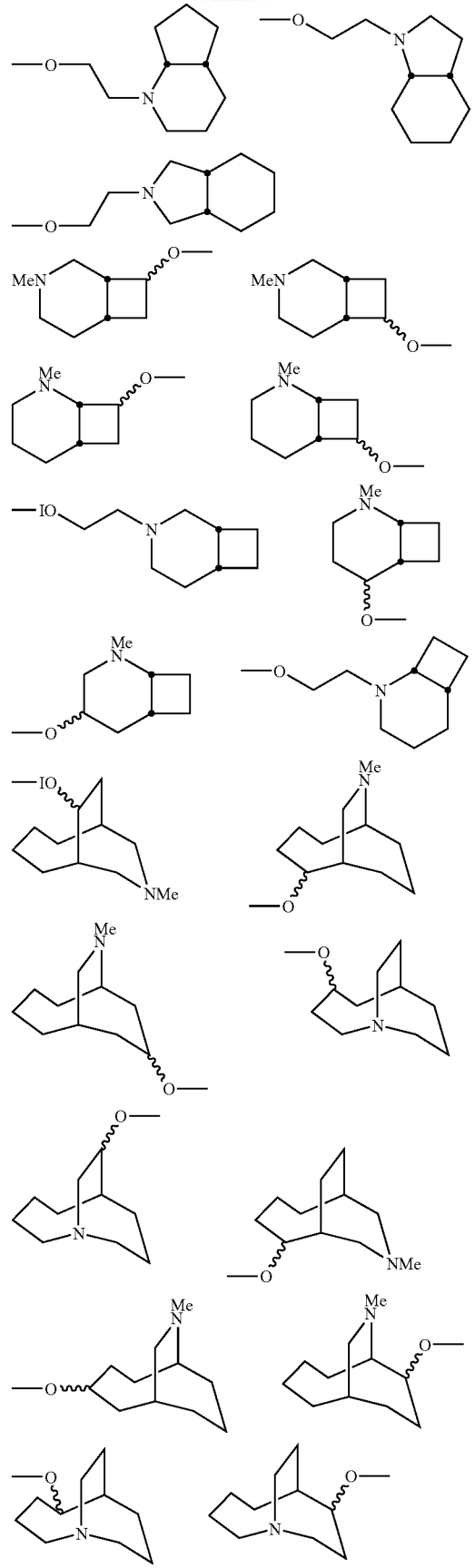

37
-continued

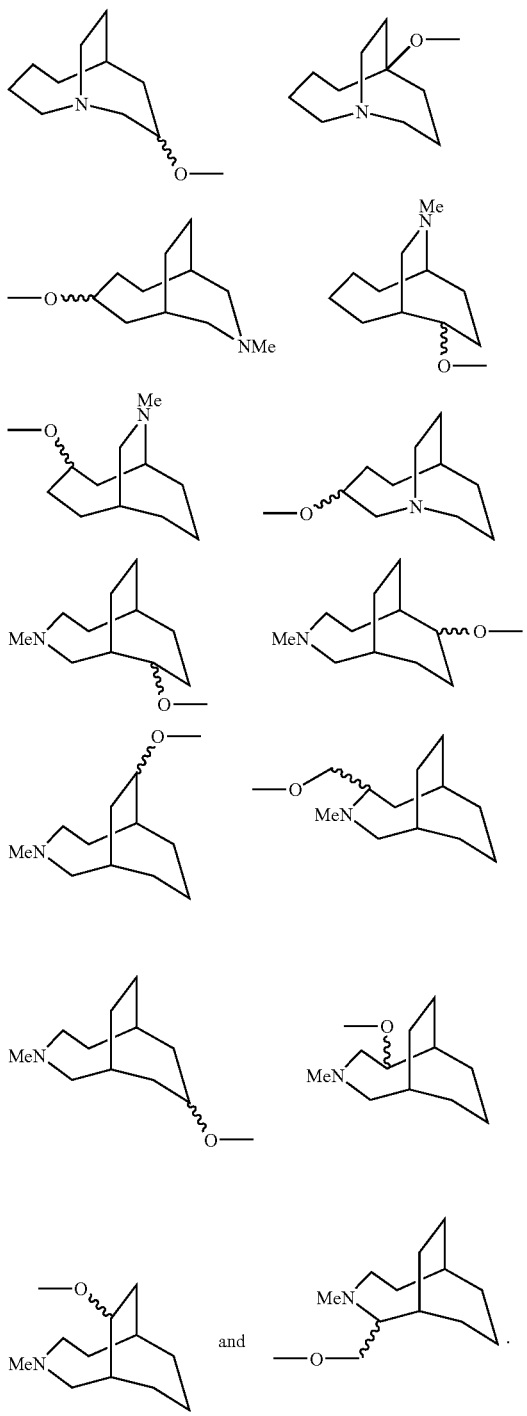

Some embodiments relate to a pharmaceutical formulation comprising:

an effective amount of a compound with the following structure:

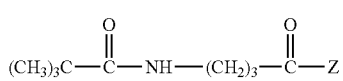

38 wherein Z is selected from

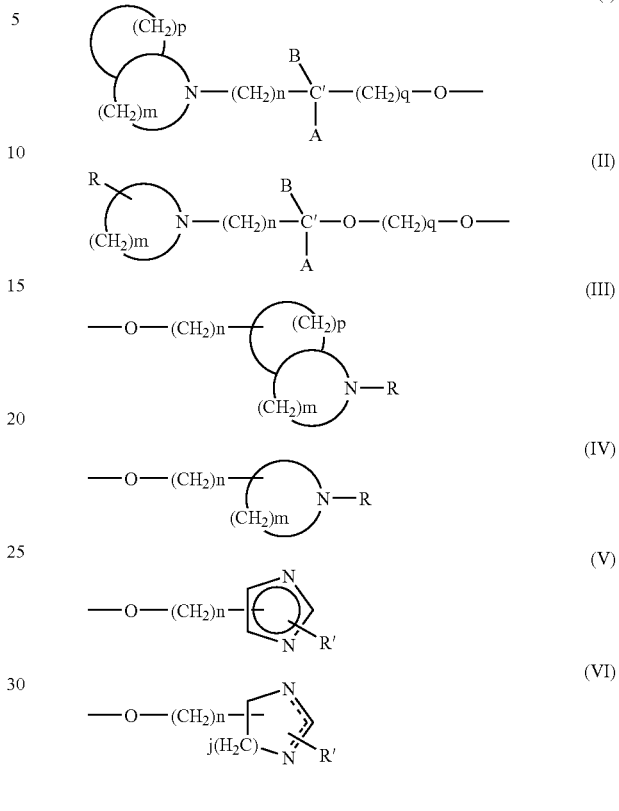

wherein n, m, p and q are each independently selected from 0, 1, 2, 3 and wherein j is selected from 1, 2 and 3, wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, $CONR_2$, alkoky, hydroxyalkyl, aryl, heteroaryl, arylalkyl and heteroarylalkyl groups; and solvates, salts, hydrates, isomers, including pure enantiomers and diastereomers thereof and mixtures in any proportion thereof;

and a pharmaceutically acceptable carrier.

In some embodiments, Z is

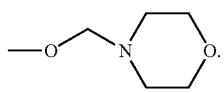

In some embodiments, Z is

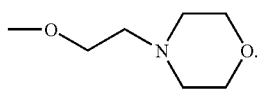

In some embodiments, Z is
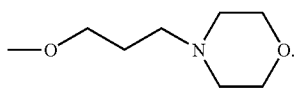
In some embodiments, Z is
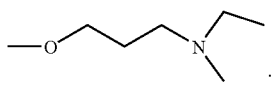
In some embodiments, Z is
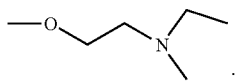
In some embodiments, Z is selected from:
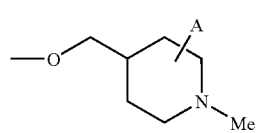 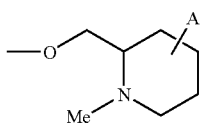
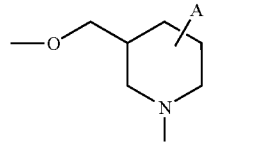 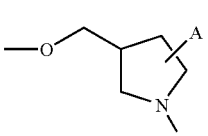
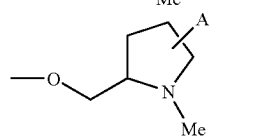 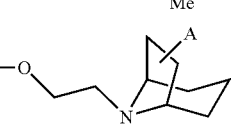
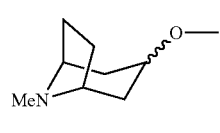 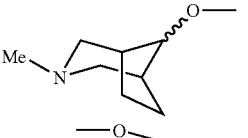
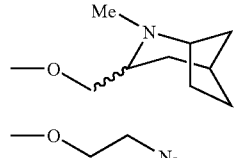 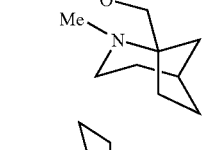
 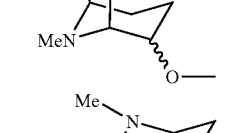
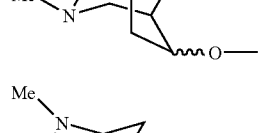 
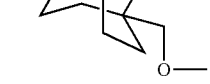 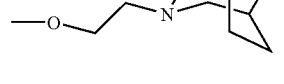
-continued
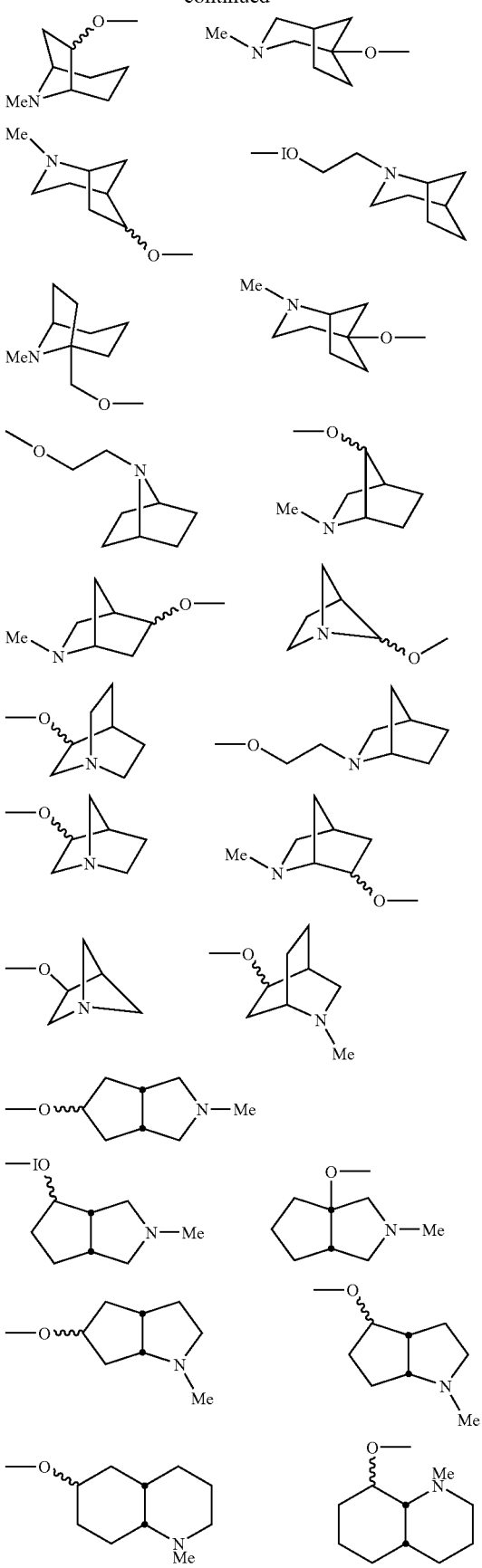

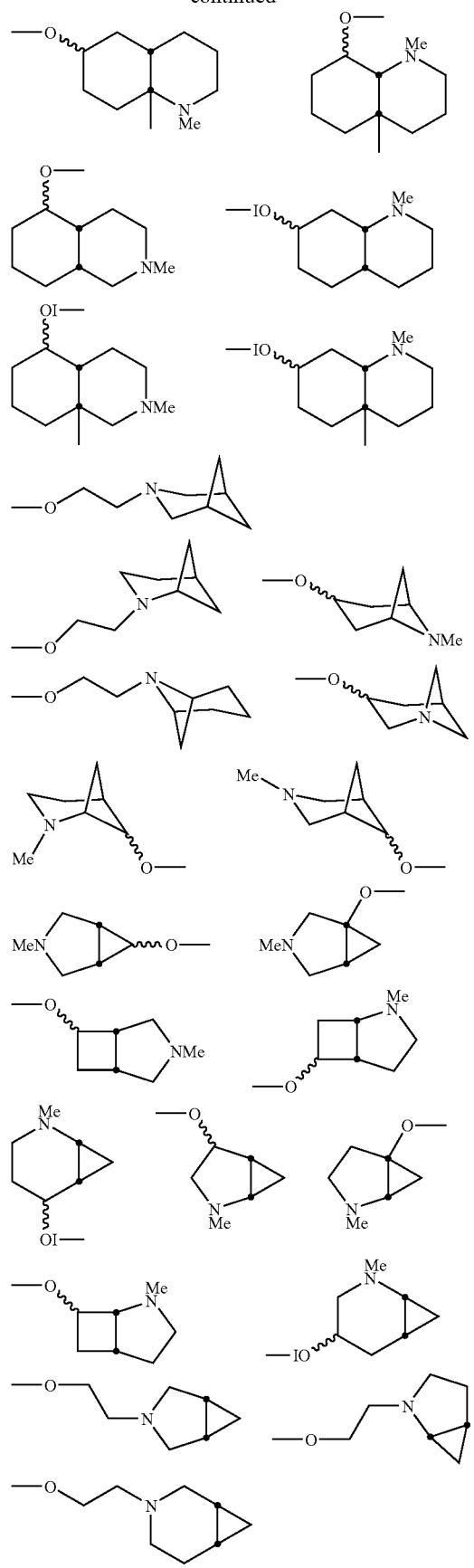
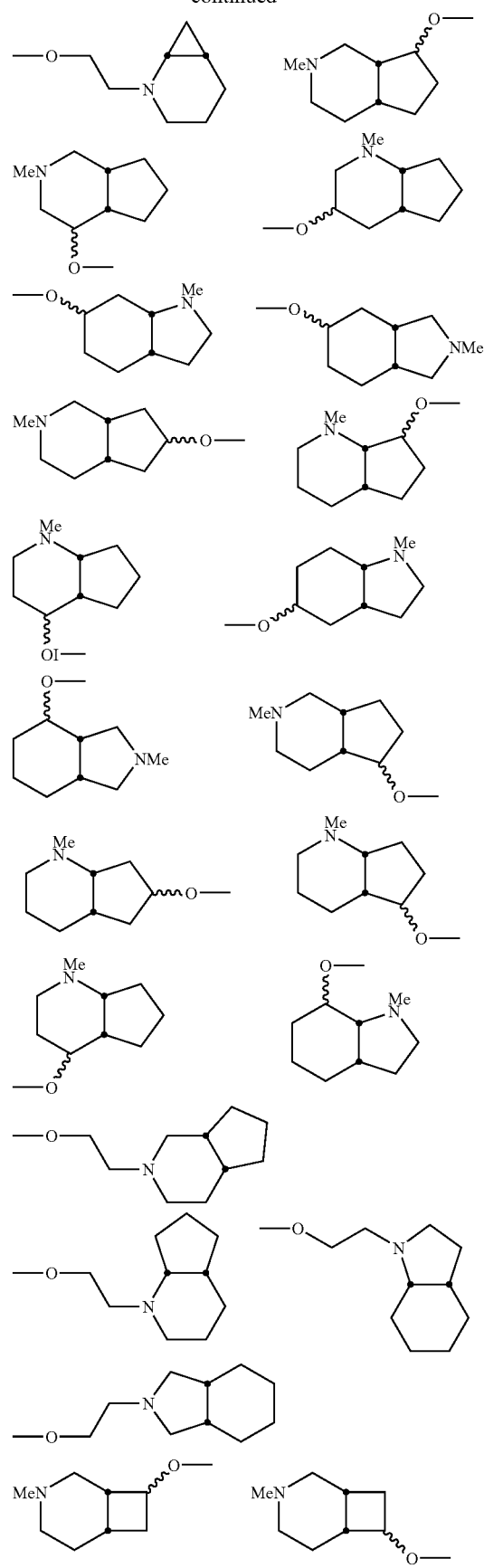

-continued

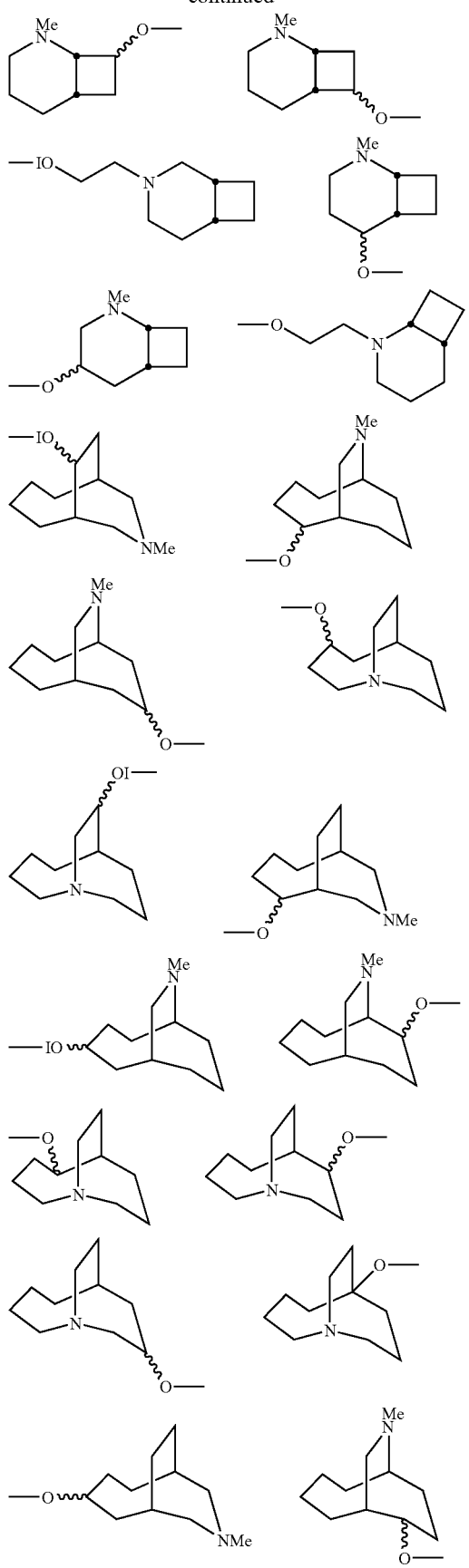
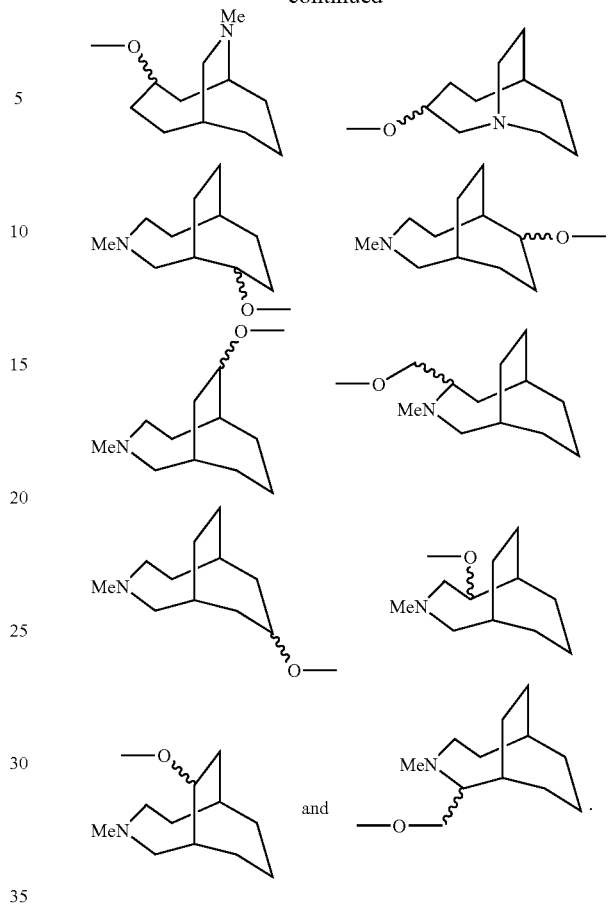

DETAILED DESCRIPTION OF THE INVENTION

Figure 1:
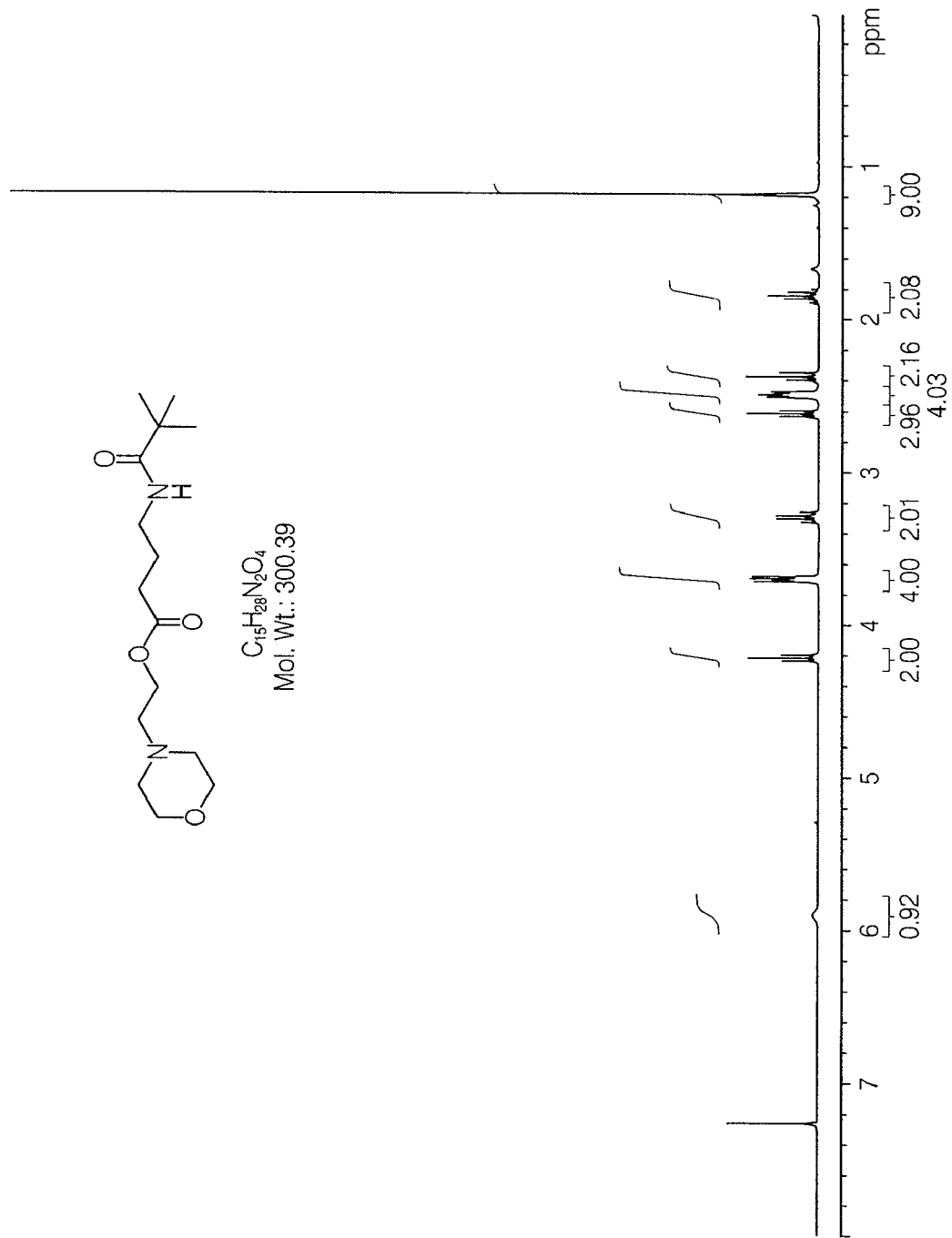
FIG. 1 is a proton NMR spectrum of a compound according to an embodiment shown in EXAMPLE 1 below.
Figure 2:
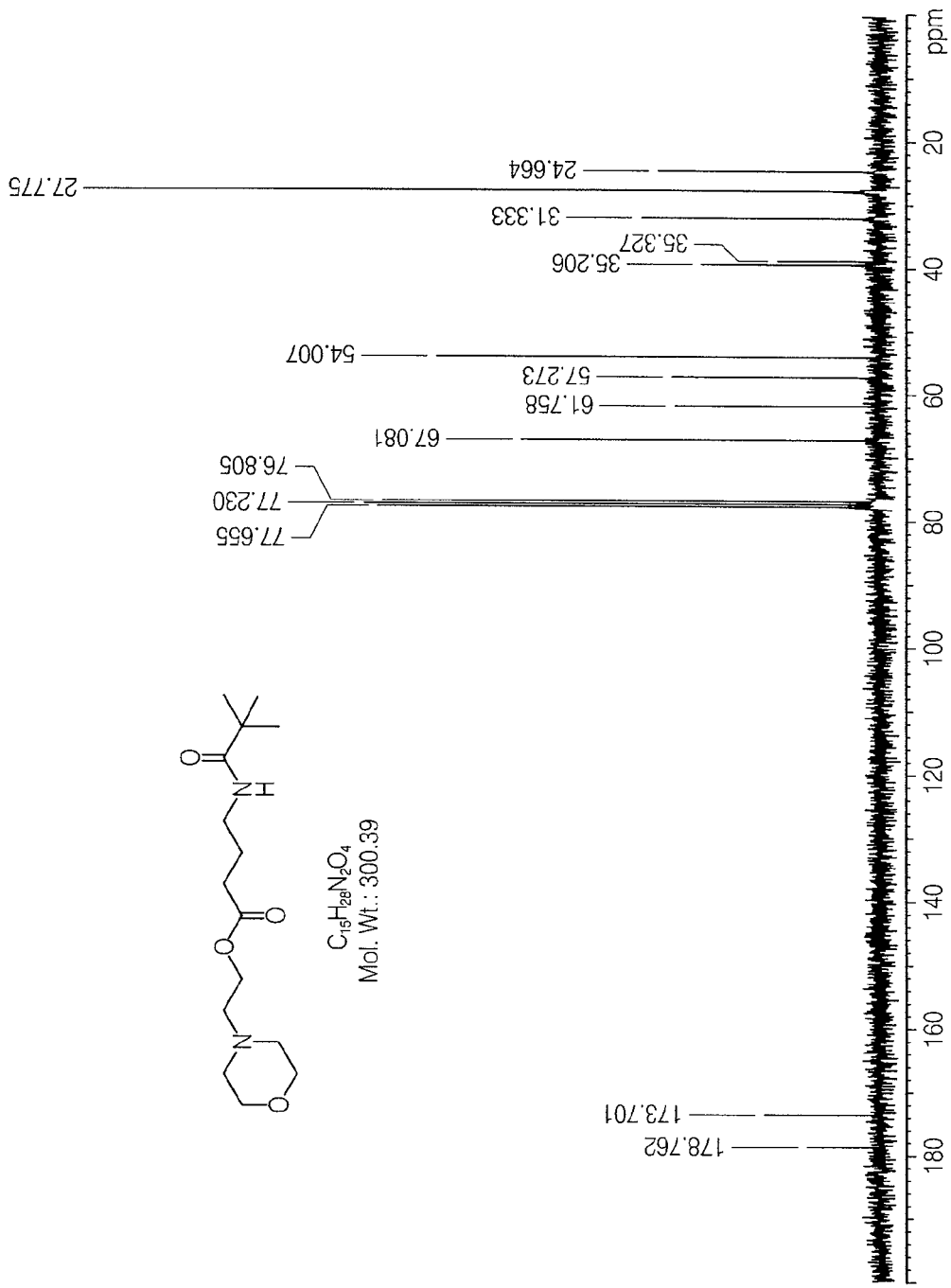
FIG. 2 is a $^{13}$C NMR spectrum of a compound according to an embodiment shown in EXAMPLE 1 below.
Figure 3:
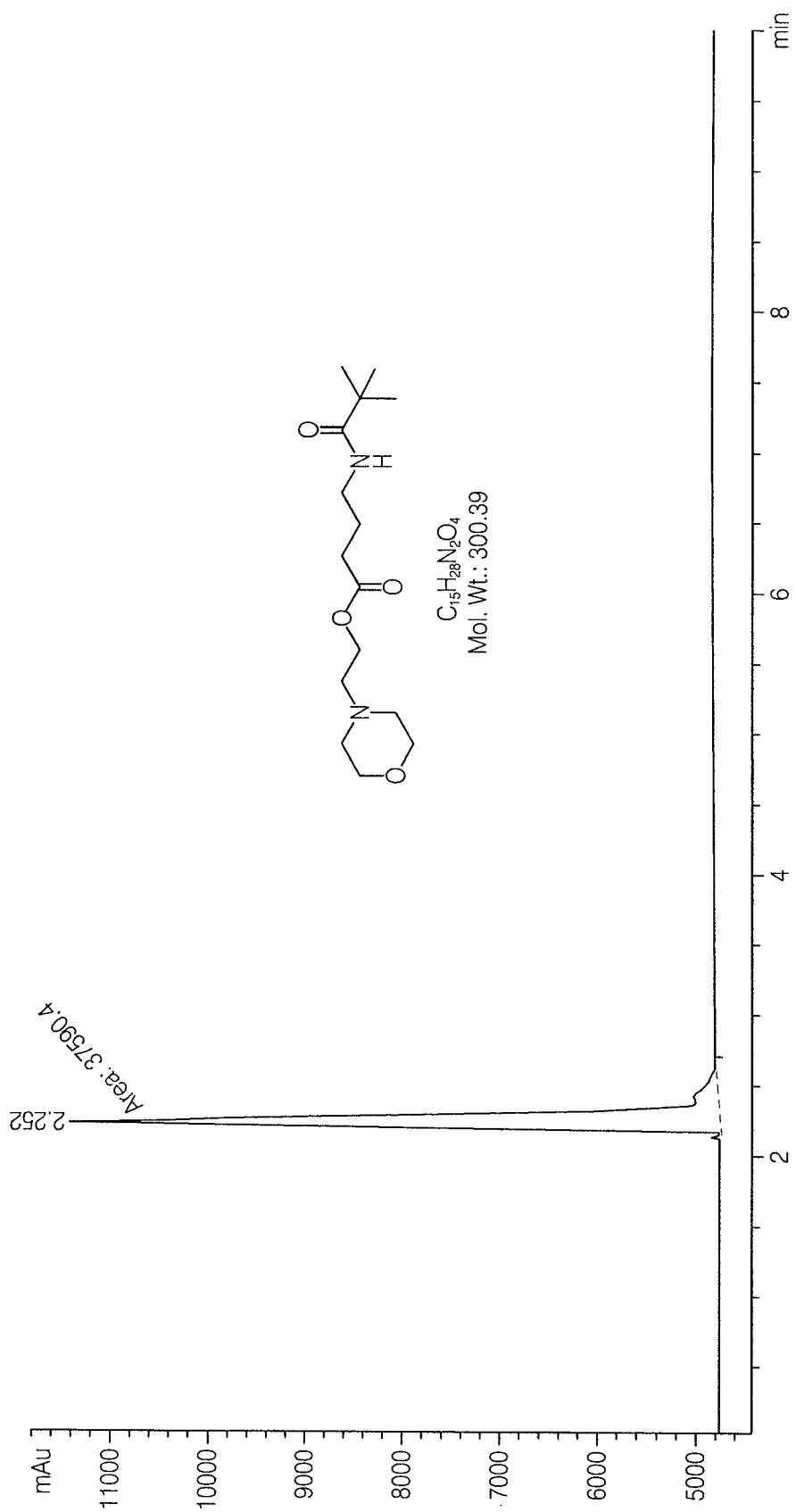
FIG. 3 is an HPLC chromatogram of a compound according to an embodiment shown in EXAMPLE 1 below.
Figure 4:
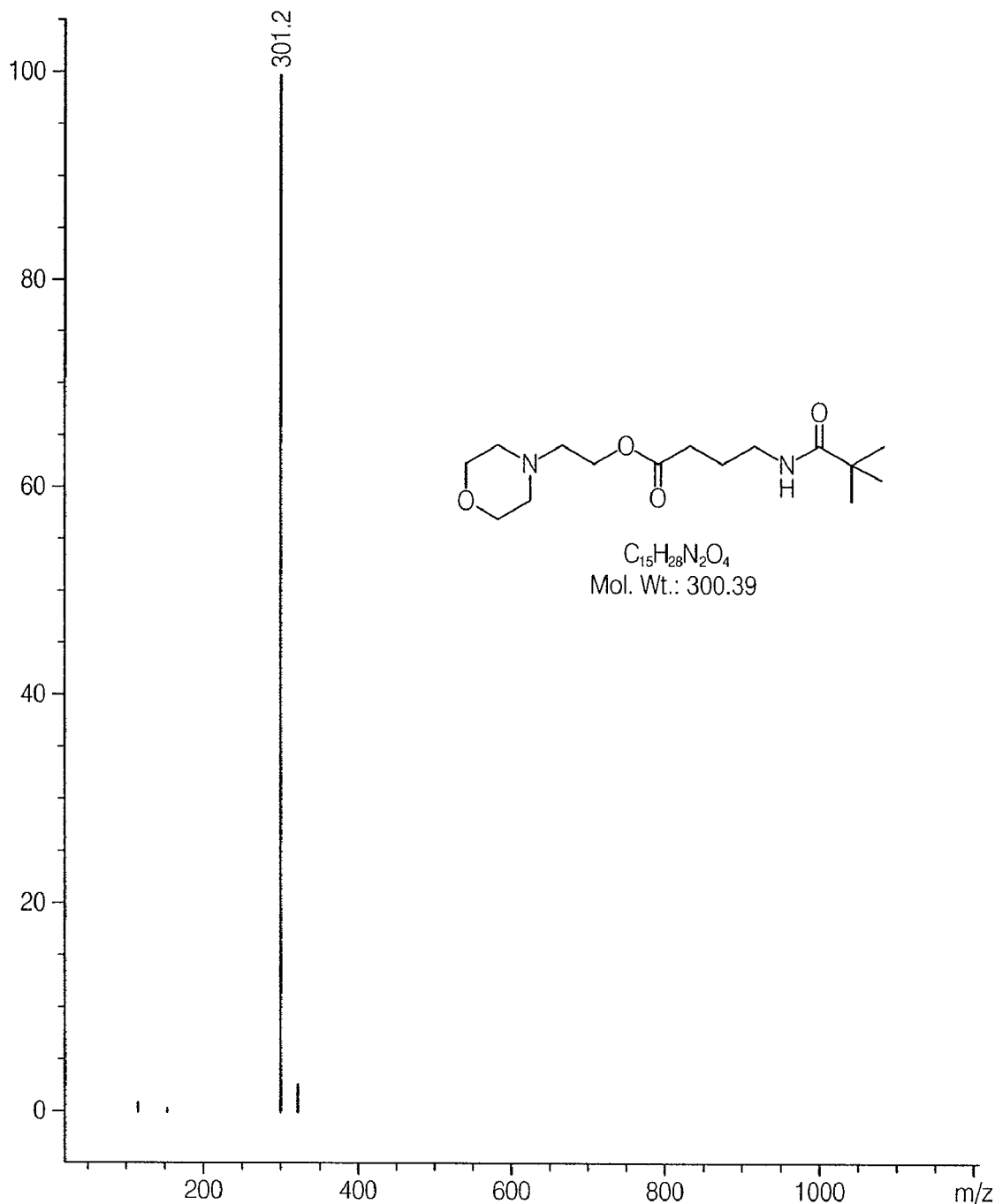
FIG. 4 is a mass spectrum of a compound according to an embodiment shown in EXAMPLE 1 below.
Figure 5:
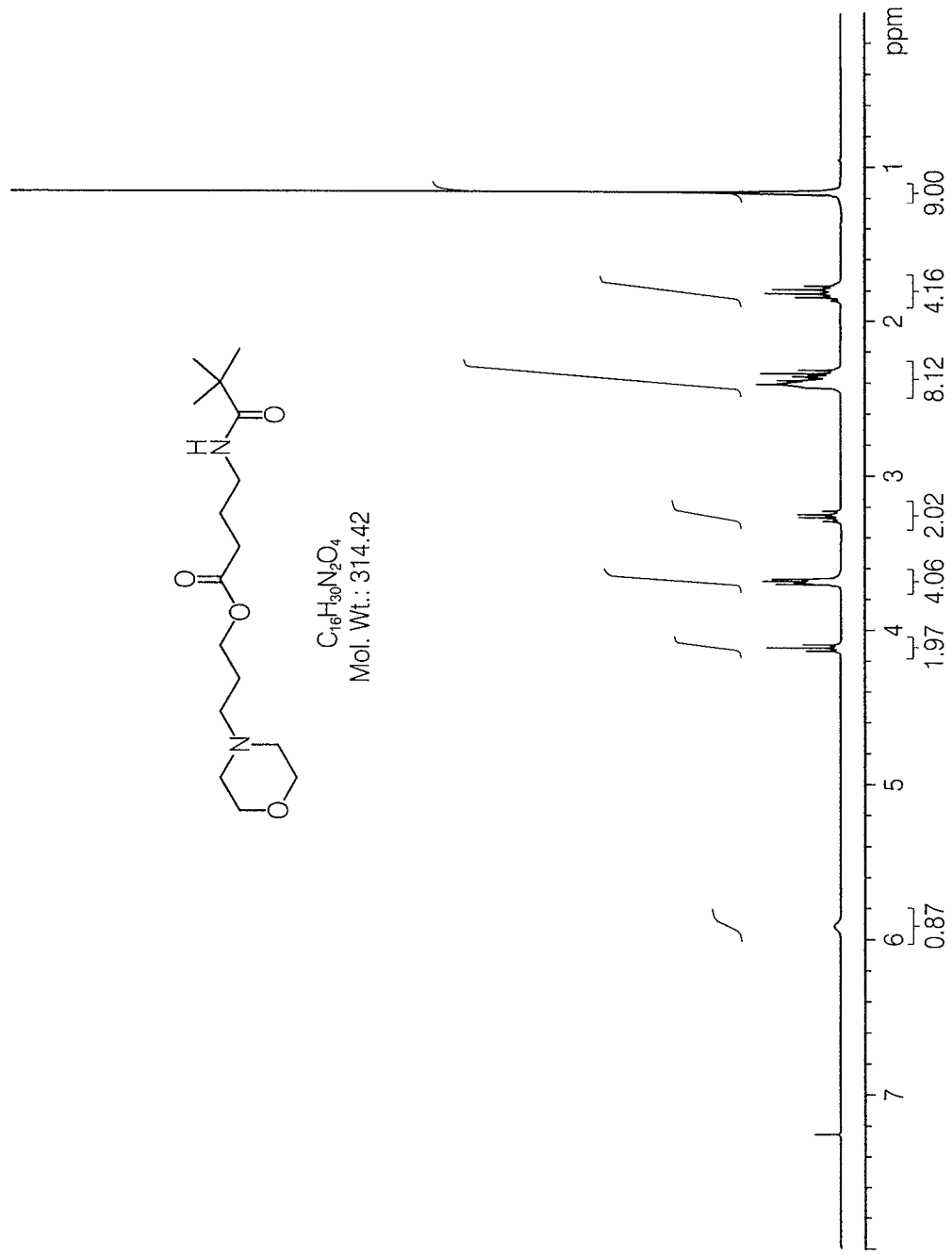
FIG. 5 is a proton NMR spectrum of a compound according to an embodiment shown in EXAMPLE 2 below.
Figure 6:
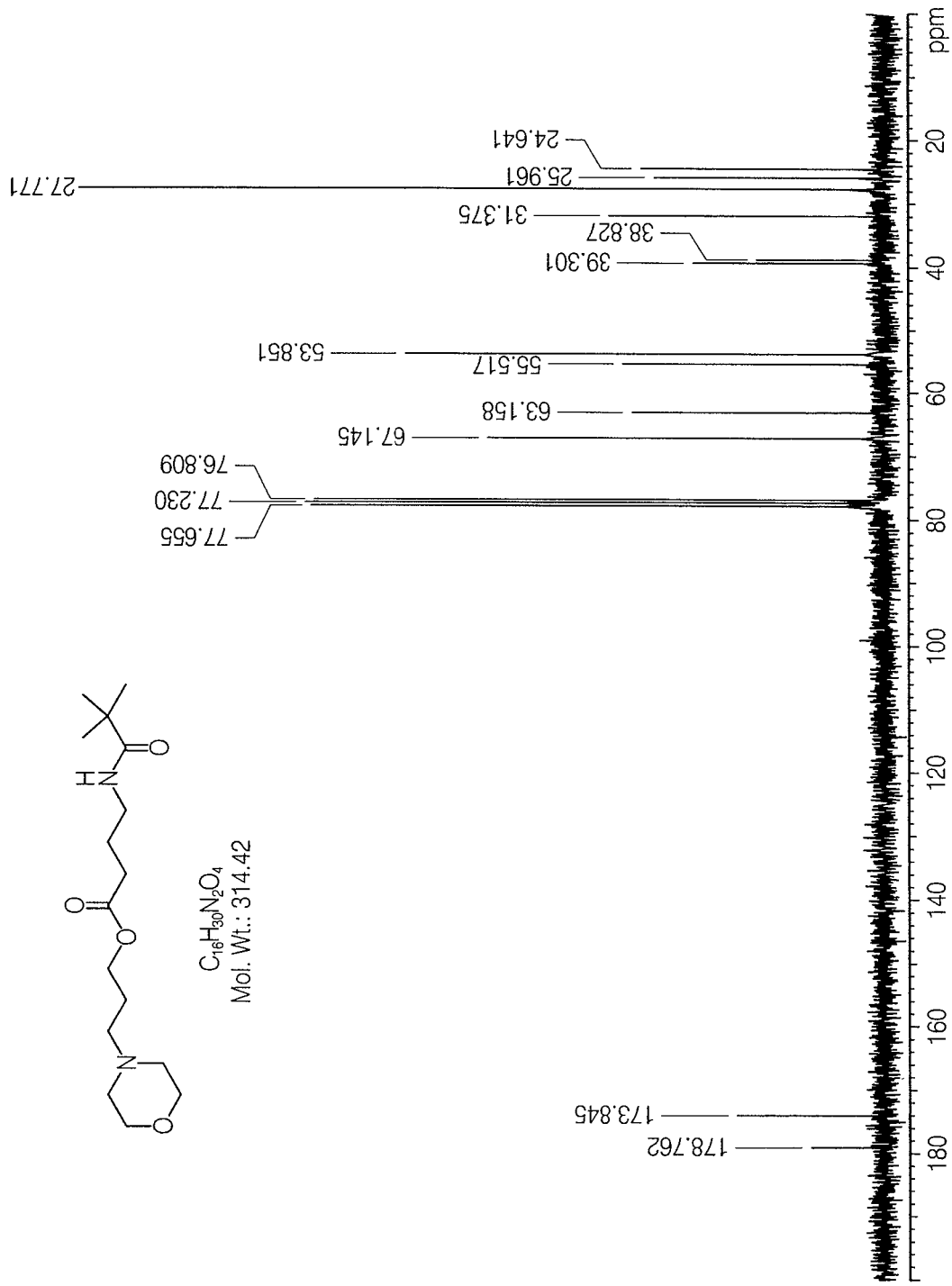
FIG. 6 is a $^{13}$C NMR spectrum of a compound according to an embodiment shown in EXAMPLE 2 below.
Figure 7:
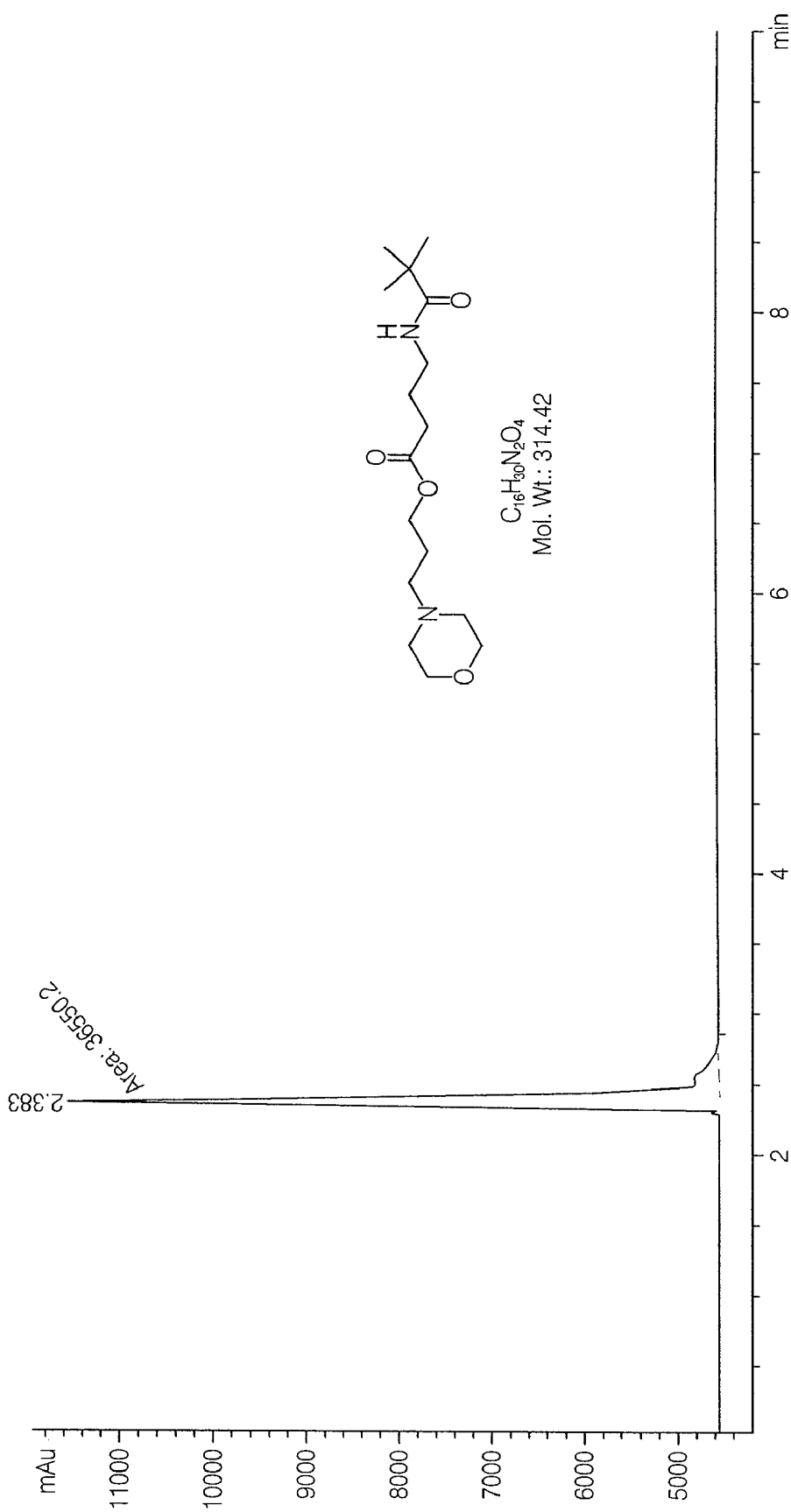
FIG. 7 is an HPLC chromatogram of a compound according to an embodiment shown in EXAMPLE 2 below.
Figure 8:
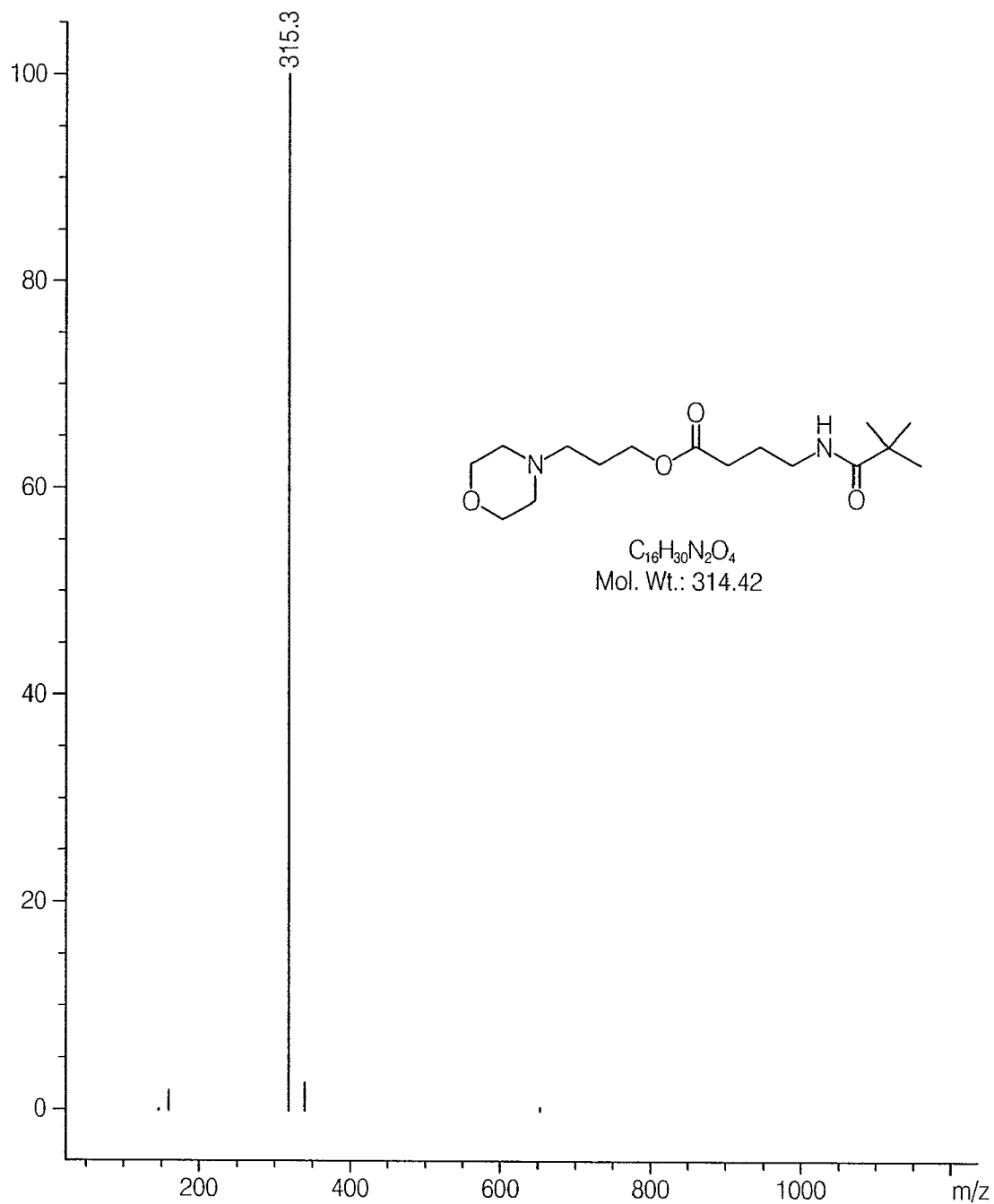
FIG. 8 is a mass spectrum of a compound according to an embodiment shown in EXAMPLE 2 below.
Figure 9:
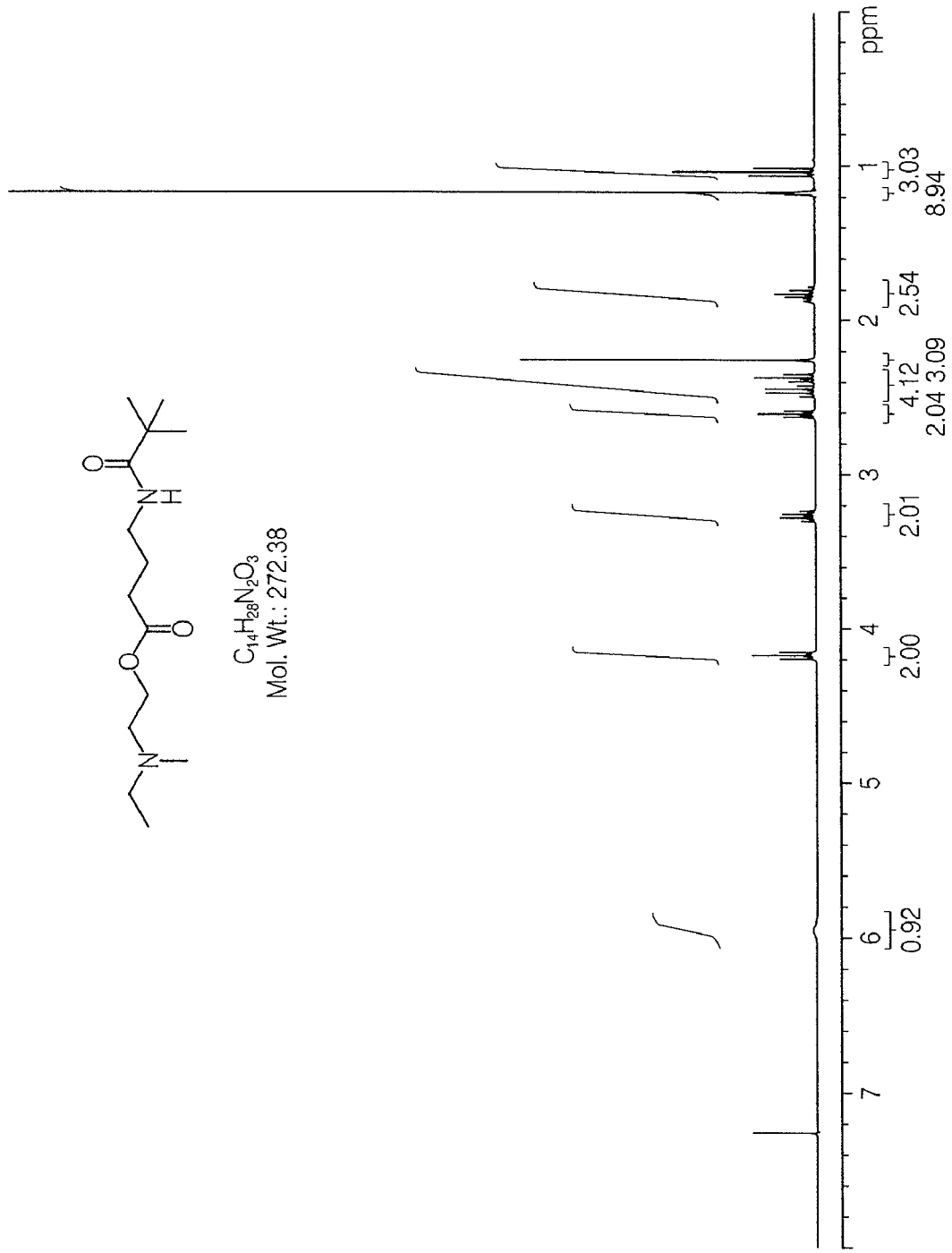
FIG. 9 is a proton NMR spectrum of a compound according to an embodiment shown in EXAMPLE 4 below.
Figure 10:
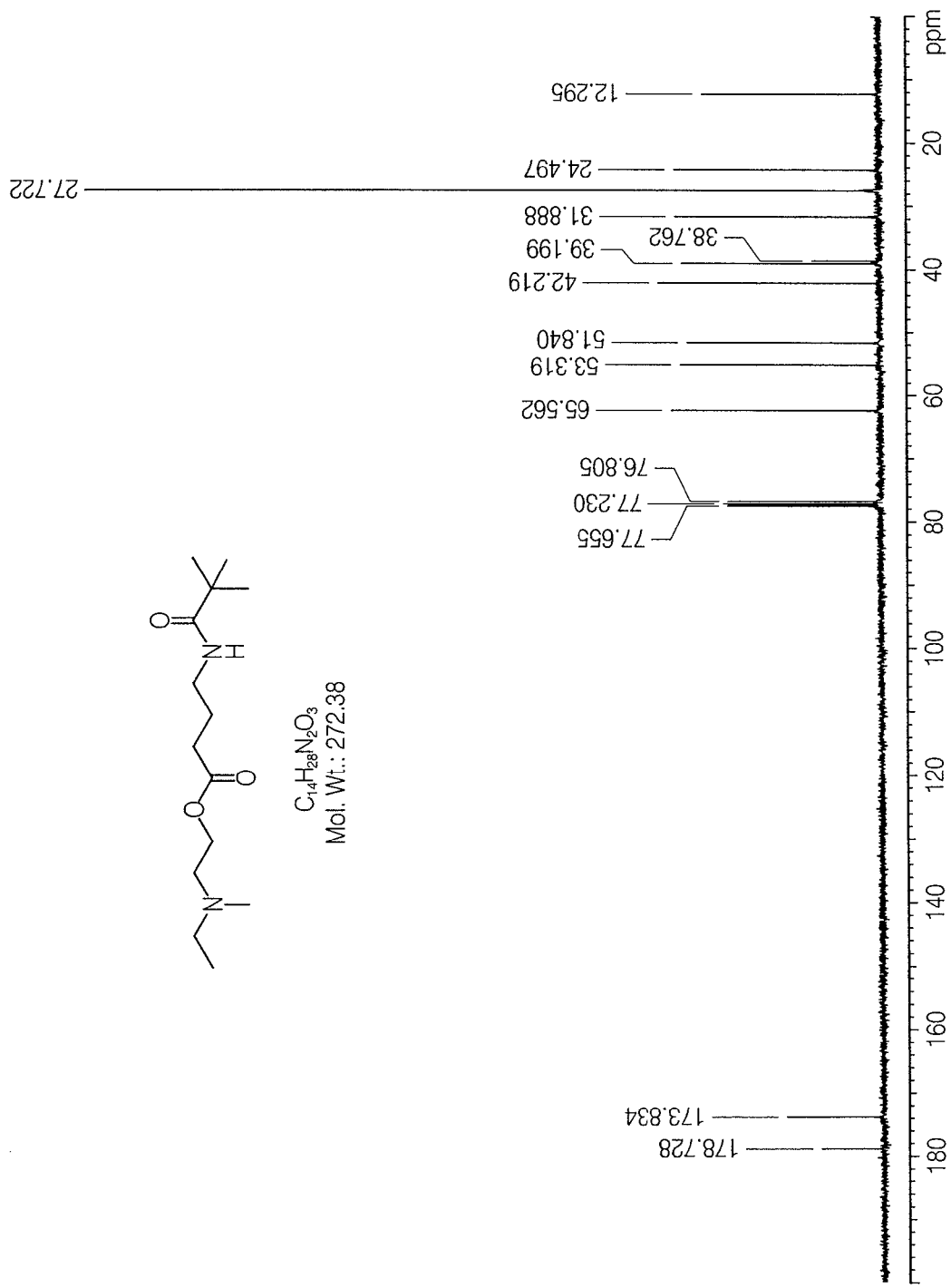
FIG. 10 is a $^{13}$C NMR spectrum of a compound according to an embodiment shown in EXAMPLE 4 below.
Figure 11:
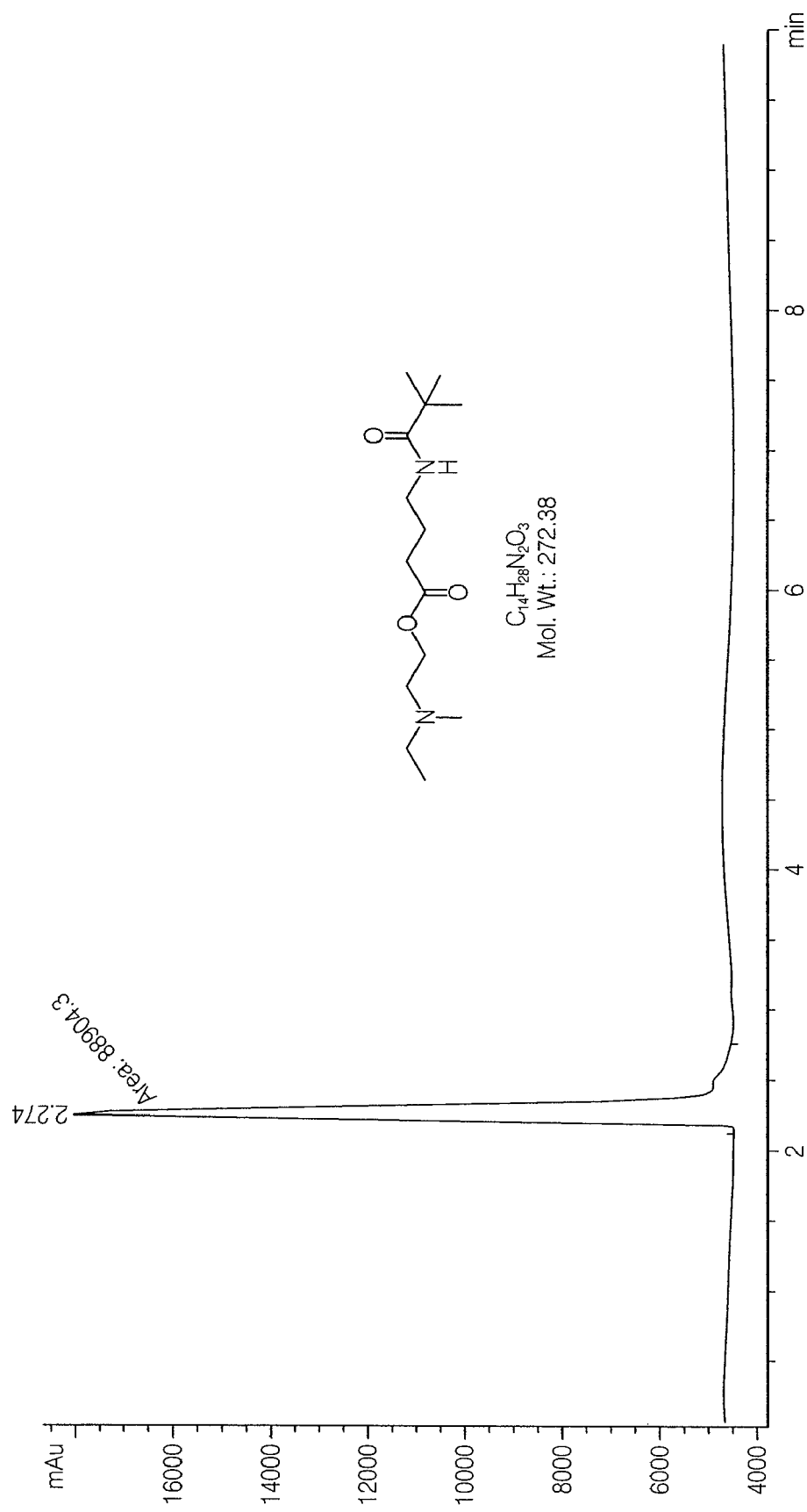
FIG. 11 is an HPLC chromatogram of a compound according to an embodiment shown in EXAMPLE 4 below.
Figure 12:
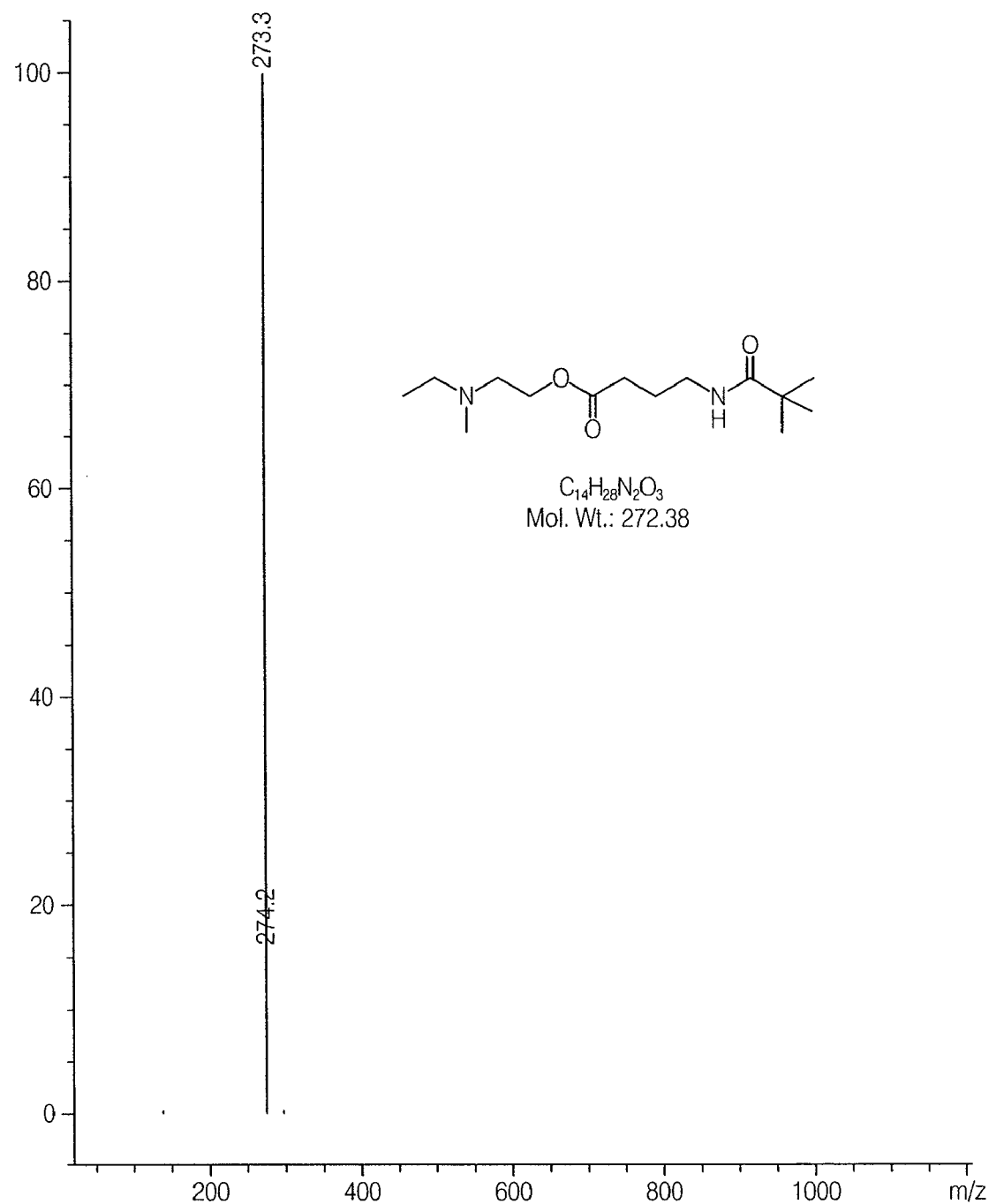
FIG. 12 is a mass spectrum of a compound according to an embodiment shown in EXAMPLE 4 below.
Figure 13:
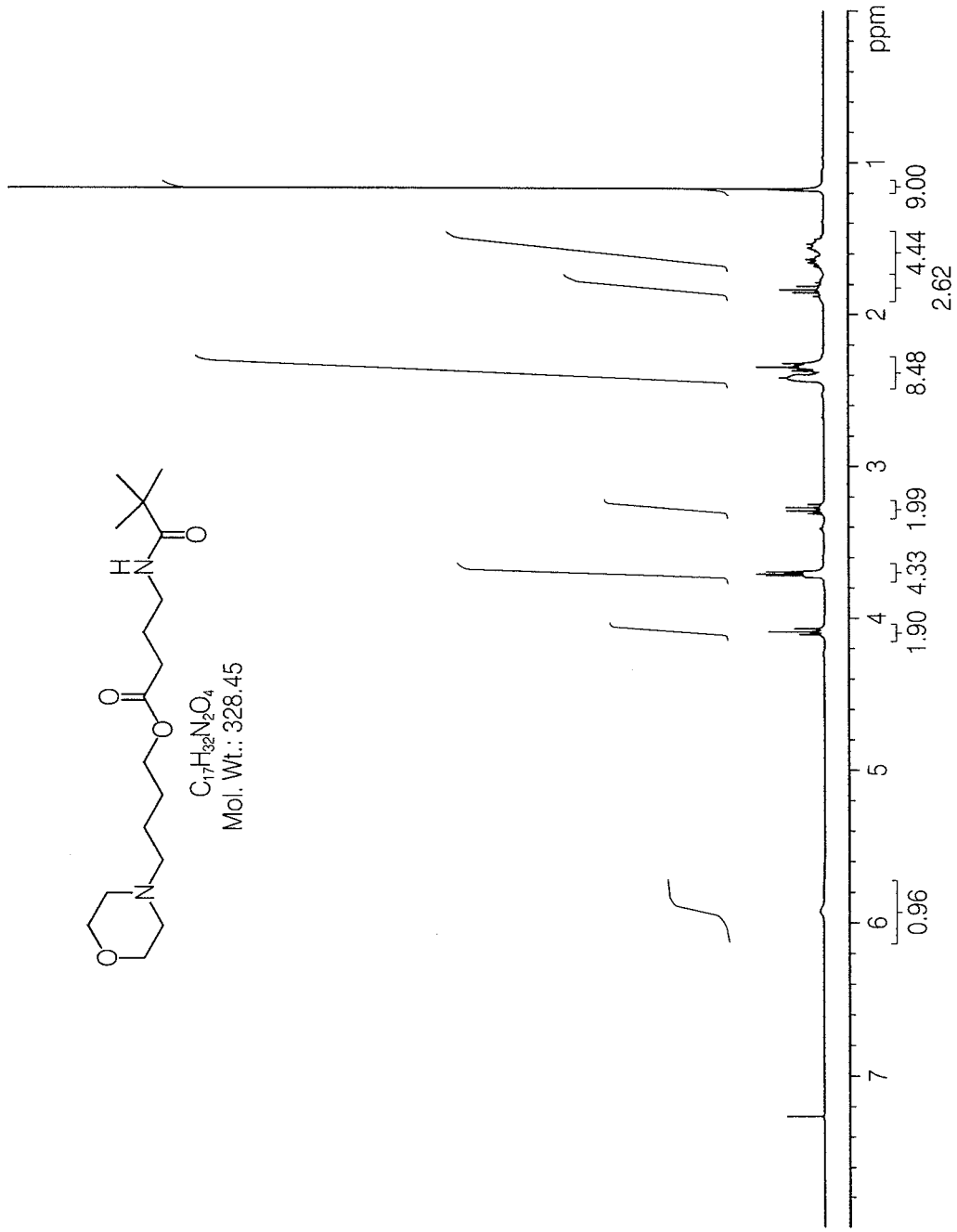
FIG. 13 is a proton NMR spectrum of a compound according to an embodiment shown in EXAMPLE 3 below.
Figure 14:
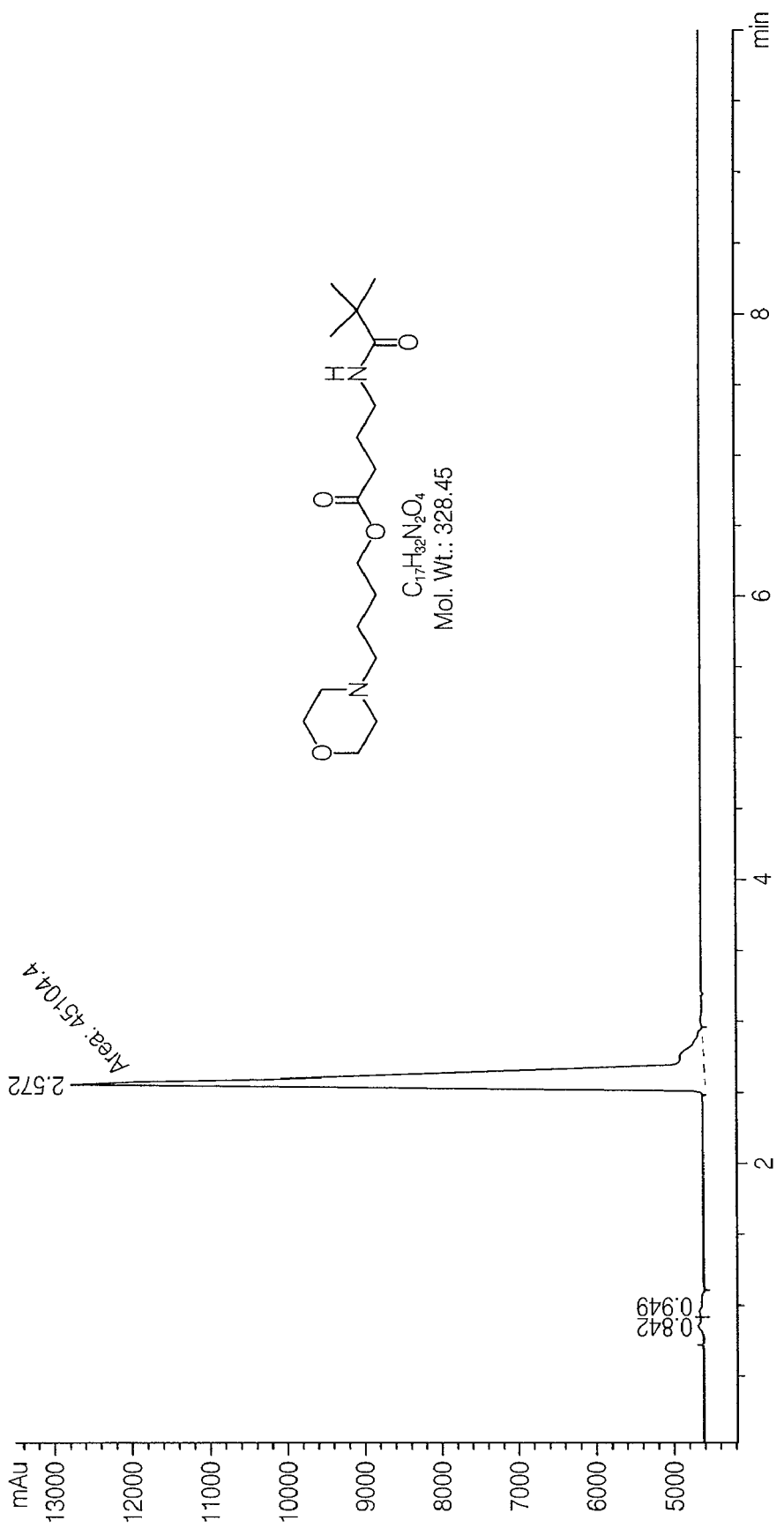
FIG. 14 is a $^{13}$C NMR spectrum of a compound according to an embodiment shown in EXAMPLE 3 below.
Figure 15:
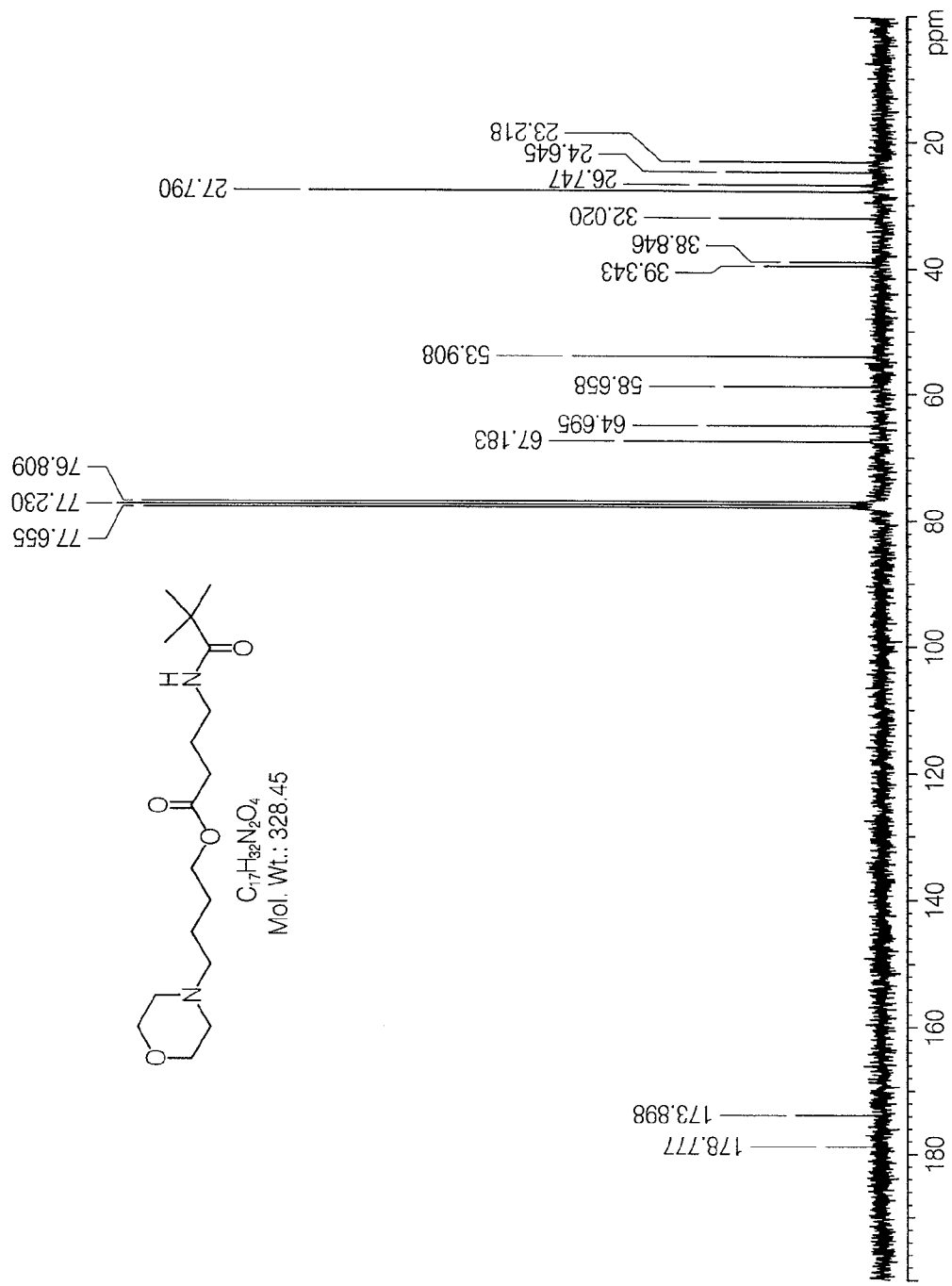
FIG. 15 is an HPLC chromatogram of a compound according to an embodiment shown in EXAMPLE 3 below.
Figure 16:
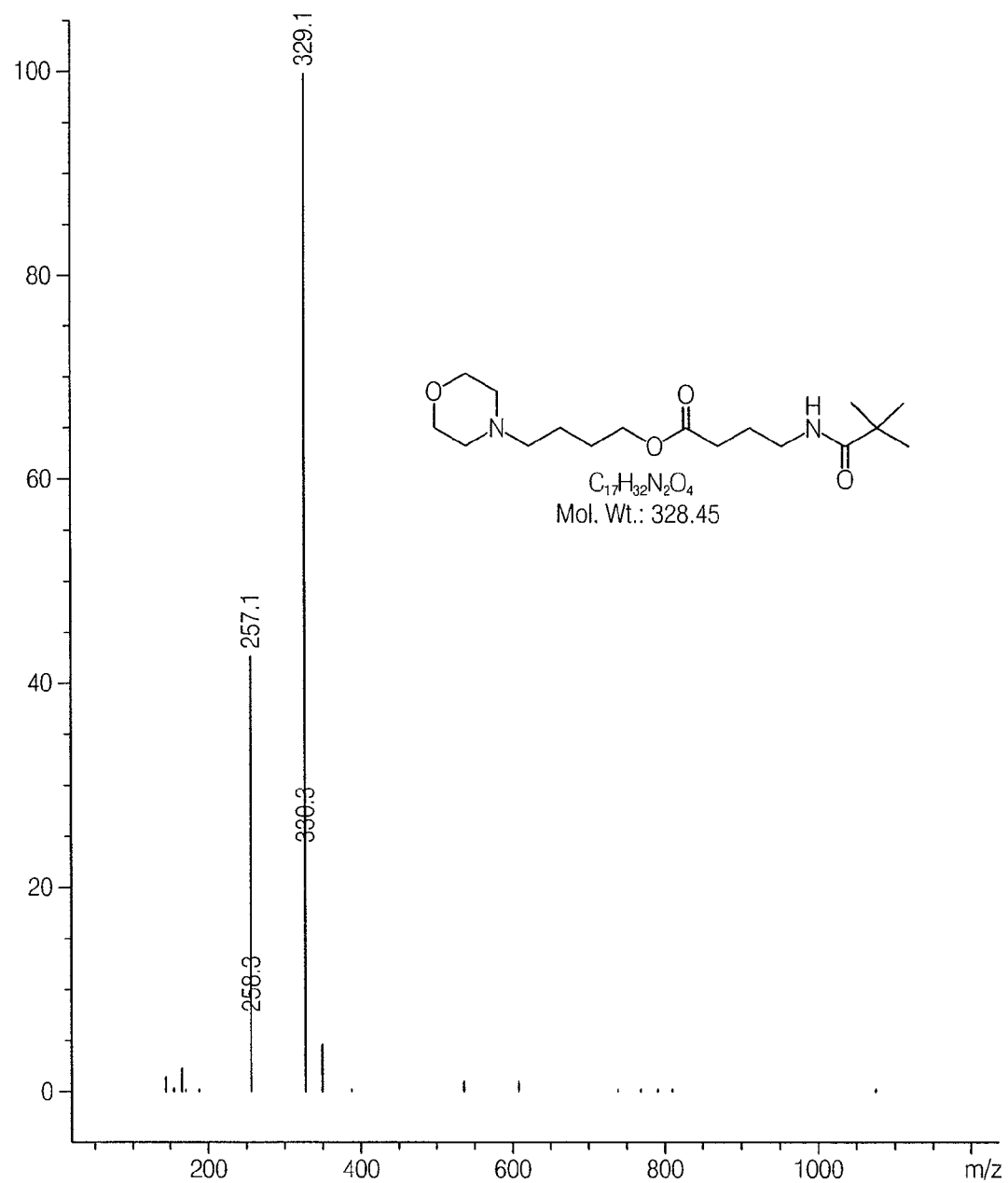
FIG. 16 is a mass spectrum of a compound according to an embodiment shown in EXAMPLE 3 below.
Figure 17:
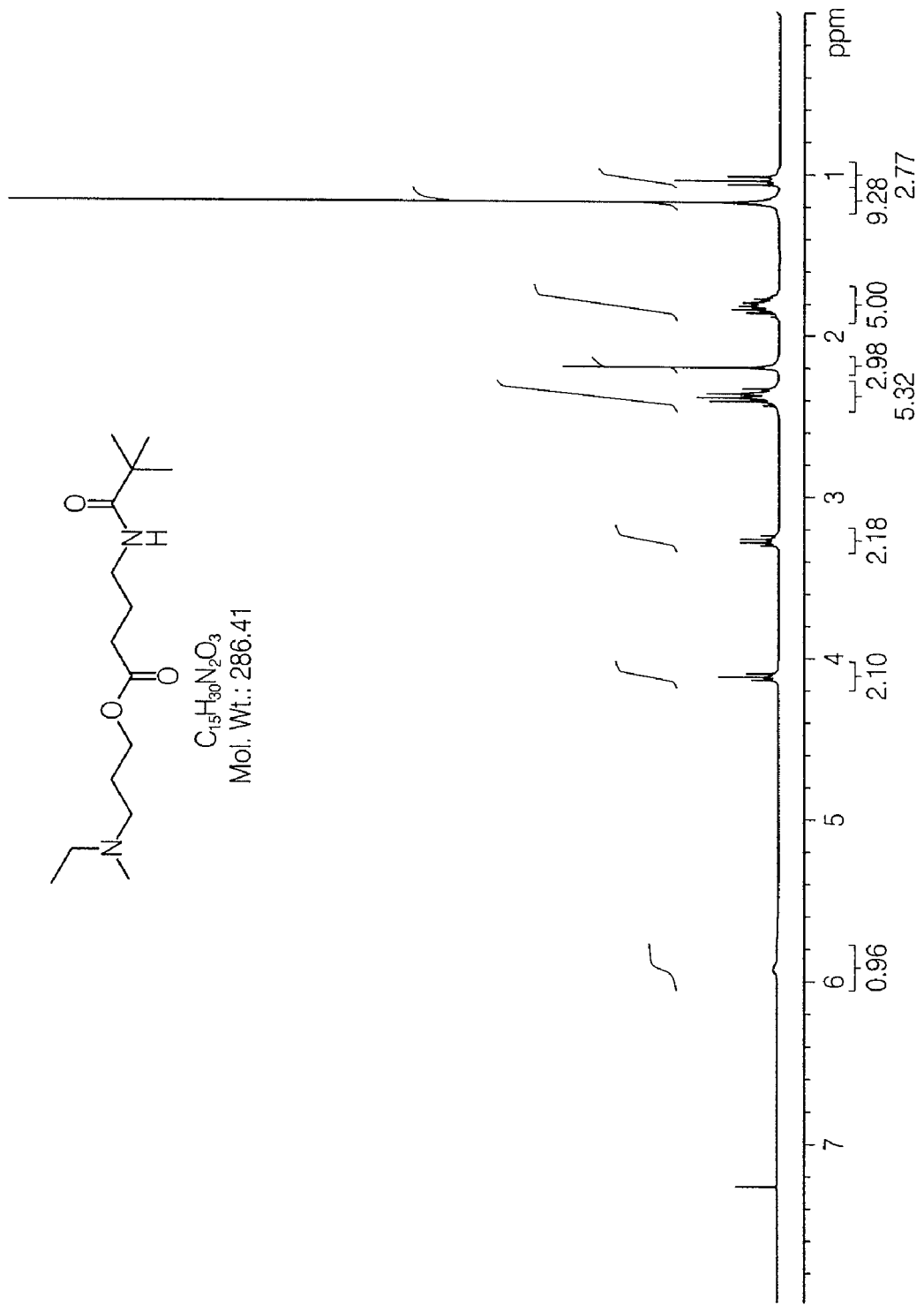
FIG. 17 is a proton NMR spectrum of a compound according to an embodiment shown in EXAMPLE 5 below.
Figure 18:
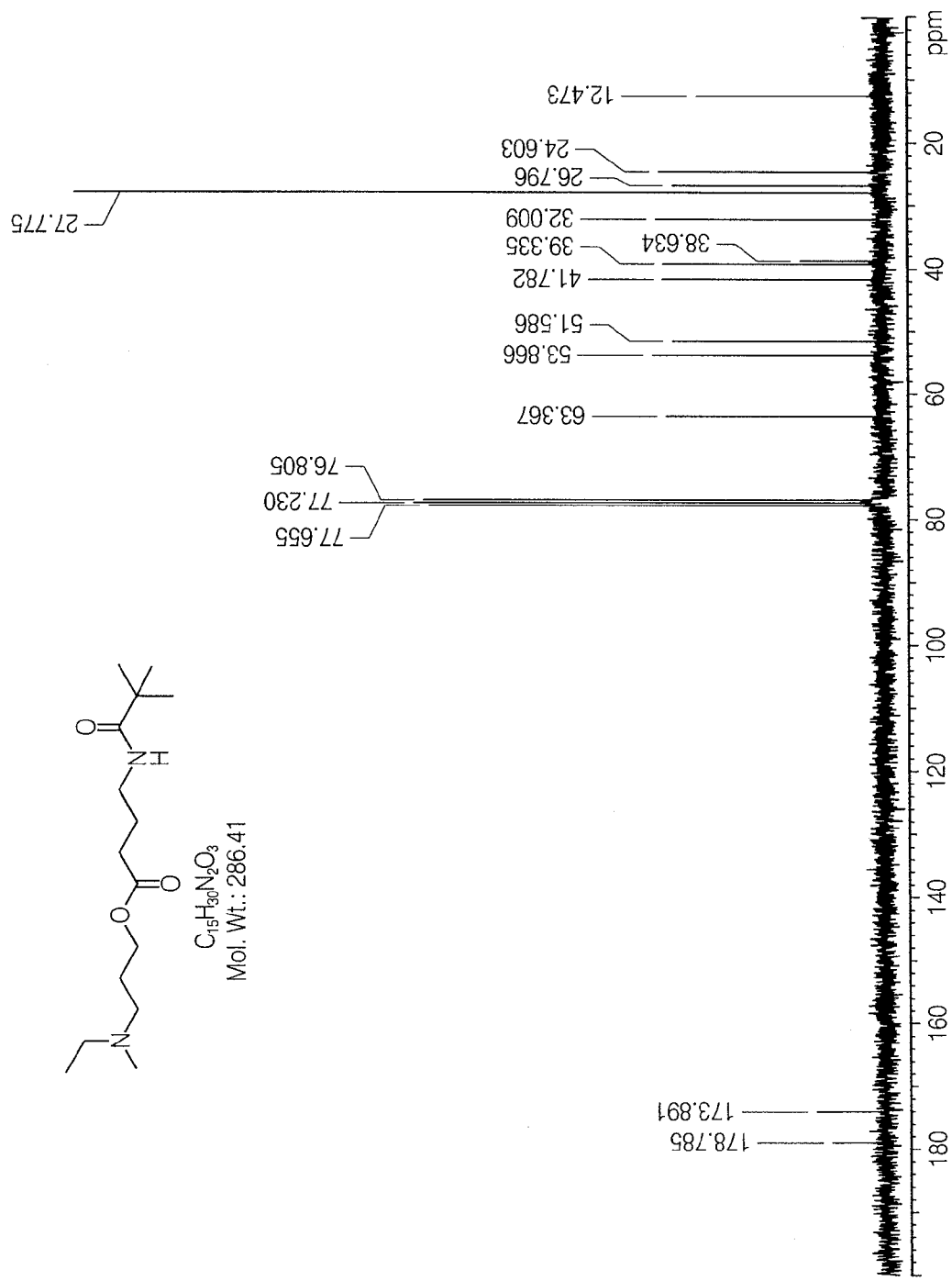
FIG. 18 is a $^{13}$C NMR spectrum of a compound according to an embodiment shown in EXAMPLE 5 below.
Figure 19:
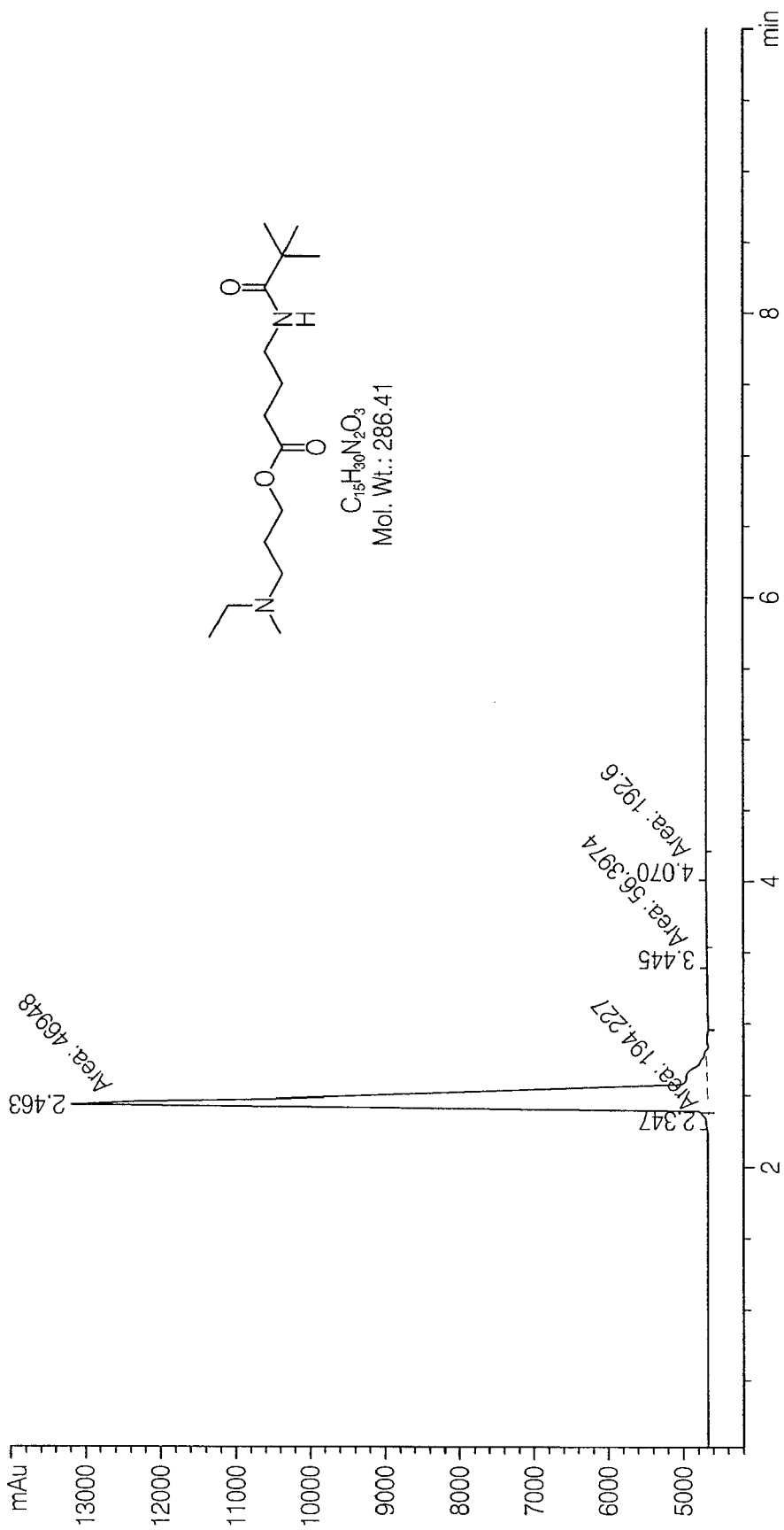
FIG. 19 is an HPLC chromatogram of a compound according to an embodiment shown in EXAMPLE 5 below.
Figure 20:
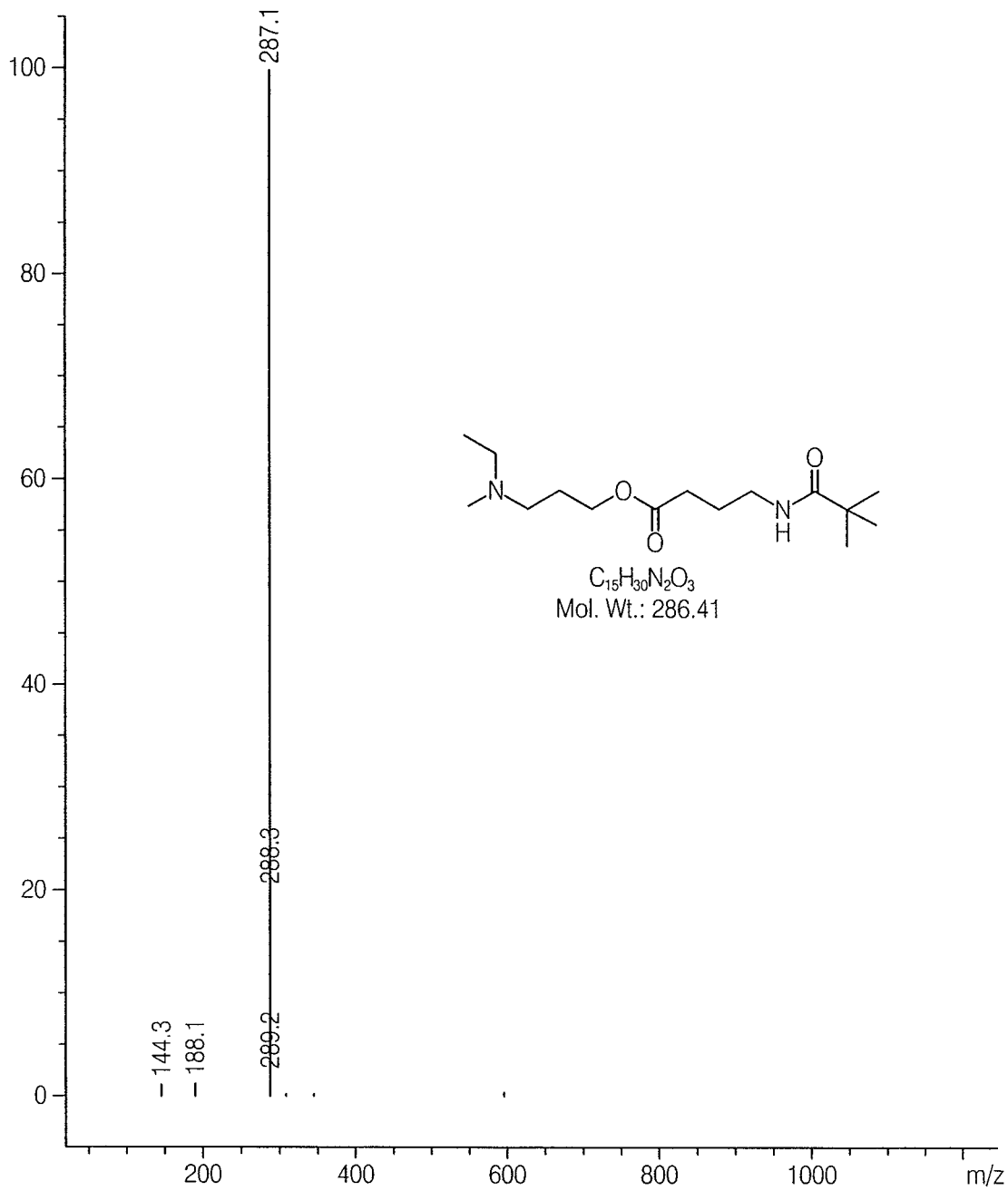
FIG. 20 is a mass spectrum of a compound according to an embodiment shown in EXAMPLE 5 below.

The present embodiments are related to the compounds of Formula 1 or Formula 2 below and pharmaceutical formulations thereof as well as treatments for a wide variety of Central Nervous System disorders with the pharmaceutical formulations. While the present embodiments are not limited by the nature of the compounds, some embodiments include the use of a variety the instant compounds which surprisingly and advantageously exhibit improved pharmacokinetic and therapeutic profiles in comparison to pivagabine. Some embodiments relate to compounds derived from the following generic structure:

Formula 1

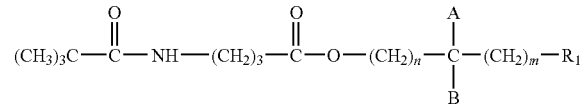

wherein, m is 0, 1, 2, 3 or 4;

wherein, n is 1, 2, 3, or 4;

wherein A and B are independently selected from H, $C_1$-$C_4$ alkyl;

wherein A and B may together represent a cyclic hydrocarbon moiety consisting of 2, 3, 4 or 5 methylene units;

and wherein $R_1$ is selected from a) the group consisting of,

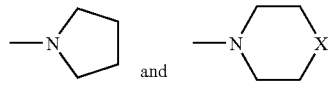

wherein X is selected from the group consisting of methylene ($CH_2$), unsubstituted or substituted nitrogen, oxygen, or sulfur; or b) the group consisting of an unsymmetrical amine group of the formula

wherein $R_3$ and $R_4$ are independently selected from H, a $C_1$-$C_8$ branched alkyl, a $C_1$-$C_8$ linear alkyl, or a $C_1$-$C_8$ branched or linear alkyl substituted with at least one group selected from —$OR_5$,

and —$SR_8$, wherein $R_5$, $R_6$, $R_7$ and $R_8$ are independently selected from H, a $C_1$-$C_8$ branched alkyl and a $C_1$-$C_8$ linear alkyl; and wherein $R_3$ and $R_4$ are not identical; and solvates, hydrates, salts, isomers, including pure enantiomers and diastereomers thereof and mixtures in any proportion thereof. It will be understood that any of the forgoing compounds can be in a crystalline or amorphous state or a mixture thereof.

Formula 2

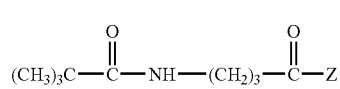

wherein Z is selected from (I)

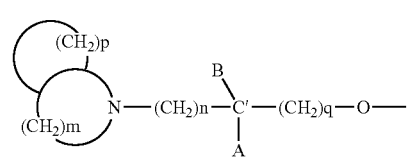

(II)

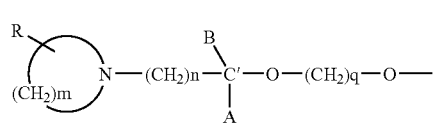

(III)

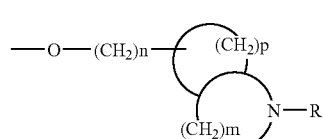

(IV)

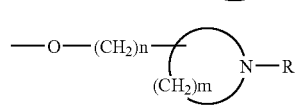

(V)

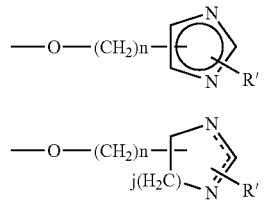

(VI)

wherein n, m, p and q are each independently selected from 0, 1, 2, 3 and wherein j is selected from 1, 2 and 3, wherein A, B and R are each independently selected from H and a $C_1$-$C_4$ alkyl, wherein A and B may together represent a cyclic hydrocarbon moiety consisting of 2, 3, 4 or 5 methylene units, wherein R' is selected from H, $C_1$-$C_4$ alkyl, OH, COOH, $CONR_2$, alkoky, hydroxyalkyl, aryl, heteroaryl, arylalkyl and heteroarylalkyl groups and solvates, hydrates, salts, isomers, including pure enantiomers and diastereomers thereof and mixtures in any proportion thereof. It will be understood that any of the forgoing compounds can be in a crystalline or amorphous state or a mixture thereof.

In some embodiments, Z can be selected from the following:

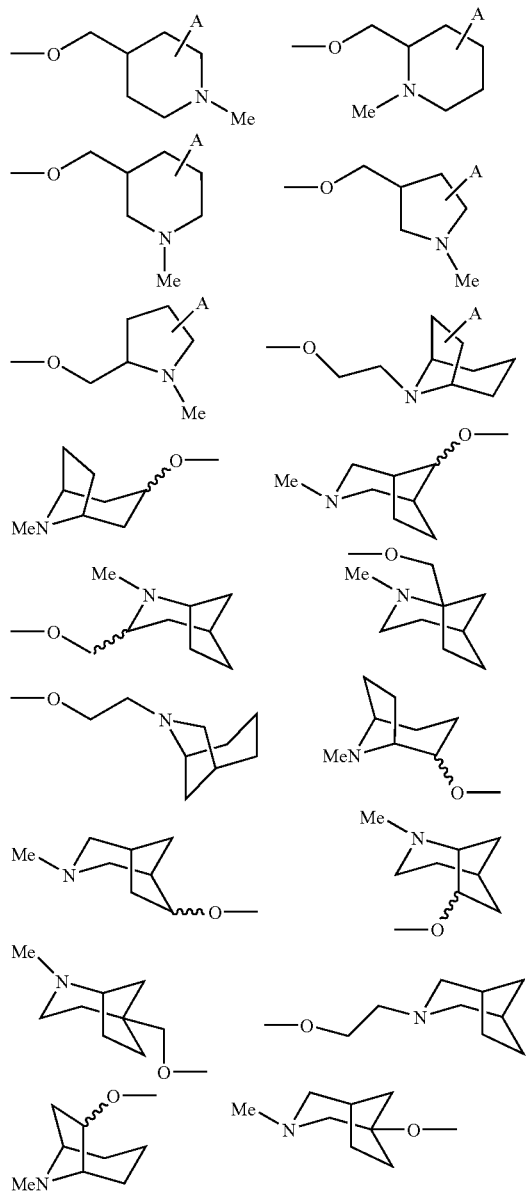

-continued

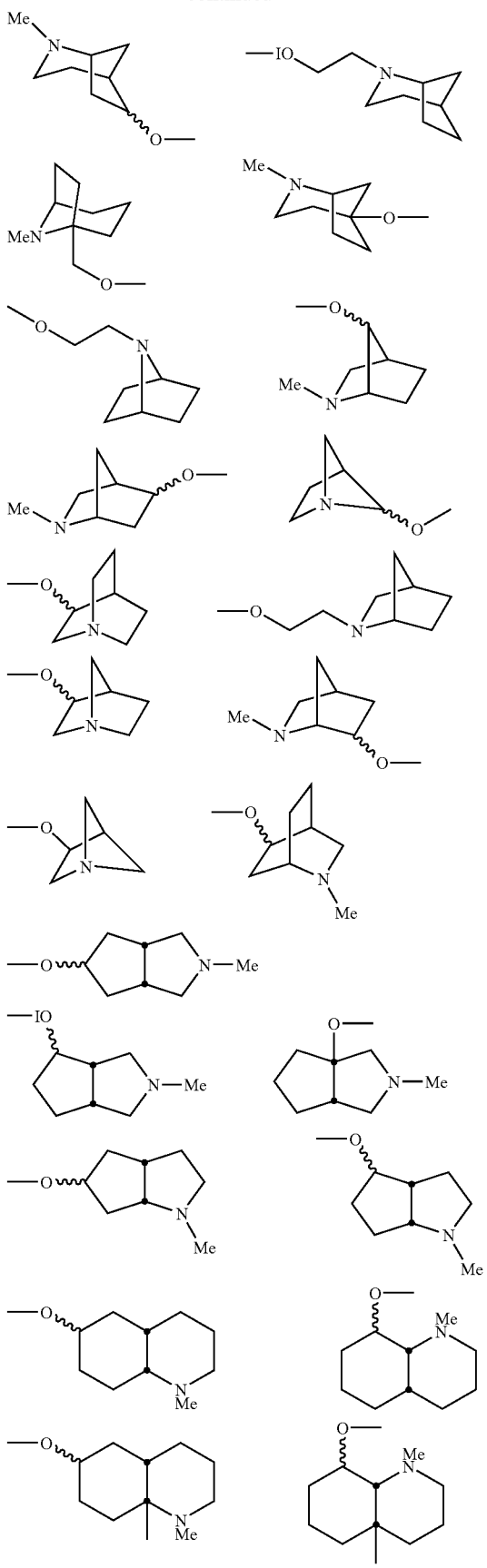

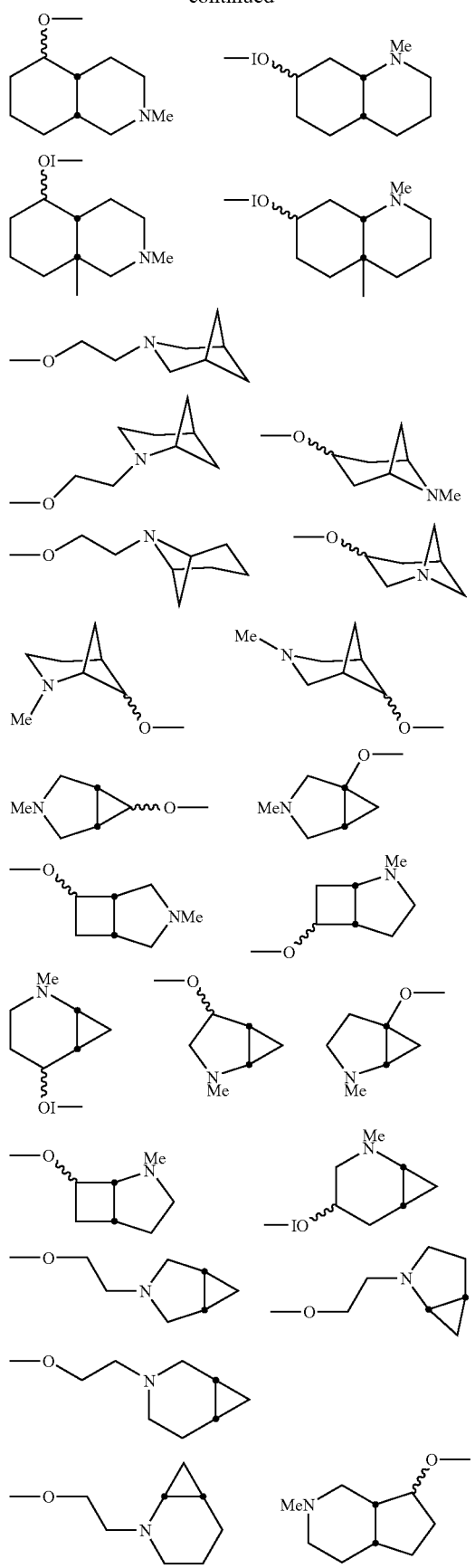
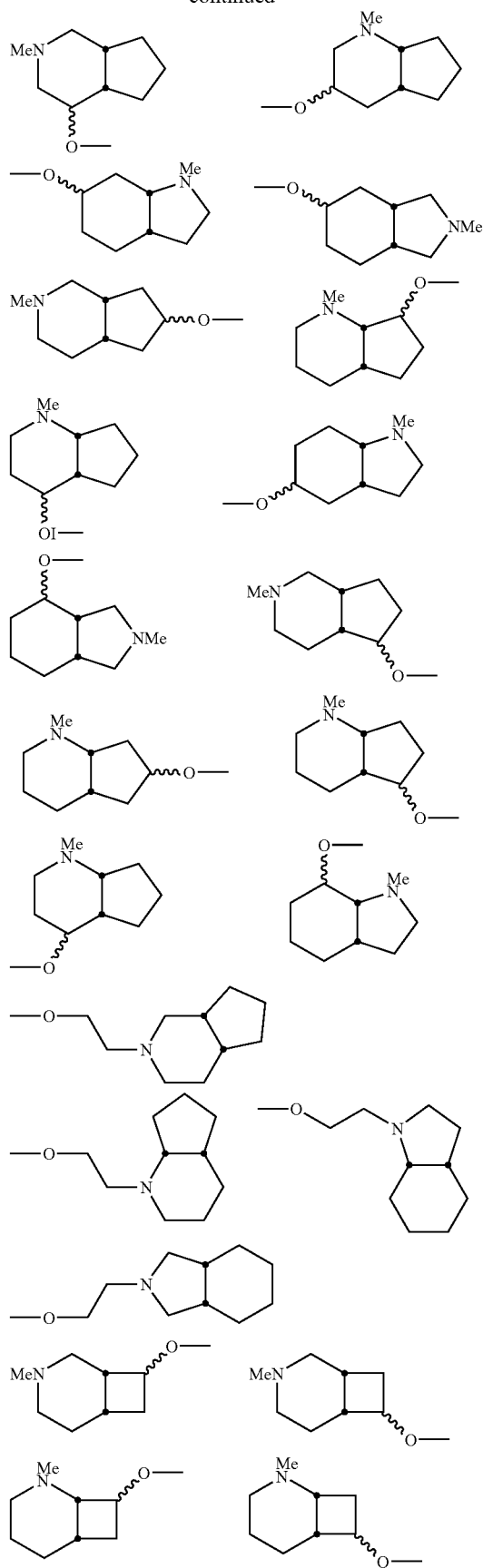

-continued

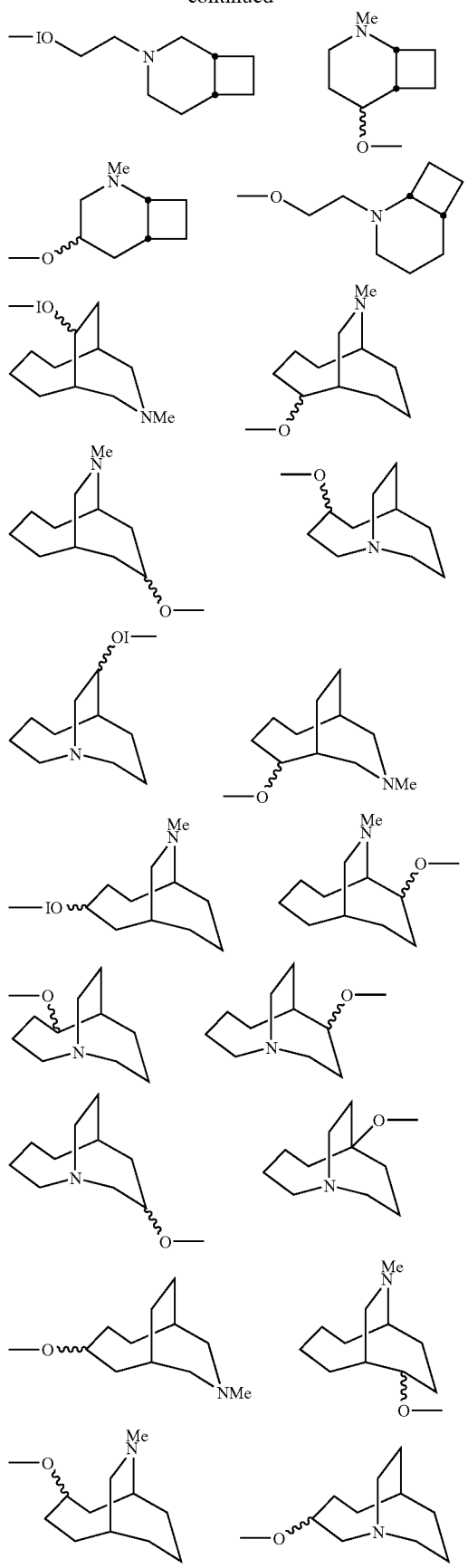

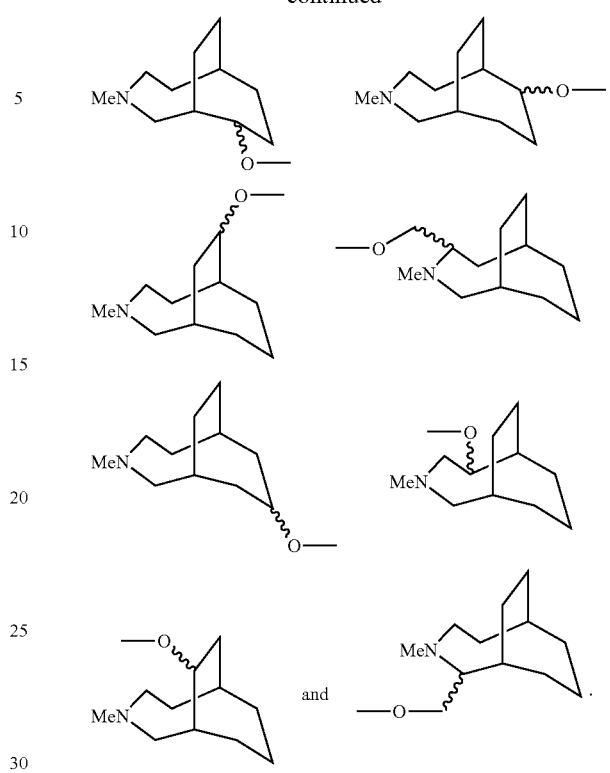

The compounds described above can be prepared by any standard method of ester formation, including, for example, the following scheme.

In one embodiment, an example of the instant compounds can be synthesized by the following steps:

performing an acylation reaction reacting a compound with the following structure:

Compound A:

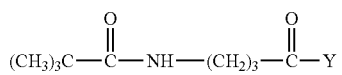

wherein Y is a leaving group (examples of suitable leaving groups are discussed below), with a compound having the following structure:

Compound B:

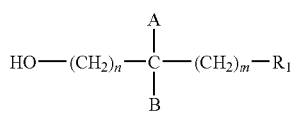

wherein, m is 0, 1, 2, 3 or 4;

wherein, n is 1, 2, 3, or 4;

wherein A and B are independently selected from H, $C_1$-$C_4$ alkyl; wherein A and B may together represent a cyclic hydrocarbon moiety consisting of 2, 3, 4 or 5 methylene units;

and wherein
R$_1$ is selected from
a) the group consisting of,

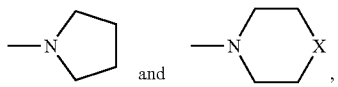

wherein X is selected from the group consisting of methylene (CH$_2$), unsubstituted or substituted nitrogen, oxygen, or sulfur or
b) the group consisting of an unsymmetrical amine group of the formula

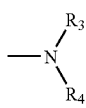

wherein R$_3$ and R$_4$ are independently selected from H, a C$_1$-C$_8$ branched alkyl, a C$_1$-C$_8$ linear alkyl, or a C$_1$-C$_8$ branched or linear alkyl substituted with at least one group selected from —OR$_5$,

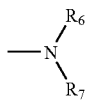

and —SR$_8$,
wherein R$_5$, R$_6$, R$_7$ and R$_8$ are independently selected from H, a C$_1$-C$_8$ branched alkyl and a C$_1$-C$_8$ linear alkyl; and
wherein R$_3$ and R$_4$ are not identical; and
solvates, salts, hydrates, isomers, including pure enantiomers and diastereomers thereof and mixtures in any proportion thereof;
and yielding the following structure:

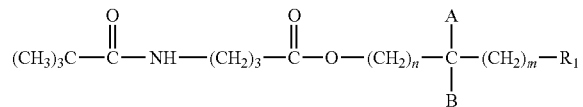

wherein, m is 0, 1, 2, 3 or 4;
wherein, n is 1, 2, 3, or 4;
wherein A and B are independently selected from H, C$_1$-C$_4$ alkyl;
wherein A and B may together represent a cyclic hydrocarbon moiety consisting of 2, 3, 4 or 5 methylene units;
and wherein
R$_1$ is selected from
a) the group consisting of,

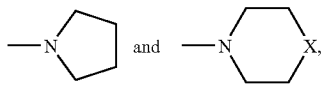

wherein X is selected from the group consisting of methylene (CH$_2$), unsubstituted or substituted nitrogen, oxygen, or sulfur or
b) the group consisting of an unsymmetrical amine group of the formula

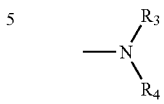

wherein R$_3$ and R$_4$ are independently selected from H, a C$_1$-C$_8$ branched alkyl, a C$_1$-C$_8$ linear alkyl, or a C$_1$-C$_8$ branched or linear alkyl substituted with at least one group selected from —OR$_5$,

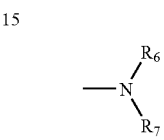

and —SR$_8$,
wherein R$_5$, R$_6$, R$_7$ and R$_8$ are independently selected from H, a C$_1$-C$_8$ branched alkyl and a C$_1$-C$_8$ linear alkyl; and
wherein R$_3$ and R$_4$ are not identical; and
solvates, hydrates, salts, isomers, including pure enantiomers and diastereomers thereof and mixtures in any proportion thereof. It will be understood that any of the forgoing compounds can be in a crystalline or amorphous state or a mixture thereof.

Examples of suitable leaving groups include, but are not limited to, halogen atoms such as fluorine, chlorine, bromine and iodine, pyridine-2-thiol, trihalogenomethyloxy groups such as trichloromethoxy, lower alkanesulfonyloxy groups such as methanesulfonyloxy and ethanesulfonyloxy groups, lower halogeno alkane sulfonyloxy groups such as trifluoromethanesulfonyloxy and pentafluoroethanesulfonyloxy groups, arylsulfonyloxy groups such as benzenesulfonyloxy, p-toluenesulfonyloxy, p-nitrobenzenesulfonyloxy groups, O-tosyl groups, O-triflyl groups, O-mesyl groups, N-imidazolyl groups, N-triazolyl groups, N-benzotriazolyl groups, benzotriazolyloxy groups, imidazolyloxy groups, N-imidazolinone groups, N-imidazolone groups, N-imidazolinethione groups, N-succinimidyl groups, N-phthalimidyl groups, N-succinimidyloxy groups, N-phthalimidyloxy groups, 2-pyridyloxy groups, pentafluorophenyl groups, p-nitrophenol, 2,4-dinitrophenol, trichlorophenol, pentachlorophenol, 2-chloro-4,6-dimethoxytriazene, N-chlorosuccinimide, N-chloromaleic imide, N-chlorophthalimide, 1-hydroxy-1H-benzotriazole, 1-hydroxy-6-chloro-1H-benzotriazole, methoxycarbonyl groups, ethoxycarbonyl groups, isobutoxycarbonyl groups, acid anhydride and mixed anhydride forms such as trichloromethylcarbonyl groups, iso-but-2-ylcarbonyl groups and the like.

One method of the acylation step is to simply combine the compound A with compound B in the presence of an acid scavenger. Another method is to combine compound B with the free carboxylic acid form of Compound A and a condensing agent. Suitable condensing agents include N,N'-disubstituted carbodiimides such as N,N'-dicyclohexylcarbodiimide, N,N-diethylcarbodiimide, N,N'-di-(n-propyl)carbodiimide, N,N'-di-(iso-propyl)carbodiimide, N,N'-bis(p-dimethylaminophenyl)carbodiimide, N-ethyl-N'-(4'''-ethylmorpholinyl) carbodiimide and the like. Other suitable carbodiimides are disclosed by Sheehan in U.S. Pat. No. 2,938,892 and by Hofmann et al. in U.S. Pat. No. 3,065,224. Azolides, such as N,N'-carbonyldiimidazole and N,N'-thionyldiimidazol, may also be used as condensing agents. Dehydrating agents such as phosphorus oxychloride, the alkoxyacetylenes and 2-halogenopyridinium salts (such as 2-chloropyridinium methyl iodide, 2-fluoropyridinium methyl iodide, and the like) may be used to couple the free acid or its acid salt with Compound B.

Another acylation method entails first converting the free carboxylic acid form (or the corresponding salt) of compound A to the active ester derivative which is in turn used to acylate the Compound B. The active ester derivative is formed by esterifying the free acid form with groups such as p-nitrophenol, 2,4-dinitrophenol, trichlorophenol, pentachlorophenol, 2-chloro-4,6-dimethoxytriazene, N-chlorosuccinimide, N-chloro maleic imide, N-chlorophthalimide, 1-hydroxy-1H-benzotriazole or 1-hydroxy-6-chloro-1H-benzotriazole. The active ester derivatives can also be mixed anhydrides, which are formed with groups such as methoxycarbonyl, ethoxycarbonyl, isobutoxycarbonyl, trichloromethylcarbonyl and iso-but-2-ylcarbonyl and the carboxylic acid of Compound A. The mixed anhydrides are synthesized by acylating the carboxylic acid of Compound A.

Alternatively, Compound B can be acylated with the N-ethoxycarbonyl-2-ethoxy-1,2-dihydroquinoline (EEDQ) derivative of Compound A. In some embodiments, the free acid form of Compound A and EEDQ are reacted in an inert, polar organic solvent (such as tetrahydrofuran, acetonitrile, and the like). The resultant EEDQ derivative is used in situ to acylate Compound B.

The structures of some of the compounds of the present embodiments include stereogenic carbon atoms. It is to be understood that isomers arising from such asymmetry (e.g., all tautomers, enantiomers, diastereomers and mixtures thereof) are included within the scope of the present embodiments unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present embodiments may exist in unsolvated as well as solvated forms with acceptable solvents such as water, THF, ethanol, and the like. In general, the solvated forms are considered equivalent to the unsolvated forms for the purposes of the present embodiments.

As used herein, the term $C_1$-$C_8$ linear alkyl refers to saturated and unsaturated hydrocarbons having one, two, three four, five, six, seven or eight carbon atoms, including, for example, methyl, ethyl, vinyl, allyl, propyl, butyl, pentyl, hexyl, heptyl, octyl, vinyl, allyl, 1-butenyl, 2-butenyl, ethynyl, 1-propynyl, and 2-propynyl.

As used herein, the term $C_1$-$C_8$ branched alkyl groups refers to saturated and unsaturated branched hydrocarbon chains such as isopropyl, 2-methylprop-1-enyl and tert-butyl, homologs and isomers of, for example, n-pentyl, n-hexyl, n-heptyl, n-octyl, 2-propenyl, crotyl, 2-isopentenyl, 2-(butadienyl), 2,4-pentadienyl, 3-(1,4-pentadienyl), ethynyl, 1- and 3-propynyl, 3-butynyl and the like.

Unless otherwise specified, the chemical moieties of the compounds, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_8$ alkyl" or similar designations. By way of example only, "$C_1$-$C_8$ alkyl" indicates that there are one to eight carbon atoms in the alkyl chain, i.e., the alkyl chain is selected from the group consisting of methyl, ethyl, propyl, iso-propyl, n-butyl, iso-butyl, sec-butyl, t-butyl, cyclohexyl, (cyclohexyl)ethyl, cyclopropylmethyl, homologs and isomers of, for example, n-pentyl, n-hexyl, n-heptyl, n-octyl, 2-propenyl, crotyl, 2-isopentenyl, 2-(butadienyl), 2,4-pentadienyl, 3-(1,4-pentadienyl), ethynyl, 1- and 3-propynyl, 3-butynyl and the like.

The alkyl group of the present embodiments may be substituted or unsubstituted. When substituted, the substituent group(s) is (are) one or more group(s) individually and independently selected from substituted or unsubstituted alkyl, substituted or unsubstituted alkenyl, substituted or unsubstituted alkynyl, substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxyl, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo; O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and $SO_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl"

rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzothiazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

As used herein, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

As used herein, the term "cycloheteroalkyl" alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker (CH$_2$)$_r$ (where r is 1, 2 or 3).

"Hydroxyalkyl" refers to an alkyl as defined above that is substituted by a hydroxy radical, e.g., hydroxymethyl, 2-hydroxyethyl, 2-hydroxypropyl, 3-hydroxypropyl, 4-hydroxybutyl, 3-hydroxybutyl, and the like.

The term "alkoxyalkyl" refers to an alkyl group substituted with an alkoxy group, for example isopropoxymethyl.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

The present embodiments also include pharmaceutical formulations comprising a therapeutically effective amount of any of the compounds described above and a pharmaceutically acceptable carrier. In one embodiment a pharmaceutical formulation is made by combining any of the compounds described above and a pharmaceutically acceptable carrier. The present embodiments further include a process for making a pharmaceutical formulation comprising combining any of the compounds described above and a pharmaceutically acceptable carrier.

As used herein, the term "pharmaceutically acceptable carrier" includes any and all solvents, dispersion media, coatings, permeation enhancers, antibacterial and antifungal agents, isotonic and absorption delaying agents and the like compatible with pharmaceutical administration.

As used herein, the term "formulation" encompasses a product comprising the specified ingredients in the specified amounts, as well as any product which results, directly or indirectly, from combination of the specified ingredients in the specified amounts.

The present embodiments include pharmaceutical formulations comprising one or more compounds described throughout in association with a pharmaceutically acceptable carrier. Preferably these formulations are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual, buccal, topical or rectal administration, or for administration by inhalation or insufflation. Also, the instant compounds can be administered to the body through Xenoport technology. XenoPort identifies and characterizes transporters throughout the body that are useful to drug delivery, then uses selected transporter proteins as "targets" and employs medicinal chemistry techniques to modify drugs into substrates for these transporters.

Alternatively, the formulations may be presented in a form suitable for once-daily, once-weekly or once-monthly administration; for example, an insoluble salt of the active compound may be adapted to provide a preparation for intramuscular injection. The pharmaceutical formulations described herein can be administered to a patient per se, or in pharmaceutical formulations where they are mixed with other active ingredients, as in combination therapy, or suitable pharmaceutically acceptable carriers or excipient(s). Techniques for formulation and administration of the compounds of the instant application may be found in "Remington's Pharmaceutical Sciences," Mack Publishing Co., Easton, Pa., 18th edition, 1990.

For preparing solid pharmaceutical formulations such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation formulation containing a homogeneous mixture of a compound of the present embodiments, or a pharmaceutically acceptable salt thereof. When referring to these preformulation formulations as homogeneous, it is meant that the active ingredient is dispersed evenly throughout the formulation so that the formulation may be readily subdivided into equally effective unit dosage forms such as tablets, pills and capsules. This solid preformulation formulation is then subdivided into unit dosage forms of the type described above containing from about 10 to about 10,000 mg of the compounds of Formula 1 of the present embodiments. Preferably the dosage is from about 50 to about 5000 mg; more preferably, the dosage is from about 450 to about 1800 mg; even more preferably, the dosage is from about 600 to about 1000 mg. The tablets or pills of the novel formulation can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Furthermore, compounds for the present embodiments can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The formulations may take such forms as suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile pyrogen-free water, before use.

For oral administration, the instant compounds can be formulated readily by combining the active compounds with pharmaceutically acceptable carriers well known in the art. Such pharmaceutically acceptable carriers enable the compounds of the present embodiments to be formulated as tablets, pills, dragees, capsules, liquids, gels, syrups, slurries, suspensions and the like, for oral ingestion by a patient to be treated. Pharmaceutical formulations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal administration, the pharmaceutical formulations may take the form of tablets, lozenges, wafers and rapid-dissolve preparations formulated in conventional manner.

The compounds of the present embodiments can also be administered in the form of liposome pharmaceutical formulations, such as small unilamellar vesicles, large unilamellar vesicles and multilamellar vesicles. Liposomes can be formed from a variety of phospholipids, such as cholesterol, stearylamine or phosphatidylcholines.

Further disclosed herein are various pharmaceutical formulations well known in the pharmaceutical art for uses that include intraocular, intranasal, and intraauricular delivery. Suitable penetrants for these uses are generally known in the art. Pharmaceutical formulations for intraocular delivery include aqueous ophthalmic solutions of the active compounds in water-soluble form, such as eyedrops, or in gellan gum (Shedden et al., *Clin. Ther.,* 23(3):440-50 (2001)) or hydrogels (Mayer et al., *Opthalmologica,* 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1): 101-6 (1999)); and ocular inserts.

Alternatively, other delivery systems for hydrophobic pharmaceutical compounds may be employed. Liposomes and emulsions are well known examples of delivery vehicles or pharmaceutical acceptable carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The dosage regimen utilizing the compounds of the present embodiments is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the pharmaceutical formulation's availability to target sites. This involves a consideration of the distribution, equilibrium, and elimination of the compounds. Advantageously, compounds of the present embodiments may be administered, for example, in a single daily dose, or the total daily dosage may be administered in divided doses of two, three or four times daily.

In the methods of the present embodiments, the pharmaceutical formulations herein described in detail are typically administered in accordance with conventional pharmaceutical practices.

For instance, for oral administration in the form of a tablet or capsule, the compounds of the present embodiments can be combined with an oral, non-toxic pharmaceutically acceptable inert carrier such as ethanol, glycerol, water and the like. Moreover, when desired or necessary, suitable pharmaceutically acceptable carriers, such as, binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Some examples of pharmaceutically acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety.

The oral liquid formulations in which the present embodiments may be incorporated for administration orally include using pharmaceutically acceptable carriers, aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous oral suspensions include synthetic and natural gums such as tragacanth, acacia, alginate, dextran, sodium carboxymethylcellulose, methylcellulose, polyvinyl-pyrrolidone or gelatin. Other dispersing agents which may be employed include glycerin and the like.

The daily dosage of the products may be varied over a wide range; e.g., from about 10 to about 10,000 mg per adult human per day. For oral administration, the formulations are preferably provided in the form of tablets containing about 10.0, 15.0, 25.0, 50.0, 100, 200, 300, 400, 500, 600, 700, 800, 900 1000, 2000, 3000, 4000, 5000, 6000, 7000, 8000, 9000 or 10,000 milligrams of the active ingredient for the symptomatic adjustment of the dosage to the patient to be treated. The instant pharmaceutical formulations typically contain from 10 mg to about 2000 mg of the instant compounds, preferably, from about 50 mg to about 1000 mg of active ingredient. An effective amount of the instant compounds is ordinarily supplied at a dosage level of from about 0.002 mg/kg to about 150 mg/kg of body weight per day. Preferably, the range is from about 0.02 to about 80 mg/kg of body weight per day, and especially from about 0.2 mg/kg to about 40 mg/kg of body weight per day. The compounds may be administered on a regimen of about 1 to about 10 times per day.

As used herein, "Central Nervous System disorder" refers to any neurological disorder that affects the brain or spinal column, including, but not limited to, acute stress disorder; affective disorders, including depressive disorders (major depressive disorder, dysthymia, childhood depression, atypical depression, bipolar disorder, mania and hypomania) and anxiety disorders (generalized anxiety disorder, social anxiety disorder, phobias, obsessive compulsive disorder, panic disorder, post-traumatic stress disorder); premenstrual dysphoric disorder (also known as pre-menstrual syndrome); psychotic disorders, such as brief psychotic disorder, schizophrenia, psychotic mood disorder (depression and/or mania); attention deficit disorder (with and without hyperactivity); obesity, eating disorders such as anorexia nervosa and bulimia nervosa; vasomotor flushing; cocaine and alcohol addiction; sexual dysfunction and related illnesses; acute and chronic pain syndromes, as exemplified by fibromyalgia, arthritis, chronic low back pain, trigeminal neuralgia; visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome; neurologic disorders including seizure disorder, Tourette Syndrome, Parkinson's Disease, Huntington's Chorea, Alzheimer's Disease, subcortical and other dementias, Tardive Dyskinesia, Multiple Sclerosis, Rett Syndrome or amyotrophic lateral sclerosis.

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer and primates. The most preferred animal is human.

As used herein, the terms "treat" "treating" and "treatment" include "prevent" "preventing" and "prevention" respectively.

The instant compounds may be synthesized by methods described above, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known in the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

As used herein, "condensation conditions" refers to, for example, temperatures from about −10° C. to about 150° C., and the presence of catalysts such as, for example, calcium octoate, metal hydroxides like potassium hydroxide, Group I or Group II metals such as sodium or lithium, metal carbonates such as potassium carbonate or magnesium carbonate (which may be enhanced by use in combination with crown ethers), organometallic oxides and esters such as dibutyl tin oxide, stannous octoate, and calcium octoate, metal alkoxides such as sodium methoxide and aluminum tripropoxide and protic acids, such as, for example sulfuric acid, oleum, perchloric acid, $Ph_4SbI$, N,N'-disubstituted carbodiimides such as N,N'-dicyclohexylcarbodiimide, N,N'-diethylcarbodiimide, N,N'-di-(n-propyl)carbodiimide, N,N'-di-(iso-propyl)carbodiimide, N,N'-diallylcarbodiimide, N,N'-bis(p-dimethylaminophenyl)carbodiimide, N-ethyl-N'-(4"-ethylmorpholinyl)carbodiimide, and the like. Azolides, such as N,N'-carbonyldiimidazole and N,N-thionyldiimidazol, may also be used as condensing catalysts.

As used herein, "treat, treating and treatment" of a subject includes the application or administration of a formulation of the present embodiments to a subject, or application or administration of a formulation of the present embodiments to a cell or tissue from a subject, who has a central nervous system disease, disorder or condition, has a symptom of such a disease, disorder or condition, or is at risk of (or susceptible to) such a disease, disorder or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of disease. The treatment or amelioration of symptoms can be based on objective or subjective parameters; including the results of a physical examination, a psychiatric evaluation, including, for example, symptom ratings, such as the Clinical Dementia Rating (CDR), Mini-Mental State Examination (MMSE), Alzheimer Disease Assessment Scale-Cognitive (ADAS-Cog); a laboratory test indicating perturbations of the stress axis, such as dexamethasone suppression test (DST), the CRF challenge test; or another test known in the art. For example, the instant compounds, methods and formulations provide the treatment and prevention of diseases or disorders involving perturbation of the biological stress mechanisms including, but not limited to, acute stress disorder; affective disorders, including depressive disorders (major depressive disorder, dysthymia, childhood depression, atypical depression, bipolar disorder, mania and hypomania) and anxiety disorders (generalized anxiety disorder, social anxiety disorder, phobias, obsessive compulsive disorder, panic disorder, post-traumatic stress disorder); premenstrual dysphoric disorder (also known as pre-menstrual syndrome); psychotic disorders, such as brief psychotic disorder, schizophrenia, psychotic mood disorder (depression and/or mania); attention deficit disorder (with and without hyperactivity); obesity, eating disorders such as anorexia nervosa and bulimia nervosa; vasomotor flushing; cocaine and alcohol addiction; sexual dysfunction and related illnesses; acute and chronic pain syndromes, as exemplified by fibromyalgia, arthritis, chronic low back pain, trigeminal neuralgia; visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome; neurologic disorders including seizure disorder, Tourette Syndrome, Parkinson's Disease, Huntington's Chorea, Alzheimer's Disease, subcortical and other dementias, Tardive Dyskinesia, Multiple Sclerosis, Rett Syndrome or amyotrophic lateral sclerosis.

The instant compounds can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. For example, efficacy for depressive and anxiety or stress disorders can be predicted from animal models that include, but are not limited to, the Vogel Conflict Test, the Forced Swim Test, the Tail Suspension Test; efficacy for acute and chronic pain conditions can be predicted from animal models exemplified by the Tail Flick Test, the Hot Plate Test, Active and Passive Mechanical or Thermal Allodynia Tests, nerve compression or section test. When selecting a model to determine efficacy, the skilled artisan can be guided by the state of the art to choose an appropriate model, dose, and route of administration, and regime. Of course, human clinical trials can also be used to determine the efficacy of a compound in humans. The instant compounds and formulations can be screened using a combination of in vitro and in vivo techniques. The in vitro testing can involve measuring properties such as solubility, logP, permeability across membranes, and susceptibility to hydrolysis by esterases in the blood. In vivo testing can assess plasma-to-brain ratios of the concentration of pivagabine.

The following examples are provided for illustrative purposes only, and are in no way intended to limit the scope of the present embodiments.

The spectra shown in FIGS. 1-20 for the compounds below were collected using the following instruments: the proton NMR and the $^{13}$C NRM spectra were obtained with a Varian Mercury 300 MHz NMR spectrometer; the HPLC chromatograms were obtained using a normal phase column on an instrument equipped with an evaporative light scattering detector (ELSD).

Example 1

Into a 100 mL flask fitted with a Dean-Stark trap were added 1-(2-hydroxyethyl)-morpholine (4.2 g, 32 mmol), 4-(pivalamido)butanoic acid (3.0 g, 16 mmol), p-toluenesulfonic acid (100 mg, 0.5 mmol) and 50 mL of toluene. The reaction was heated to reflux. Conversion was periodically checked by HPLC (ELSD) and after 3 days complete conversion was observed. The reaction was allowed to cool to ambient temperature, was poured into saturated NaHCO$_3$, extracted with EtOAc and dried over Na$_2$SO$_4$. After filtration of the drying agent, solvent was removed in vacuo leaving a brown oil. The volatile impurities were removed by Kugelrohr distillation (100° C., 1 mm Hg, 1 h) leaving 4.0 g of the product (see reaction below) (13 mmol, 83% yield; >99% pure by HPLC) as a brown oil. The spectra for the product of this reaction are shown in FIGS. 1-4.

Example 2

The compound shown below was prepared under the following conditions. Into a 100 mL flask fitted with a Dean-Stark trap were added 1-(3-hydroxypropyl)morpholine (5.0 g, 34.4 mmol), 4-(pivalamido)butanoic acid (5.0 g, 27 mmol), p-toluenesulfonic acid (100 mg, 0.5 mmol) and 50 mL of toluene. The reaction was heated to reflux. Conversion was periodically checked by HPLC (ELSD) and after 4 days complete conversion was observed. The reaction was allowed to cool to ambient temperature, was poured into saturated NaHCO$_3$, extracted with EtOAc (2×250 mL) and dried over Na$_2$SO$_4$. After filtration of the drying agent, solvent was removed in vacuo leaving a brown oil. The volatile impurities were removed by Kugelrohr distillation (110° C., 1 mm Hg, 1 h) leaving 6.2 g of the product (see reaction below) (19.7 mmol, 74% yield; >99% pure by HPLC) as a brown oil. The spectra for the product of this reaction are shown in FIGS. 5-8.

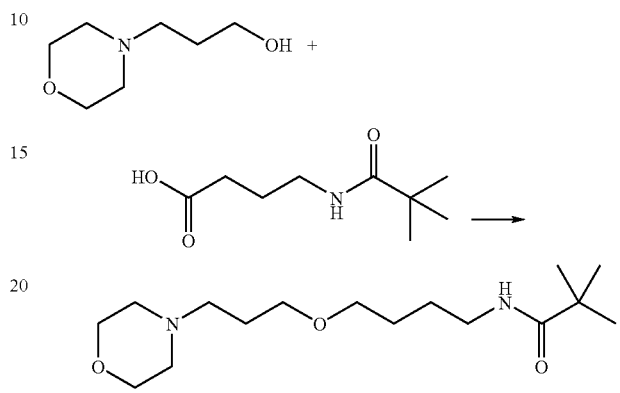

Example 3

1-(4-Hydroxybutyl)morpholine was prepared as follows. In a 250 mL flask was mixed morpholine (65.5 g, 750 mmol), 4-chlorobutanol (27.2 g, 250 mmol), sodium iodide (3.8 g, 25 mmol) and 75 mL of dioxane. The reaction was heated to reflux. After 2 days the reaction was allowed to cool to ambient temperature. Solvent was removed by rotary evaporation leaving a brown oil. The oil was dissolved in 100 mL of 2N NaOH, extracted with EtOAc and dried over Na$_2$SO$_4$. After filtration of the drying agent solvent was removed in vacuo leaving an orange oil. The oil was distilled (90° C., 1 mm Hg), leaving 1-(4-hydroxylbutyl)morpholine (13.9 g, 87 mmol, 35% yield) as a colorless oil.

Into a 100 mL flask fitted with a Dean-Stark trap were added 1-(4-hydroxybutyl)-morpholine (13.2 g, 83 mmol), 4-(pivalamido)butanoic acid (11.1 g, 59 mmol), p-toluenesulfonic acid (1.1 g, 5.9 mmol) and 55 mL of toluene. The reaction was heated to reflux. Conversion was periodically checked by HPLC (ELSD) and after 7 days ~80% conversion was observed. The reaction was allowed to cool to ambient temperature, was poured into saturated NaHCO$_3$, extracted with EtOAc (2×250 mL), washed with saturated NaHCO$_3$ and water and dried over Na$_2$SO$_4$. After filtration of the drying agent solvent was removed in vacuo at 90° C. leaving 7 g of the product (see reaction below) (21 mmol, 36% yield; >99% pure by HPLC) as a brown oil. The spectra for the product of this reaction are shown in FIGS. 13-16.

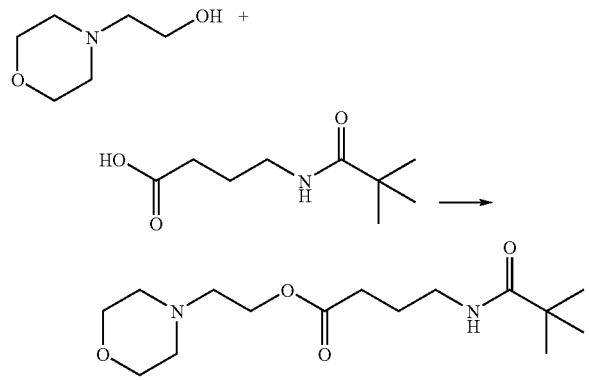

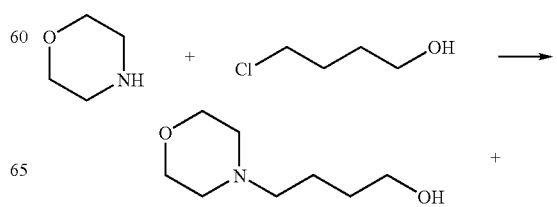

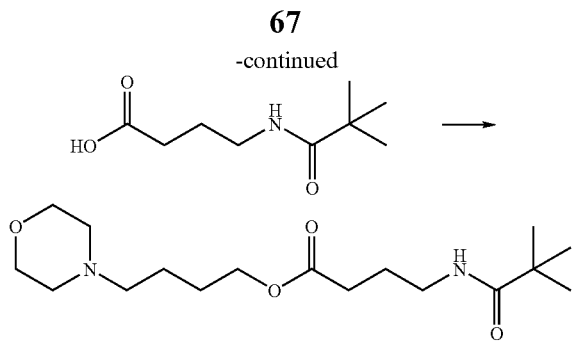

Example 4

2-(N-ethyl-N-methylamino)ethanol was prepared as follows:

In a pressure vessel were mixed N-ethyl-N-methylamine (25 g, 420 mmol), 4-chloroethanol (11.3 mL, 13.6 g, 170 mmol), sodium iodide (2.5 g, 17 mmol) and 75 mL of dioxane. The vessel was sealed and heated to 65° C. After 3 days the reaction was allowed to cool to ambient temperature. Solvent was removed by rotary evaporation leaving a brown oil. The oil was dissolved in 80 mL of 2N NaOH, extracted with EtOAc (3×200 mL) and dried over $Na_2SO_4$. After filtration of the drying agent solvent was removed in vacuo leaving a brown oil. The oil was distilled (45° C., 15 mm Hg) leaving 2-(N-ethyl-N-methylamino)ethanol (7.5 g, 73 mmol, 43% yield) as a colorless oil.

Into a 100 mL flask fitted with a Dean-Stark trap were added 2-(N-ethyl-N-methylamino)ethanol (7.5 g, 73 mmol), 4-(pivalamido)butanoic acid (10.5 g, 56 mmol), p-toluenesulfonic acid (1.07 g, 5.6 mmol) and 70 mL of toluene. The reaction was heated to reflux. Conversion was periodically checked by HPLC and after 2 days complete conversion was observed. The reaction was allowed to cool to ambient temperature, was poured into saturated. $NaHCO_3$, extracted with EtOAc (2×250 mL), washed with saturated $NaHCO_3$ and water and dried over $Na_2SO_4$. After filtration of the drying agent solvent was removed in vacuo at 70° C. leaving 10.3 g of the product (see reaction below) (38 mmol, 67% yield; >99% pure by HPLC) as a brown oil. The spectra for the product of this reaction are shown in FIGS. 9-12.

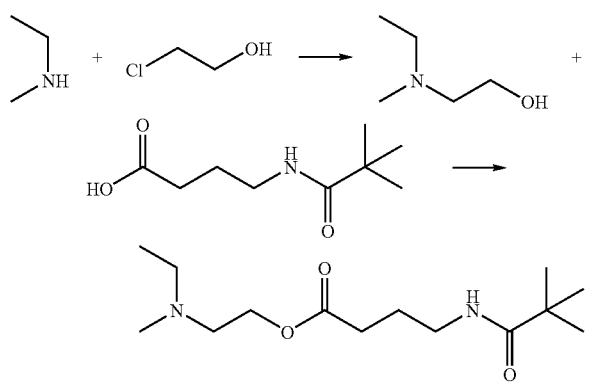

Example 5

3-(N-ethyl-N-methylamino)propanol was prepared as follows: In a pressure vessel was mixed N-ethyl-N-methylamine (25 g, 420 mmol), 3-chloropropanol (14.1 mL, 16 g, 170 mmol), sodium iodide (2.54 g, 17 mmol) and 60 mL dioxane. The vessel was sealed and heated to 65° C. After 3 days the reaction was allowed to cool to ambient temperature. Solvent was removed by rotary evaporation leaving a brown oil. The oil was dissolved in 80 mL of 2N NaOH, extracted with EtOAc (3×250 mL) and dried over $Na_2SO_4$. After filtration of the drying agent solvent was removed in vacuo leaving a brown oil. The oil was distilled (75° C., 15 mm Hg) leaving 2-(N-ethyl-N-methylamino)propanol (6.3 g, 54 mmol, 32% yield) as a colorless oil.

Into a 100 mL flask fitted with a Dean-Stark trap were added 3-(N-ethyl-N-methylamino) propanol (6.3 g, 54 mmol), 4-(pivalamido)butanoic acid (7.8 g, 41 mmol), p-toluenesulfonic acid (790 mg, 4.1 mmol) and 50 mL of toluene. The reaction was heated to reflux. Conversion was periodically checked by HPLC (ELSD) and after 3 days complete conversion was observed. The reaction was allowed to cool to ambient temperature, was poured into saturated $NaHCO_3$, extracted with EtOAc (2×250 mL), washed with saturated $NaHCO_3$ and water and dried over $Na_2SO_4$. After filtration of the drying agent solvent was removed in vacuo leaving 6.0 g of the product (see reaction below) (21 mmol, 51% yield; >99% pure by HPLC) as a brown oil. The spectra for the product of this reaction are shown in FIGS. 17-20.

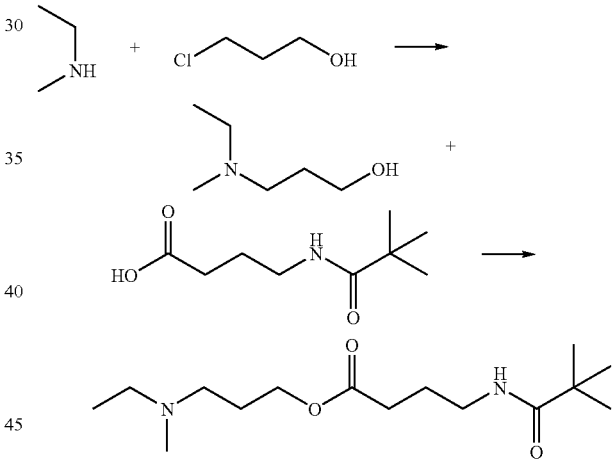

Example 6

CXB-722 (pivagabine) and five prodrugs (labeled CXB-723 (the product of the reaction shown in Example 1), CXB-724 (the product of the reaction shown in Example 2), CXB-725 (the product of the reaction shown in Example 3), CXB-726 (the product of the reaction shown in Example 4) and CXB-727 (the product of the reaction shown in Example 5)) were studied in three different protocols to assess:

- Membrane permeability (as a measure of absorption potential),
- Plasma stability (as a measure of the conversion of prodrugs to CXB-722), and
- In vivo pharmacokinetics following IV administration of all six compounds to evaluate plasma to CSF concentrations of CXB-722.

Membrane Permeability

The objective of the present study was to determine the permeability of six test compounds (drug candidate and five pro drugs) across CaCo-2 cell monolayers, in support of a preliminary evaluation of the potential for the oral absorption of these compounds. Permeability of each compound (50 μM) in the apical to basolateral and basolateral to apical direction was tested in duplicate. Samples were collected from the donor and acceptor chambers following 0 (donor only) and 60 min of incubation at 37° C. A generic LC-MS/MS (Liquid Chromatography/Mass Spectrometry/Mass Spectrometry) method was developed and qualified for the bioanalysis of the samples for all six test compounds. The permeability of [$^3$H] mannitol and [$^3$H]propranolol was determined in parallel as controls.

The results of this study are shown in the following table.

Preliminary CaCo-2 Permeability Assay Data

| Compound ID | Direction of Transport | Measured Concentration Tested (μM) | Replicate | TEER[a] (ohms*cm$^2$) | Recovery % | $P_{app}$[b] (nm/s) | Mean $P_{app}$ (nm/s) | B-A/A-B $P_{app}$ Ratio |
|---|---|---|---|---|---|---|---|---|
| CXB-722 | A-B | 46.4 | 1 | 362 | 110 | 13.0 | 10.7 | 0.533 |
|  |  | 49.9 | 2 | 405 | 99.3 | 8.29 |  |  |
|  | B-A | 55.7 | 1 | 425 | 81.6 | 5.64 | 5.68 |  |
|  |  | 49.0 | 2 | 431 | 95.6 | 5.73 |  |  |
| CXB-723 | A-B | 38.4 | 1 | 393 | 88.3 | 184 | 154 | 0.799 |
|  |  | 38.3 | 2 | 408 | 92.1 | 123 |  |  |
|  | B-A | 38.2 | 1 | 366 | 97.7 | 113 | 123 |  |
|  |  | 42.8 | 2 | 403 | 87.2 | 132 |  |  |
| CXB-724 | A-B | 47.3 | 1 | 378 | 80.3 | 110 | 114 | 1.05 |
|  |  | 44.7 | 2 | 464 | 82.3 | 117 |  |  |
|  | B-A | 53.2 | 1 | 424 | 70.5 | 120 | 119 |  |
|  |  | 44.2 | 2 | 366 | 94.0 | 118 |  |  |
| CXB-725 | A-B | 43.3 | 1 | 494 | 94.2 | 93.9 | 116 | 1.08 |
|  |  | 48.9 | 2 | 427 | 89.1 | 139 |  |  |
|  | B-A | 47.7 | 1 | 392 | 105 | 129 | 126 |  |
|  |  | 46.8 | 2 | 412 | 131 | 122 |  |  |
| CXB-726 | A-B | 42.0 | 1 | 424 | 84.2 | 63.3 | 81.4 | 1.27 |
|  |  | 41.8 | 2 | 487 | 91.5 | 99.5 |  |  |
|  | B-A | 38.9 | 1 | 371 | 95.5 | 114 | 104 |  |
|  |  | 41.2 | 2 | 462 | 92.6 | 93.0 |  |  |
| CXB-727 | A-B | 44.0 | 1 | 393 | 104 | 53.5 | 52.2 | 0.972 |
|  |  | 43.1 | 2 | 359 | 106 | 50.9 |  |  |
|  | B-A | 44.3 | 1 | 358 | 100 | 53.0 | 50.7 |  |
|  |  | 44.5 | 2 | 422 | 102 | 48.5 |  |  |

Note:
[a]TEER represents the trans-epithelial resistance.
[b]$P_{app}$ denotes the apparent permeability coefficient.

Plasma Stability

The objective of the present study was to determine the plasma stability of the six test compounds (CXB-722 and five pro-prodrugs) in rat plasma incubations. Each compound (20 μM) was incubated at 37° C. with male Sprague-Dawley rat plasma. Reaction mixtures were sampled at 0, 30, 60 and 120 minutes from duplicate incubations and reactions terminated by the addition of an equal volume of ice cold acetonitrile. Each compound (20 μM) was also incubated with Dulbecco's phosphate buffered saline, pH 7.4 (PBS) (0 and 120 minutes) to determine chemical stability. A tandem liquid chromatography mass spectrometry (LC-MS/MS) method was developed for each compound for measuring relative stability of test compound in the terminated reaction mixtures. The relative disappearance of the test compounds following 30, 60 and 120 min of incubation with rat plasma was determined in duplicate samples. Test compound stability following 0 and 120 min of incubation with PBS was also determined.

The results of this study are summarized in the following tables.

TABLE 1

Mean test compound concentrations, determined in duplicate, as a function of incubation time in pooled male Sprague-Dawley rat plasma and PBS.

| Compound ID | Matrix | Concentration (μM) | | | |
|---|---|---|---|---|---|
|  |  | 0 min | 30 min | 60 min | 120 min |
| CXB-722 | Plasma | 19.5 | 19.9 | 18.7 | 19.9 |
|  | Buffer | 21.9 |  |  | 22.6 |
| CXB-723 | Plasma | 23.3 | 0.0220 | BLQ | 0.00* |
|  | Buffer | 24.2 |  |  | 21.6 |
| CXB-724 | Plasma | 20.9 | BLQ | 0.00 | 0.00 |
|  | Buffer | 21.5 |  |  | 21.5 |
| CXB-725 | Plasma | 20.0 | BLQ | BLQ | 0.00 |
|  | Buffer | 21.2 |  |  | 21.9 |

TABLE 1-continued

Mean test compound concentrations, determined in duplicate, as a function of incubation time in pooled male Sprague-Dawley rat plasma and PBS.

| Compound ID | Matrix | Concentration (μM) | | | |
|---|---|---|---|---|---|
|  |  | 0 min | 30 min | 60 min | 120 min |
| CXB-726 | Plasma | 18.3 | 0.00 | 0.00 | 0.00 |
|  | Buffer | 33.7 |  |  | 30.3 |
| CXB-727 | Plasma | 21.3 | 0.0131 | BLQ | 0.00 |
|  | Buffer | 21.6 |  |  | 21.9 |

BLQ denotes below the limit of quantitation
*peak not detected

TABLE 2

Mean concentrations of CXB-722 formation in pro-drug incubations, determined in duplicate, as a function of incubation time in pooled male Sprague-Dawley rat plasma and PBS.

| Compound | | CXB-722 Concentration (μM) | | | |
|---|---|---|---|---|---|
| ID | Matrix | 0 min | 30 min | 60 min | 120 min |
| CXB-723 | Plasma | 9.67 | 17.1 | 18.0 | 18.4 |
| | Buffer | 0.924 | | | 5.90 |
| CXB-724 | Plasma | 2.54 | 19.0 | 19.1 | 20.2 |
| | Buffer | 0.354 | | | 1.60 |
| CXB-725 | Plasma | 1.31 | 23.9 | 23.9 | 21.7 |
| | Buffer | 0.566 | | | 0.727 |
| CXB-726 | Plasma | 15.2 | 17.8 | 16.2 | 16.9 |
| | Buffer | 2.35 | | | 5.54 |
| CXB-727 | Plasma | 3.50 | 20.3 | 21.2 | 22.0 |
| | Buffer | 0.00 | | | 0.546 |

In Vivo Pharmacokinetics

The objective of this study was to determine the concentration of the drug candidate, CXB-722, and five pro-drugs of CXB-722 (CXB-723, CXB-724, CXB-725, CXB-726 and CXB-727) in serial blood plasma and cerebrospinal fluid (CSF) samples from anesthetized male Sprague-Dawley rats following intravenous (i.v.) bolus administration of each compound. Groups of 3 rats were dosed with 0.160 mmoles/kg (equivalent to 30 mg/kg CXB-722) of each test compound administered through a femoral vein catheter. CSF will be continuously collected via a catheter implanted in the cisterna magna by means of a peristaltic pump. CSF was collected over the following collection intervals following dosing: 0-20, 20-40, 40-60, 60-90, 90-120, 120-180, 180-240 and 240-300 min. Blood will be sampled from a femoral artery catheter at the midpoint of each CSF collection interval: 10, 30, 50, 75, 105, 150, 210 and 270 min. Plasma was isolated by centrifugation. Following sampling, the blood sample volume was replaced with an equivalent aliquot of fresh blood collected from undosed animals. A tandem liquid chromatography mass spectrometry (LC-MS/MS) method was developed and qualified for the quantification of CXB-722 and each pro-drug in plasma and CSF. Pharmacokinetic parameters (AUC, CL, Vss, t1/2, Cmax and tmax, where appropriate) were determined from the plasma and CSF concentration versus time curves for each animal using non-compartmental analysis.

Figure 24:
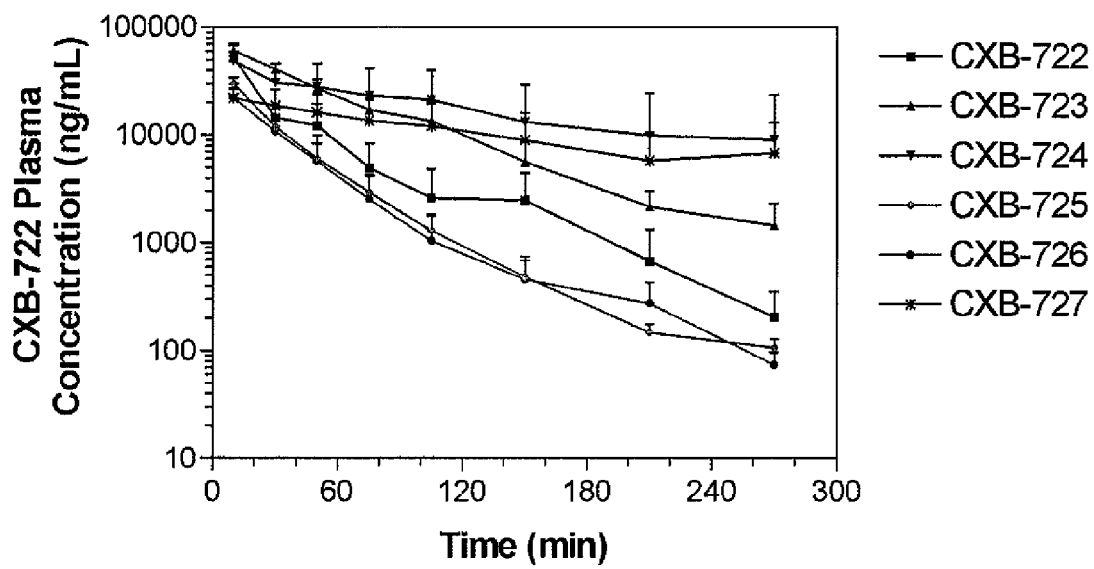
FIG. 24 represents the quantification of CXB-722 and other compounds in plasma in EXAMPLE 6 below.
Figure 25:
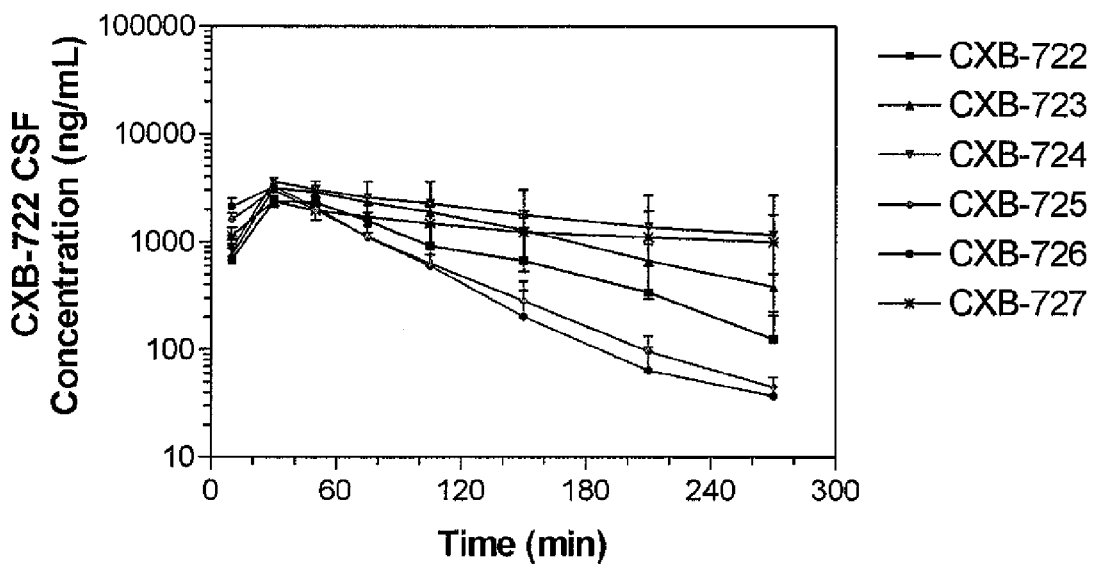
FIG. 25 represents the quantification of CXB-722 and other compounds in CSF in EXAMPLE 6 below.

The results are shown in FIGS. 24 and 25.

Example 7

Initial attempts to make the ester CXB-724 by employing a Fisher esterification in refluxing Xylene worked but took 2 days to complete. The dark wine red colored product was distilled at high temperature (215-220° C. @ 0.25 mmHg) and obtained as a colorless liquid in 58% yield (Scheme-2).

Scheme-2

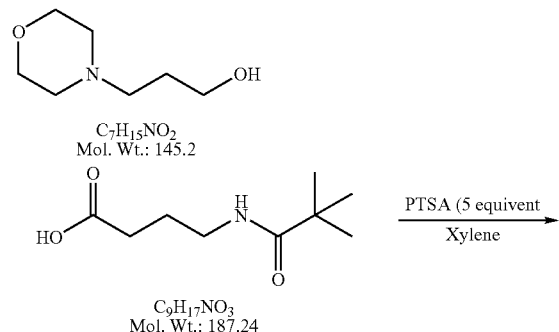

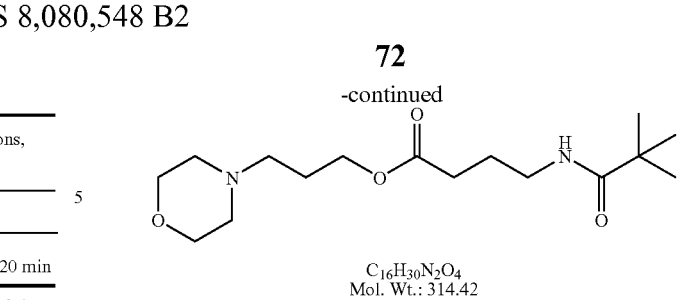

$C_{16}H_{30}N_2O_4$
Mol. Wt.: 314.42

Due to the long reaction time, low product yield and distillation requirement, other possibilities of making CXB-724 were considered. Fortunately, EDCI (1-Ethyl-3-[3-(dimethylamino)propyl]carbodiimide hydrochloride), HOBT (1-hydroxybenzotriazole) coupling conditions worked very efficiently in delivering the desired product (3 hours, RT, quantitative yield; Scheme-3). Thus, earlier limitations of time, yield and purification that were present with the Fisher esterification route were overcome.

Scheme-3

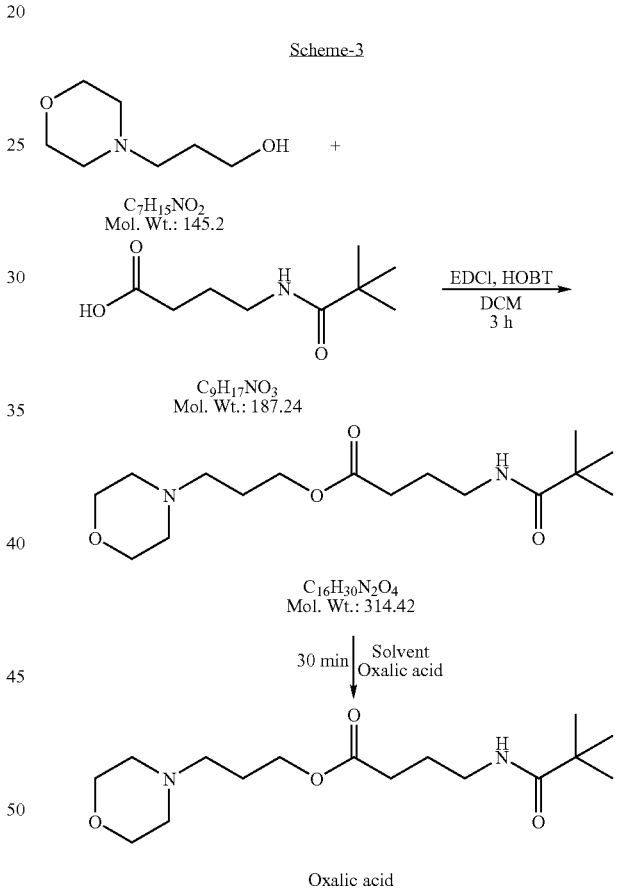

The salt formation of ester CXB 724 with various organic acids was also screened. Fortunately, Oxalic acid salt of Ester CXB-724 gave a very nice white, non-hygroscopic solid which is highly water soluble. A mild, facile synthesis of CXB-724 has been developed which can be either distilled (as the neutral compound) or crystallized as its oxalic salt. EDCI coupling method work efficiently to give essentially a quantitative yield of CXB-724. CXB-724 Oxalic acid salt has been successfully prepared in virtually quantitative yield. The water content of the oxalic acid salt is 3.14% (Batch 807165019) when left to "air dry" for more than a day. There is no further absorption of water by this salt upon continued exposure to air. Drying of the salt in an oven overnight at 40° C. under vacuum reduces the water content to 0.36% (Batch 807165019). Details of the methods follow:

Fisher Esterification of 3-Morpholine Propan-1-ol with 4-(pivalamido)butanoic acid Method-1:

To a suspension of 3-Morpholine propan 1-ol (5 g, 0.0345 mol), 4-(pivalamido)butanoic acid (5 g, 0.0266 mol) in anhydrous Xylene (50 mL) was added PTSA (P-Toluene Sulfonic Acid) (0.50 g, 0.0026 mol). The reaction mixture was refluxed (139° C.) until butanoic acid is completed by ELSD (evaporative light scattering detector) which took two (2) days. The dark red color was cooled to room temperature and distilled off the xylene under vacuum. Distillation of the residue under vacuum yielded 6.25 g (58%) at 215-220° C. at 0.25 mm Hg.

EDCI/HOBT coupling reactions were carried in three batches. However, only the largest scale reaction performed is discussed below.

Method-2:

To a solution of 4-(pivalamido)butanoic acid (100 g, 0.4968 mol) in anhydrous DCM (dichloromethane) (1 L) was added EDCI (114.28 g, 0.596 mol) followed by HOST (70.5 g, 0.5216 mol) at rt. To the resulting mixture 3-Morpholine propan-1-ol (79.4 g, 0.5465 mol) in anhydrous DCM (20 mL) was added slowly. The resulting mixture was stirred at rt for 3 h and quenched with water (200 mL). The reaction mixture is washed with water (1×500 mL), 10% NaHCO$_3$ (1×400 mL), water (2×400 mL) and dried over anhydrous Na$_2$SO$_4$. Filtration followed by concentration under reduced pressure afforded a thick pale orange color of CXB-724 (132 g, 85%).

Salt Formation Study of Ester CXB-724

Salt formation for CXB-724 against various organic acids shown in table-1 were studied.

| Malonic acid | HCl | Oxalic acid | Succinic acid | 4-Hydroxy benzoic acid | 4-Nitro benzoic acid | 4-Chloro benzoic acid | Citric acid |
|---|---|---|---|---|---|---|---|
| Oil | Hygroscopic | White solid | Oil | Oil | Oil | Oil | Semi solid |

Oxalic acid salt was used since it gave a nice, white, free flowing, non-hygroscopic solid. The advantage of this oxalic acid salt is that it is highly water soluble and so the best solvent for forming oxalic acid is screened keeping in mind the solvent toxicity. Following table-2 is the test.

Solvent Screen of Oxalic Acid Salt Formation with CXB 724

| | | Solvents | | | | |
|---|---|---|---|---|---|---|
| | MTBE | MTBE/EtOAc (1:1) | EtOAc | DCM-EtOAc | THF | EtOAc |
| Scale | 0.1 g | 2 g | 2 g | 2.0 g | 1.0 g | 1.0 g |
| Washing | 20% DCM-EtOAc | EtOAc and 20% DCM-EtOAc | EtOAc and 20% DCM-EtOAc | EtOAc and 20% DCM-EtOAc | THF (2 × 10 mL) | EtOAc (3 × 10 mL) |
| Recovery | (>80%) | 2.3 g (85%) | 2.33 g (85%) | 2.21 g (85%) | 1.12 g (86%) | 1.129 g (87%) |

Considering solvent toxicity, DCM, MTBE (Methyl tertiary-butyl ether) were removed and THF (etrahydrofuran) solvent was chosen because it removes some of the impurities ingrained/donated in the starting material (butanoic acid) and also THF is less toxic compare to DCM and MTBE inferred by toxicological table.

CXB-724 Salt of Oxalic Acid

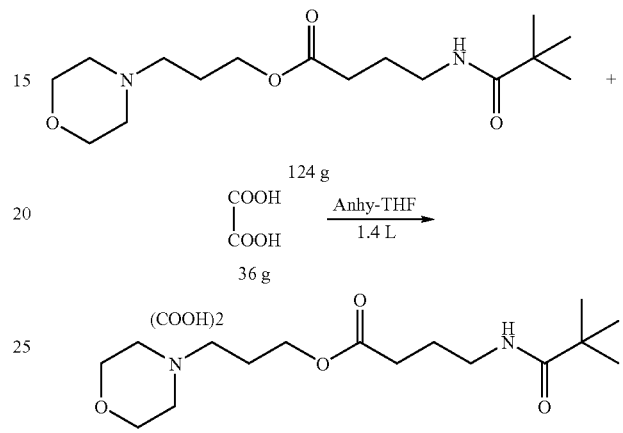

Figure 21:
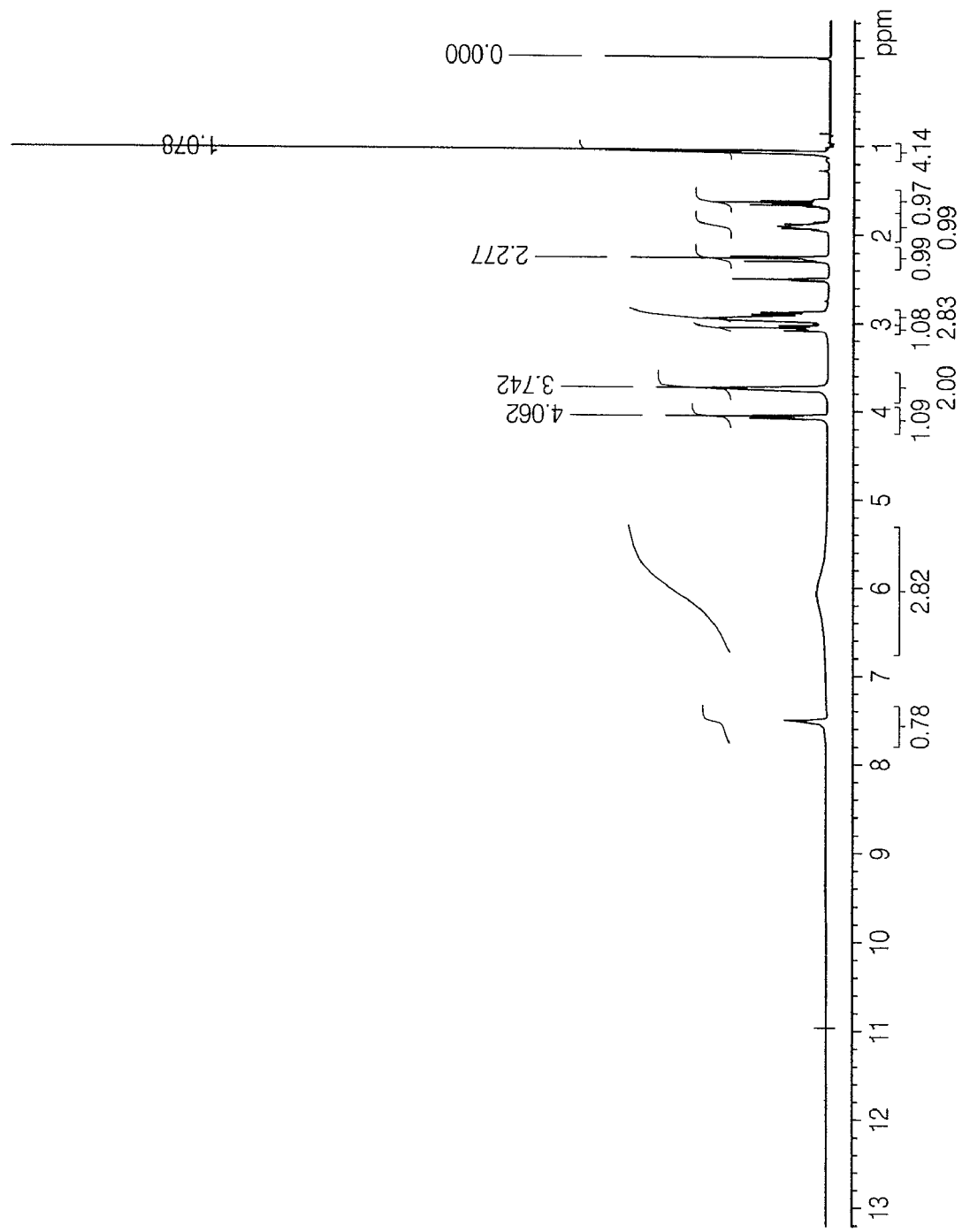
FIG. 21 is a proton NMR spectrum of a compound according to an embodiment shown in EXAMPLE 7 below.
Figure 22:
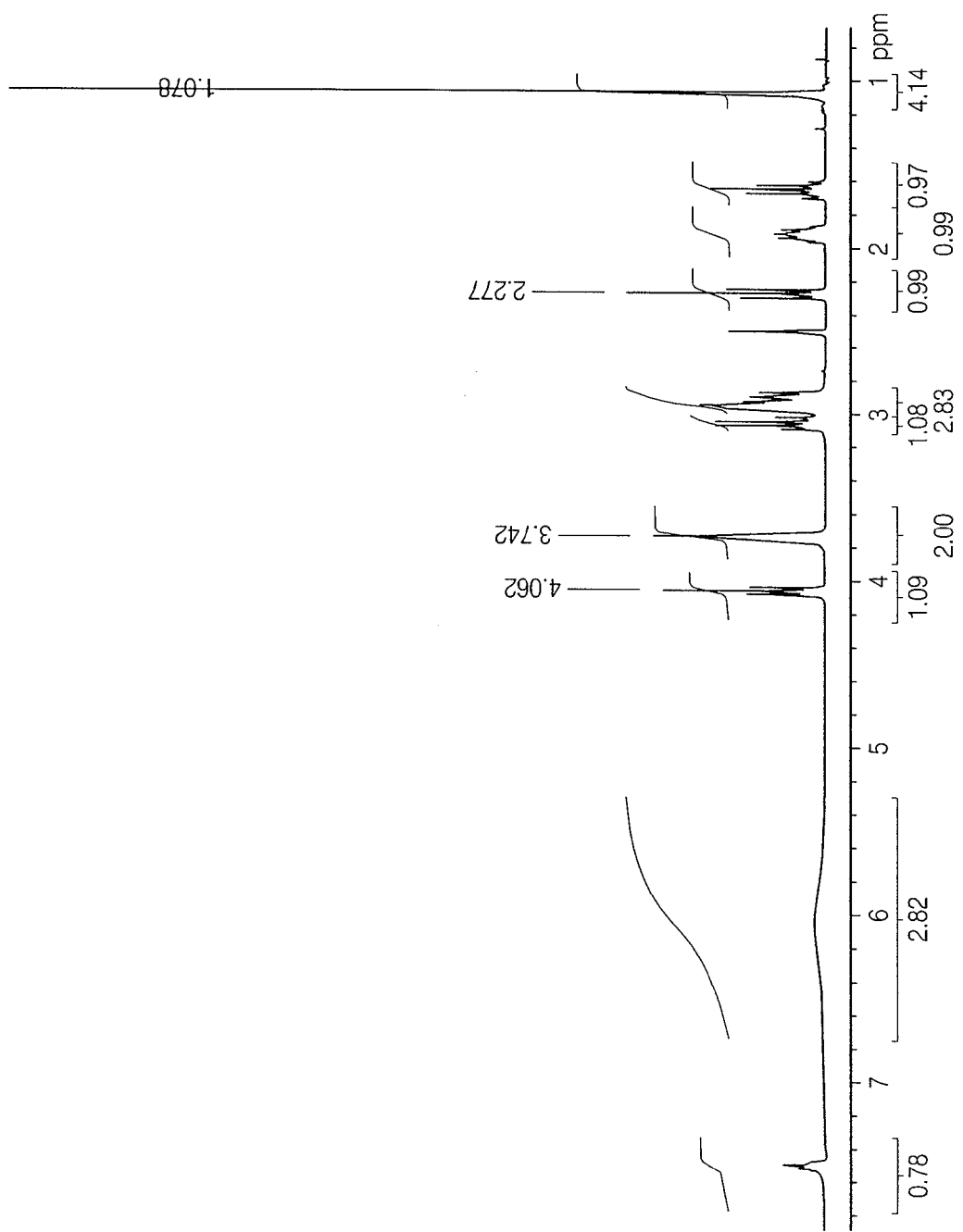
FIG. 22 is a proton NMR spectrum of a compound according to an embodiment shown in EXAMPLE 7 below.
Figure 23:
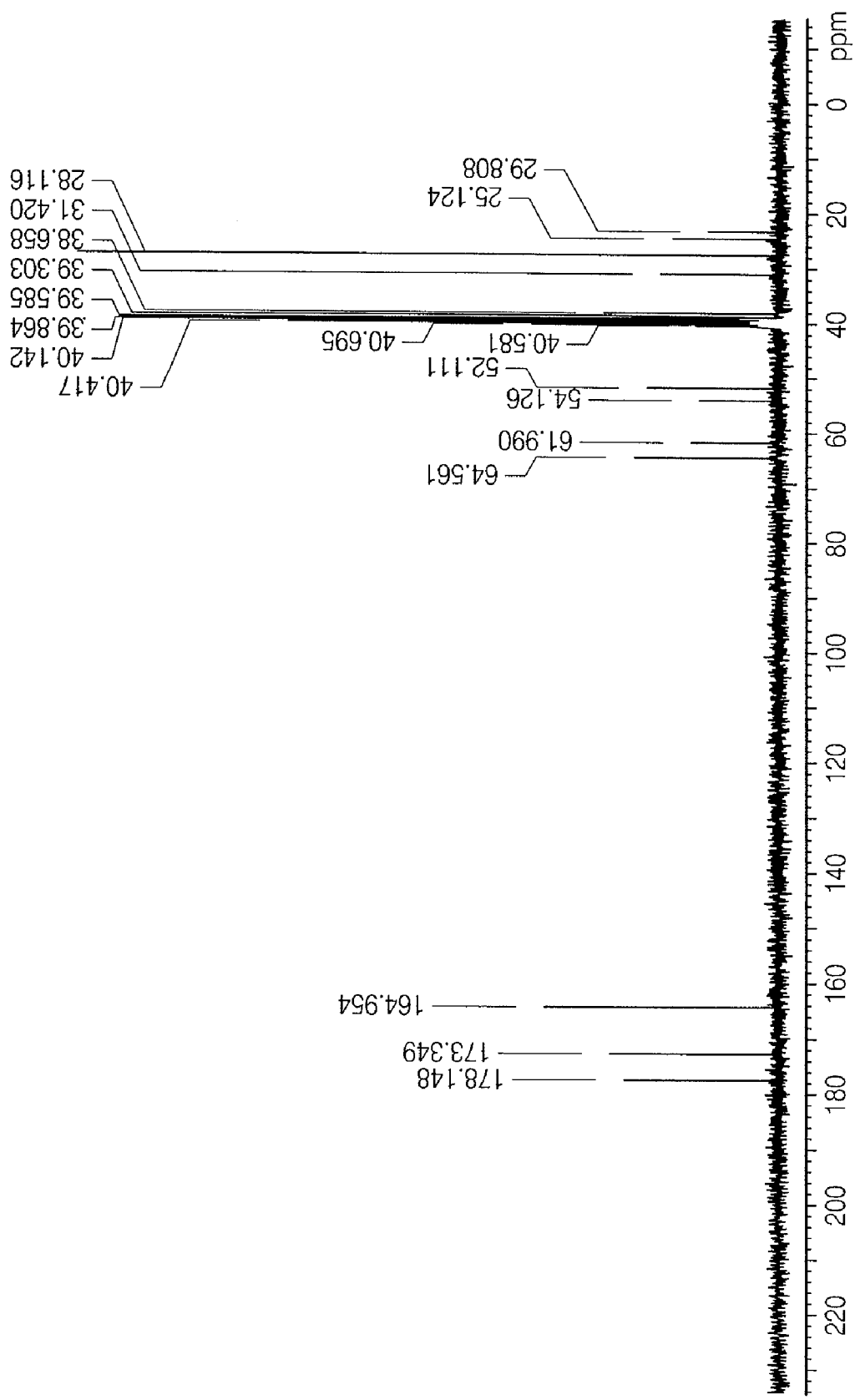
FIG. 23 is a $^{13}$C NMR spectrum of a compound according to an embodiment shown in EXAMPLE 7 below.

To a solution of oxalic acid (36 g, 0399 mol) in anhydrous THF (1.2 L) was added a solution of Ester CXB-724 (124 g, 0.395 mol) in THF (200 mL) at room temperature. The resulting mixture was stirred for 1 h and the solid was filtered, washed with anhydrous THF (2×200 mL) and dried to afford a white solid salt of oxalic acid with CXB-724 (142 g, 89%). The spectra for the above described products are shown in FIGS. 21-23.

EQUIVALENTS

The foregoing written specification is considered to be sufficient to enable one skilled in the art to practice the present embodiments. The foregoing description details certain pre-

What is claimed is:

1. A method of alleviating or relieving a symptom of a disease or disorder selected from the group consisting of: acute stress disorder; an affective disorder, a depressive disorder, a major depressive disorder, dysthymia, childhood depression, atypical depression, bipolar disorder, mania, hypomania, anxiety disorders, generalized anxiety disorder, social anxiety disorder, phobias, obsessive compulsive disorder, panic disorder and post-traumatic stress disorder, comprising administering a patient with an effective amount of a compound with the following structure:

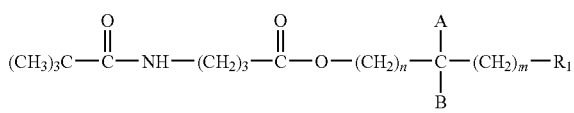

wherein, m is 0, 1, 2, 3 or 4;
wherein, n is 1, 2, 3, or 4;
wherein A and B are H;
and wherein $R_1$ is selected from the group consisting of:

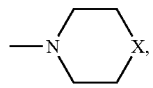

wherein X is oxygen, and
an unsymmetrical amine group of the formula

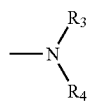

wherein $R_3$ and $R_4$ are independently selected from the group consisting of H, a $C_1$-$C_8$ branched alkyl, and a $C_1$-$C_8$ linear alkyl, or
a pharmaceutically acceptable salt thereof.

2. The method of claim 1, wherein $R_1$ is

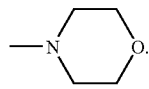

3. The method of claim 1, wherein n is 1, m is 0 and $R_1$ is

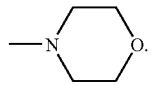

4. The Method of claim 1, wherein n is 2, m is 0 and $R_1$ is

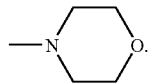

5. The method of claim 1, wherein n is 3, m is 0 and $R_1$ is

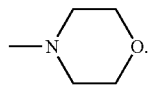

6. The method of claim 1, wherein n is 2.
7. The method of claim 1, wherein n is 3.
8. The method of claim 1, wherein n is 4.
9. The method of claim 1, wherein $R_1$ is an unsymmetrical amine group.
10. The method of claim 1, wherein $R_1$ is

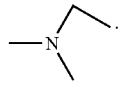

11. The method of claim 1, wherein n is 1, m is 0 and $R_1$ is

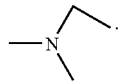

12. The method of claim 1, wherein n is 2, m is 0 and $R_1$ is

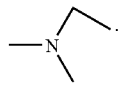

13. The method of claim 1, wherein the disease or disorder is acute stress disorder, an affective disorder, a depressive disorder or a major depressive disorder.
14. The method of claim 1, wherein the disease or disorder is an anxiety disorder or post-traumatic stress disorder.

* * * * *